United States Patent
Jaenisch et al.

(10) Patent No.: US 9,497,943 B2
(45) Date of Patent: Nov. 22, 2016

(54) NUCLEIC ACID CONSTRUCTS ENCODING REPROGRAMMING FACTORS LINKED BY SELF-CLEAVING PEPTIDES

(75) Inventors: Rudolf Jaenisch, Brookline, MA (US); Bryce Woodbury Carey, New York, NY (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 495 days.

(21) Appl. No.: 12/997,815

(22) PCT Filed: Jun. 15, 2009

(86) PCT No.: PCT/US2009/047423
§ 371 (c)(1),
(2), (4) Date: Oct. 21, 2011

(87) PCT Pub. No.: WO2009/152529
PCT Pub. Date: Dec. 17, 2009

(65) Prior Publication Data
US 2012/0028821 A1    Feb. 2, 2012

Related U.S. Application Data

(60) Provisional application No. 61/061,525, filed on Jun. 13, 2008, provisional application No. 61/077,068, filed on Jun. 30, 2008.

(51) Int. Cl.
| | | |
|---|---|---|
| *C12N 15/00* | (2006.01) | |
| *A01K 67/027* | (2006.01) | |
| *C12N 5/074* | (2010.01) | |
| *G01N 33/50* | (2006.01) | |
| *C12N 15/86* | (2006.01) | |
| *C12N 15/85* | (2006.01) | |
| *C12N 5/0735* | (2010.01) | |
| *C12N 15/79* | (2006.01) | |

(52) U.S. Cl.
CPC ......... *A01K 67/0271* (2013.01); *C12N 5/0696* (2013.01); *G01N 33/5008* (2013.01); *C12N 5/0606* (2013.01); *C12N 15/79* (2013.01); *C12N 15/85* (2013.01); *C12N 15/86* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/11* (2013.01); *C12N 2506/115* (2013.01); *C12N 2510/00* (2013.01); *C12N 2740/15041* (2013.01); *C12N 2740/15043* (2013.01); *C12N 2740/16043* (2013.01); *C12N 2799/027* (2013.01); *C12N 2800/108* (2013.01); *C12N 2840/203* (2013.01)

(58) Field of Classification Search
CPC  C12N 5/0696; C12N 2501/60; C12N 15/85; C12N 2501/602; C12N 2501/603; C12N 2501/604; C12N 2501/606; C12N 15/63; C12N 2501/608; C12N 2510/00; C12N 2799/027; C12N 2800/00; C12N 2800/108; C12N 2501/605; C12N 2506/45; C12N 2506/1307; C12N 2800/30; C12N 2506/136; C12N 15/86; C12N 15/79; C12N 2740/15041; C12N 2740/15043; C12N 2740/16043; C12N 2840/203; C12N 5/0606; C12N 2770/36143; C12N 2840/206

See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,015,037 B1 | 3/2006 | Furcht et al. | |
| 7,524,677 B2 | 4/2009 | Stockman et al. | |
| 7,601,699 B2 | 10/2009 | Eilertsen | |
| 7,682,828 B2 | 3/2010 | Jaenisch et al. | |
| 7,687,266 B2 | 3/2010 | Chambers et al. | |
| 8,071,369 B2 | 12/2011 | Jaenisch et al. | |
| 2002/0168660 A1 | 11/2002 | Chen et al. | |
| 2004/0137460 A1 | 7/2004 | Yamanaka et al. | |
| 2005/0287547 A1 | 12/2005 | Seligman | |
| 2006/0084172 A1 | 4/2006 | Muller et al. | |

(Continued)

FOREIGN PATENT DOCUMENTS

| | | |
|---|---|---|
| CN | 101855350 | 10/2010 |
| EP | 1 970 446 | 9/2008 |

(Continued)

OTHER PUBLICATIONS

Laiosa et al.Reprogramming of Committed T Cell Progenitors to Macrophages and Dendritic Cells by C/EBPa and PU.1 Transcription Factors. Immunity, 2006, vol. 25, pp. 731-744.*

(Continued)

*Primary Examiner* — Deborah Crouch
(74) *Attorney, Agent, or Firm* — Lisa M. Warren, Esq.; Morse, Barnes-Brown & Pendleton P.C.

(57) ABSTRACT

The disclosure relates to a method of reprogramming one or more somatic cells, e.g., partially differentiated or fully/terminally differentiated somatic cells, to a less differentiated state, e.g., a pluripotent or multipotent state. In further embodiments the invention also relates to reprogrammed somatic cells produced by methods of the invention, to chimeric animals comprising reprogrammed somatic cells of the invention, to uses of said cells, and to methods for identifying agents useful for reprogramming somatic cells.

17 Claims, 39 Drawing Sheets
(25 of 39 Drawing Sheet(s) Filed in Color)

(56) References Cited

U.S. PATENT DOCUMENTS

| | | |
|---|---|---|
| 2007/0032447 A1 | 2/2007 | Eilertsen |
| 2008/0066197 A1 | 3/2008 | Ying et al. |
| 2008/0280362 A1 | 11/2008 | Jaenisch et al. |
| 2009/0047263 A1 | 2/2009 | Yamanaka et al. |
| 2009/0068742 A1 | 3/2009 | Yamanaka |
| 2009/0227032 A1 | 9/2009 | Yamanaka et al. |
| 2010/0062533 A1* | 3/2010 | Yamanaka .................. 435/455 |
| 2010/0144031 A1 | 6/2010 | Jaenisch et al. |
| 2010/0221827 A1 | 9/2010 | Jaenisch et al. |
| 2010/0310525 A1 | 12/2010 | Chevalier et al. |
| 2011/0076678 A1 | 3/2011 | Jaenisch et al. |
| 2011/0151447 A1 | 6/2011 | Park |
| 2012/0028821 A1 | 2/2012 | Jaenisch et al. |
| 2012/0034192 A1 | 2/2012 | Young et al. |
| 2012/0282229 A1 | 11/2012 | Kannemeier et al. |
| 2013/0017596 A1* | 1/2013 | Townes et al. ............ 435/320.1 |
| 2013/0065311 A1* | 3/2013 | Yamanaka et al. .......... 435/465 |

FOREIGN PATENT DOCUMENTS

| | | |
|---|---|---|
| WO | WO 99/55841 | 11/1999 |
| WO | WO 00/27995 | 5/2000 |
| WO | WO 02/097090 | 12/2002 |
| WO | WO 2005/080598 | 9/2005 |
| WO | WO 2005/090557 | 9/2005 |
| WO | WO 2007/069666 A1 | 6/2007 |
| WO | WO 2008/001391 A2 | 1/2008 |
| WO | WO 2008/118820 | 10/2008 |
| WO | WO 2008/124133 A1 | 10/2008 |
| WO | WO 2009/117439 A2 | 9/2009 |
| WO | WO 2009/133971 | 11/2009 |
| WO | WO 2009/152529 A2 | 12/2009 |
| WO | WO 2010/033920 A2 | 3/2010 |

OTHER PUBLICATIONS

Chinnasamy et al. Multicistronic lentiviral vectors containing the FMDV 2A cleavage factor demonstrate robust expression of encoded genes at limiting MOI. Virology Journal, 2006, vol. 3, pp. 14-29, doi:10.1186/1743-422X-3-14.*

Okita et al. Generation of germline-competent induced pluripotent stem cells. Nature, Jun. 6, 2007, vol. 448, pp. 313-318, doi:10.1038/nature05934 in view of 201000062533.*

Non-Final Office Action for U.S. Appl. No. 12/595,041, mailed May 9, 2012.

Hasegawa, et al., "Efficient multicistronic expression of a transgene in human embryonic stem cells," *Stem Cells*, 25(7): 1707-1712 (2007).

Ho, et al., "Synthetic Protein Transduction Domains: Enhanced Transduction Potential in Vitro and in Vivo," Cancer Research, 61: 474-477 (2001).

Ma, et al., "G9a and Jhdma2a Regulate Embryonic Stem Cell Fusion-Induced Reprogramming of Adult Neural Stem Cells", *Stem Cells*, 26)8): 2131-2141 (2008).

Sells, et al., "Delivery of Protein into Cells Using Polycationic Liposomes," *BioTechniques* 19(1):72-78 (1995).

Stacey, et al., "Microinjection of Transforming *ras* Protein Induces c-*fos* Expression," *Molecular and Cellular Biology*, 7(1): 523-527 (1987).

Wadia, et al., "Protein Transduction Technology," *Analytical Biotechnology*, 13: 52-56 (2002).

Scholer, et al., "New type of POU domain in germ line-specific protein Oct-4", Letters to Nature, 344: 435-439 (1990).

Bilic, et al., "Concise Review: Induced Pluripotent Stem Cells Versus Embryonic Stem Cells: Close Enough or Yet Too Far Apart?", *Stem Cells*, 30:33-41(2012).

Chin, et al., "Induced Pluripotent Stem Cells and Embryonic Stem Cells are Distinguished by Gene Expression Signatures", *Cell Stem Cell*, 5:111-123(2009).

Chin, et al., "Molecular Analyses of Human Induced Pluripotent Stem Cells and Embryonic Stem Cells", *Cell Stem Cell*, 7(2):263-269(2010).

Munoz, et al., "The Quantitative Proteomes of Human-Induced Pluripotent Stem Cells and Embryonic Stem Cells", *Molecular Systems Biology*, 7(550):1-13(2011).

Polouliakh, et al., "Reprogramming Resistant Genes: In-Depth Comparison of Gene-Expressions Among iPS, ES, and somatic cells", *Frontiers in Physiology*, 4(7):1-9(2013).

Meissner, et al., "Direct Reprogramming of genetically unmodified fibroblasts into pluripotent stem cells", *Nature Biotechnology*, 25(10): 1177-1181 (2007).

Strelchenko, et al. "Reprogramming of human somatic cells by embryonic stem cell cytoplast", *Reprod. Biomed Online*, 12(1): 107-111 (2006).

Cowan, et al., Nuclear Reprogramming of Somatic Cells After Fusion with Human Embryonic Stem Cells, *Science*, 309:1369-1373 (2005).

Ait-Si-Ali, et al., "A Suv39h-dependent mechanism for silencing S-phase genes in differentiating but not in cycling cells", *EMBO Journal*, 23:605-615 (2004).

Maherali, et al., "Directly Reprogrammed Fibroblasts Show Global Epigenetic Remodeling and Widespread Tissue Contribution", Cell Stem Cell, 1:55-70(2007).

Sarraf, et al., "Methyl-CpG Binding Protein MBD1 Couples Histone H3 Methylation at Lysine 9 by SETDB1 to DNA Replication and Chromatin Assembly", Molecular Cell, 15:595-605 (2004).

Supplementary European Search Report for Application No. EP 09763816, dated Nov. 29, 2012.

Partial European Search Report for Application No. EP12003893, dated Jun. 24, 2013.

Final Office Action for U.S. Appl. No. 12/595,041, mailed Dec. 7, 2012.

Non-Final Office Action for U.S. Appl. No. 13/646,411, mailed Feb. 27, 2013.

Non-Final Office Action for U.S. Appl. No. 13/119,891, mailed May 15, 2013.

Non-Final Office Action for U.S. Appl. No. 12/703,061, mailed Aug. 20, 2013.

Non-Final Office Action for U.S. Appl. No. 13/646,444, mailed Aug. 20, 2013.

PubMed Oct4 gene, Printout from www.ncbi.nlm.nih.gov/nuccore/NM_013633.3, pp. 1-12, Sep. 19, 2013.

Palmqvist, et al., "Correlation of Murine Embryonic Stem Cell Gene Expression Profiles with Functional Measures of Pluripotency", Stem Cells, 23:663-680 (2005).

Yu, et al., "Induced pluripotent stem cell lines derived from human somatic cells", Science, 318:1917-1920 (2007).

Sox2 cDNA, printout from http://ncbi.nih.gov/nuccor/BC057574.1, pp. 1-13 (2013).

Oct4 cDNA, printout from http://ncbi.nih.gov/nuccor/BC117437.1, pp. 1-10 (2013).

Non-Final Office Action for U.S. Appl. No. 13/646,430, mailed Sep. 20, 2013.

Non-Final Office Action for U.S. Appl. No. 13/646,420, mailed Sep. 23, 2013.

Non-Final Office Action for U.S. Appl. No. 12/595,041, mailed Oct. 2, 2013.

Non-Final Office Action for U.S. Appl. No. 13/646,411, mailed Oct. 31, 2013.

Aoi, et al., Generation of Pluripotent Stem Cells from Adult Mouse Liver and Stomach Cells. Science, 321: 699-702 (2008).

Avilion, et al., Multipotent cell lineages in early mouse development depend on SOX2 function. Genes & Development, 17:126-140 (2003).

Ben-Shushan, et al., Extinction of Oct-3/4 gene expression in embryonal carcinoma x fibroblast somatic cell hybrids is accompanied by changes in the methylation status, chromatin structure, and transcriptional activity of the Oct-3/4 upstream region. Molecular and Cellular Biology, 13(2):891-901 (1993).

Bortvin, et al., Incomplete Reactivation of Oct4-related in Mouse Embryos Cloned from Somatic Nuclei. Development, 130:1673-1680 (2003).

(56) References Cited

OTHER PUBLICATIONS

Boyer, et al., Polycomb complexes repress developmental regulators in murine embryonic stem cells. Nature, 441(7091):349-353 (2006).
Brambrink, et al., Sequential Expression of Pluripotency Markers During Direct Reprogramming of Mouse Somatic Cells. Cell Stem Cell, 2(2): 151-159 (2008).
Bronson, et al., Single-copy transgenic mice with chosen-site integration. Proc. Natl. Acad. Sci. USA, 93:9067-9072 (1996).
Bru, et al., Rapid induction of pluripotency genes after exposure of human somatic cells to mouse ES cell extracts. Experimental Cell Research, 314:2634-2642 (2008).
Buske, et al., Overexpression of HOXA10 perturbs human lymphomyelopoiesis in vitro and in vivo. Blood, 97(8):2286-2292 (2001).
Carey, et al., Reprogramming of murine and human somatic cells using a single polycistronic vector. PNAS, 106:157-162 (2009).
Chambers, et al., Functional expression cloning of nanog, a pluripotency sustaining factor in embryonic stem cells. Cell, 113:643-655 (2003).
Chen, et al., Establishment and Maintenance of Genomic Methylation Patterns in Mouse Embryonic Stem Cells by Dnmt3a and Dnmt3b. Molecular and Cellular Biology, 23(16):5594-5605 (2003).
Daniels, et al., Analysis of Gene Transcription in Bovine Nuclear Transfer Embryos Reconstructed with Granulosa Cell Nuclei. Biology of Reproduction, 63:1034-1040 (2000).
Eminli, et al., Reprogramming of Neural Progenitor Cells into iPS Cells in the Absence of Exogenous Sox2 Expression. Stem Cells, 26:2467-2474 (2008).
Gossen, et al., Transcriptional activation by tetracyclines in mammalian cells. Science, 268(5218):1766-1769 (1995).
Greiner, et al., Identification of a specific inhibitor of the histone methyltransferase SU(VAR)3-9. Nature Chemical Biology, 1:143-145 (2005).
Hanna, et al. Direct reprogramming of terminally differentiated mature B lymphocytes to pluripotency. Cell 133, 250-264 (2008).
Hansis, et al., Analysis of *Oct-4* expression and ploidy in individual human blastomeres. Molecular Human Reproduction, 7: 155-161 (2001).
Helgason, et al., Overexpression of HOXB4 enhances the hematopoietic potential of embryonic stem cells differentiated in vitro. Blood, 87(7):2740-2749 (1996).
Hochedlinger, et al., Monoclonal mice generated by nuclear transfer from mature B and T donor cells. Nature, 415:1035-1038 (2002).
Hochedlinger, et al., Nuclear transplantation, embryonic stem cells, and the potential for cell therapy. The New England Journal of Medicine, 349(3):275-286 (2003).
Ihle, STATs: Signal Transducers and Activators of Transcription. Cell, 84: 331-334 (1996).
Jackson-Grusby, et al., Loss of Genomic Methylation Cases p53-Dependent Apoptosis and Epigenetic Deregulation. Nature Genetics, 27: 31-39 (2001).
Jaenisch, Rudolf, Abstract "*In vitro reprogramming of somatic cells into pluripotent ES-like cells*" National Institutes of Health Grant No. 5 R37 HD045022-06 through 5 R37 HD045022-07 Funding Dates 2008 through 2009.
Jaenisch, Rudolf, Abstract "*Nuclear Closing and the Reprogramming of the Genome*" National Institutes of Health Grant No. 5 R37 HD045022-01 through 5 R37 HD045022-05, Funding Dates 2003 through 2007.
Jaenisch, Rudolf, Abstract "*Genomic Imprinting and the Cloning of Mice*" National Institutes of Health Grant No. 5 R01 CA084198-01 through 5R01 CA084198-09, Funding Dates 2000 through 2008.
Jaenisch, Rudolf, Abstract "*Epigenetics, stem cells, and cancer*" National Institutes of Health Grant Nos. 5 RO1 CA087869-06 through 5 RO1 CA087869-09, Funding Dates 2006 through 2009.
Jaenisch, Rudolf, Abstract "*DNA Methylation, Gene Regulation, and Cancer*" National Institutes of Health Grant Nos. 5 RO1 CA087869-01 through 5 RO1 CA087869-05, Funding Dates 2001 through 2005.
Jaenisch, et al., Nuclear cloning, stem cells, and genomic reprogramming. Cloning and Stem Cells, 4(4):389-396-2002).
Jaenisch & Young, Stem Cells, the Molecular Circuitry of Pluripotency and Nuclear Reprogramming. Cell, 132, 567-582 (2008).
Kaufman, et al., Hematopoietic colony-forming cells derived from human embryonic stem cells. PNAS 98(19)10716-10721 (2001).
Kubicek, et al., Reversal of H3K9me2 by a small-molecule inhibitor for the G9a histone methyltransferase. Molecular Cell, 25(3):473-81 (2007).
Kyba et al., HoxB4 confers definitive lymphoid-myeloid engraftment potential on embryonic stem cell and yolk sac hematopoietic progenitors. Cell, 109:29-37 (2002).
Lenardo et al., Repression of the IgH Enhancer in Teratocarcinoma Cells Associated with a Novel Octamer Factor. Science, New Series, 243(4890):544-546 (1989).
Li, et al., Murine embryonic stem cell differentiation is prompted by SOCS-3 and inhibited by the zinc finger transcription factor Klf4. Blood, 105:635-637 (2005).
Loh, et al., The Oct4 and Nanog transcription network regulates pluripotency in mouse embryonic stem cells. Nature Genetics, 38(4): 431-440 (2006).
Lowry, et al. Generation of human induced pluripotent stem cells from dermal fibroblasts. PNAS, 105(8):2883-2888 (2008).
Matsuoka, et al., Generation of definitive hematopoietic stem cells from murine early yolk sac and paraaortic splanchnopleures by aorta-gonad-mesonephros region-derived stromal cells. Blood, 98(1):6-12 (2001).
McWhir, et al., Selective ablation of differentiated cells permits isolation of embryonic stem cell lines from murine embryos with a non-permissive genetic background. Nature Genetics, 14:223-226 (1996).
Mitsui et al., The Homeoprotein Nanog is Required for Maintenance of Pluripotency in Mouse Epiblast and ES Cells. Cell, 113: 631-642 (2003).
Mountford, et al., Dicistronic targeting constructs: Reporters and modifiers of mammalian gene expression. Proceedings of the National Academy of Sciences, 91: 4303-4307 (1994).
Munsie, et al., Transgenic strategy for demonstrating nuclear reprogramming in the mouse. Cloning Stem Cells, 4(2):121-130 (2002).
Naito, et al., Journal of Reproduction and Fertility 113:137-143 (1998).
Nichols, et al., Formation of Pluripotent Stem Cells in the Mammalian Embryo Depends on the POU Transcription. Factor Oct4. Cell, 95: 379-391 (1998).
Niwa, et al., Quantitative expression of Oct-3/4 defines differentiation, dedifferentiation or self-renewal of ES cells. Nature Genetics, 24: 372-376 (2000).
Okita, et al., Generation of Mouse Induced Pluripotent Stem Cells Without Viral Vectors. Science, 322:949-953 (2008).
Peled, et al., Dependence of human stem cell engraftment and repopulation of NOD/SCID mice on CXCR4. Science, 283:845-848 (1999).
Pesce, et al., Oct-4: Gatekeeper in the beginnings of mammalian development. Stem Cells, 19:271-278 (2001).
Qi, et al., The magic of four: induction of pluripotent stem cells from somatic cells by Oct4, Sox2, Myc and Klf4. Cell Research, 17:578-580 (2007).
Radcliffe, et al., Multiple gene products from a single vector: 'self-cleaving' 2A peptides. Gene Therapy, 11:1673-1674 (2004).
Ramalho-Santos, et al., 'Stemness': Transcriptional Profiling of Embryonic and Adult Stem Cells. Science, 298: 597-600 (2002).
Ryan, et al., Cleavage of foot-and-mouth disease virus polyprotein is mediated by residues located within a 19 amino acid sequence. Journal of General Virology, 72:2727-2732 (1991).
Savarese, et al., Hematopoletic Precursor Cells Transiently Reestablish Permissiveness for X Inactivation. Molecular and Cellular Biology, 26(19): 7167-7177 (2006).

(56) References Cited

OTHER PUBLICATIONS

Shields, et al., Identification and Characterization of a Gene Encoding a Gut-Enriched Kruppel-like Factor Expressed during Growth Arrest. Journal of Biological Chemistry, 271(33):20009-20017 (1996).
Stadfeld, et al., Reprogramming of Pancreatic β Cells into Induced Pluripotent Stem Cells. Current Biology, 18:890-894 (2008).
Stem Cells: Scientific Progress and Future Research Directions. Department of Health and Human Services. Jun. 2001, </info/scireport/2001report>. Chapter 4: The Adult Stem Cell, pp. 23-42.
Tada, et al., Nuclear Reprogramming of Somatic Cells by In Vitro Hybridization with ES cells. Current Biology, 11: 1553-1558 (2001).
Takahashi, et al., Induction of Pluripotent Stem Cells from Adult Human Fibroblasts by Defined Factors. Cell, 131, 861-872 (2007).
Takahashi, et al., Induction of Pluripotent Stem Cells from Mouse Embryonic and Adult Fibroblast Cultures by Defined Factors. Cell, 126: 663-676 (2006).
Thomson, et al., Embryonic Stem Cell Lines Derived from Human Blastocysts. Science, 282, 1145-1147 (1998).
Wernig, et al., A drug-inducible transgenic system for direct reprogramming of multiple somatic cell types. Nature Biotechnology, 26(8):916-924 (2008).
Wernig, et al., In vitro reprogramming of fibroblasts into a pluripotent ES-cell-like state. Nature, 448: 318-324 (2007).
Wernig, et al., Neurons derived from reprogrammed fibroblasts functionally integrate into the fetal brain and improve symptoms of rats with Parkinson's disease. PNAS, 105(15):5856-5861 (2008).
Yamanaka, Strategies and New Developments in the Generation of Patient-Specific Pluripotent Stem Cells. Cell Stem Cell, 1: 39-49 (2007).
Yeom et al., "Germline regulatory element of Oct-4 specific for the totipotent cycle of embryonal cells," Development,122:881-897 (1996).
Ying, et al., BMP induction of Id proteins suppresses differentiation and sustains embryonic stem cell self-renewal in collaboration with STAT3. Cell, 115: 281-292 (2003).
Yoshimizu, et al., Germline-specific expression of the Oct-4/green fluorescent protein (GFP) transgene in mice, Development, Growth & Differentiation, 41:675-684 (1999).
Young, Richard, Abstract "Transcriptional Regulatory Networks in Living Cells " National Institutes of Health Grant No. 5 R01 HG002668-04A1 through 5 R01 HG002668-06, Funding Dates 2007 through 2009.
Young, Richard, Abstract "Transcriptional Regulatory Network in Living Cells " National Institutes of Health Grant No. 5 R01 HG002668-01 through 5 R01 HG002668-03S1, Funding Dates 2003 through 2006.
Yu, et al., Induced pluripotent stem cell lines derived from human somatic cells. Science, 318(5858):1917-20 (2007).
Zakhartchenko, et al., Adult cloning in cattle: potential of nuclei from a permanent cell line and from primary cultures. Molecular Reproduction and Development, 54:264-272 (1999).
Zambrowicz, et al., Disruption of overlapping transcripts in the ROSA βgeo 26 gene trap strain leads to widespread expression of β-galactosidase in mouse embryos and hematopoietic cells. Proc. Natl. Acad. Sci. USA, 94:3789-3794 (1987).
Zhou, et al., Generation of Induced Pluripotent Stem Cells Using Recombinatnt Proteins. Cell Stem Cell, 4:381-384 (2009).
BLAST Alignment SEQ ID 16 (ECAT4).
Sox2. print out from Pubmed http://www.ncbi.nlm.nih.gov/nuccore/127140985?ordinalp...ntrez.Sequence.Sequence_ResultsPanel.Sequence_RVDocSum p. 1-6, printed Apr. 7, 2009.
Nanog. Printout from Pubmed http://www.ncbi.nlm.nih.gov/nuccore/153791181?ordinalp...netrez.Sequence.Sequence_ResultsPanel.Sequence_RVDocSum p1-6, printed Apr. 7, 2009.
Jaenisch, Rudolf, Abstract *"Programming and Reprogramming Human Cells"* National Institutes of Health Grant No. 5 R01 CA084198-10, Funding Date 2009.
International Search Report for International Application PCT/US08/04516, dated Sep. 10, 2008.
International Search Report for International Application PCT/US2009/047423, dated May 3, 2010.
International Search Report for International Application PCT/US2009/057692, dated Jun. 30, 2010.
Supplementary European Search Report for Application No. EP 08742630.0, dated Mar. 25, 2010.
Office Action for U.S. Appl. No. 10/997,146, mailed Nov. 3, 2006.
Final Office Action for U.S. Appl. No. 10/997,146, mailed Aug. 14, 2007.
Office Action for U.S. Appl. No. 10/997,146, mailed Jul. 22, 2008.
Office Action for U.S. Appl. No. 10/997,146, mailed Apr. 9, 2009.
Office Action for U.S. Appl. No. 12/703,015, mailed Oct. 28, 2010.
Final Office Action for U.S. Appl. No. 12/703,015, mailed Jul. 8, 2011.
Office Action for U.S. Appl. No. 12/703,061, mailed Oct. 28, 2010.
Final Office Action for U.S. Appl. No. 12/703,061, mailed Jul. 14, 2011.
Office Action for U.S. Appl. No. 12/703,061, mailed Sep. 19, 2011.
Notice of Allowance in U.S. Appl. No. 10/997,146, mailed Jan. 26, 2010.
Notice of Allowance in U.S. Appl. No. 12/703,015, mailed Sep. 16, 2011.
Kong, et al., "Lack of specificity of fibroblast-specific protein 1 in cardiac remodeling and fibrosis", *American Journal of Physiology Heart and Circulatory Physiology*, 305: H1363-1372 (2013).
Nakagawa, et al., "Generation of induced pluripotent stem cells without Myc from mouse and human fibroblasts", *Nature Biotechnology*, 26(1): 101-106 (2008).
Final Office Action for U.S. Appl. No. 13/646,430, mailed Apr. 1, 2014.
Final Office Action for U.S. Appl. No. 13/646,444, mailed Apr. 2, 2014.
Final Office Action for U.S. Appl. No. 12/703,061, mailed Apr. 11, 2014.
Final Office Action for U.S. Appl. No. 13/646,411, mailed May 9, 2014.
Non-Final Office Action for U.S. Appl. No. 13/646,420, mailed May 27, 2014.
Final Office Action for U.S. Appl. No. 12/595,041, mailed May 30, 2014.
Feldman, et al., "G9a-mediated irreversible epigenetic inactivation of Oct-3/4 during early embryogenesis", *Nature Cell Biology*, 455: 627-633 (2008).
Zhou, et at "In vivo reprogramming of adult pancreatic exocrine cells to b-cells", *Nature*, 455: 627-633 (2008).
Non-Final Office Action for U.S. Appl. No. 13/119,891, mailed Jan. 2, 2014.
Notice of Allowance for U.S. Appl. No. 12/703,061, dated Nov. 7, 2014.
Notice of Allowance for U.S. Appl. No. 13/646,411, dated Dec. 8, 2014.
Non-Final Office Action for U.S. Appl. No. 13/646,430, dated Dec. 8, 2014.
Silva, et al., "Nanog promotes transfer of pluripotency after cell fusion", Nature, 441: 997-1001 (2006).
Shi, et al., Dynamic Regulation of Histone Lysine Methylation by Demethylases, Molecular Cell, 25: 1-14 (2007).
Final Office Action for U.S. Appl. No. 13/119,891, mailed Aug. 18, 2014.
Notice of Allowance for U.S. Appl. No. 13/646,420, dated Sep. 17, 2014.
Notice of Allowance for U.S. Appl. No. 13/646,444, dated Sep. 22, 2014.
Szymczak, et al., "Correction of multi-gene deficiency in vivo using a single "self-cleaving" 2A peptide-based retroviral vector," Nature Biotechnology 22(5): 589-594 (2004).
Non-Final Office Action for U.S. Appl. No. 12/595,041, dated Apr. 3, 2015.
Final Office Action for U.S. Appl. No. 12/595,041, dated Oct. 30, 2015.
Cavaleri, et al.,"Nanog: A New Recruit to the Embryonic Stem Cell Orchestra", Cell 113: 551-557 (2003).

(56) References Cited

OTHER PUBLICATIONS

Stevanovic, et al. The cDNA sequence and chromosomal location of the human SOX2 gene:, Mammalian Genome 5: 640-642 (1994).
Notice of Allowance for U.S. Appl. No. 13/646,430, dated Jun. 18, 2015.
Fawell, et al., "Tat-Mediated delivery of heterologous proteins into cells", *Proceedings of the National Academy of Science*, 91: 664-668 (1994).
Non-Final Office Action for U.S. Appl. No. 14/473,250, dated Aug. 25, 2015.
Notice of Allowance for U.S. Appl. No. 12/595,041, mailed Mar. 7, 2016.
Final Office Action for U.S. Appl. No. 14/473,250, dated Apr. 26, 2016.
Non-final Office Action for U.S. Appl. No. 14/923,321, mailed Aug. 2, 2016.

* cited by examiner

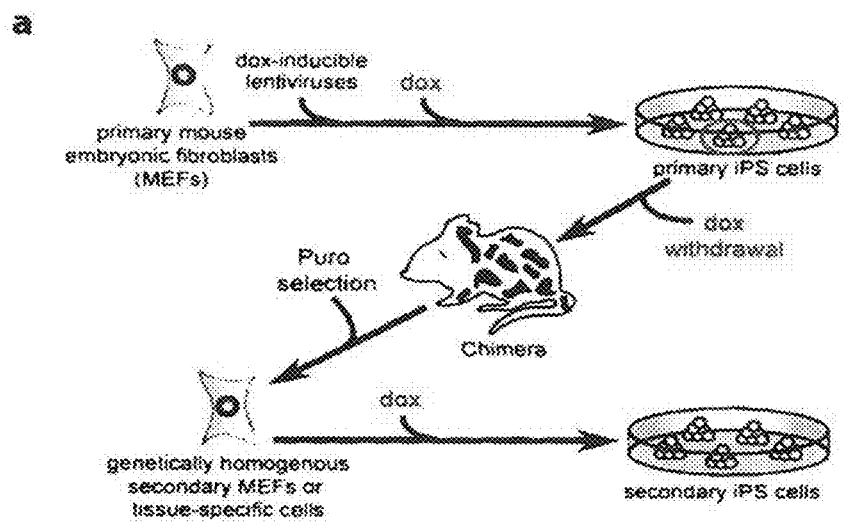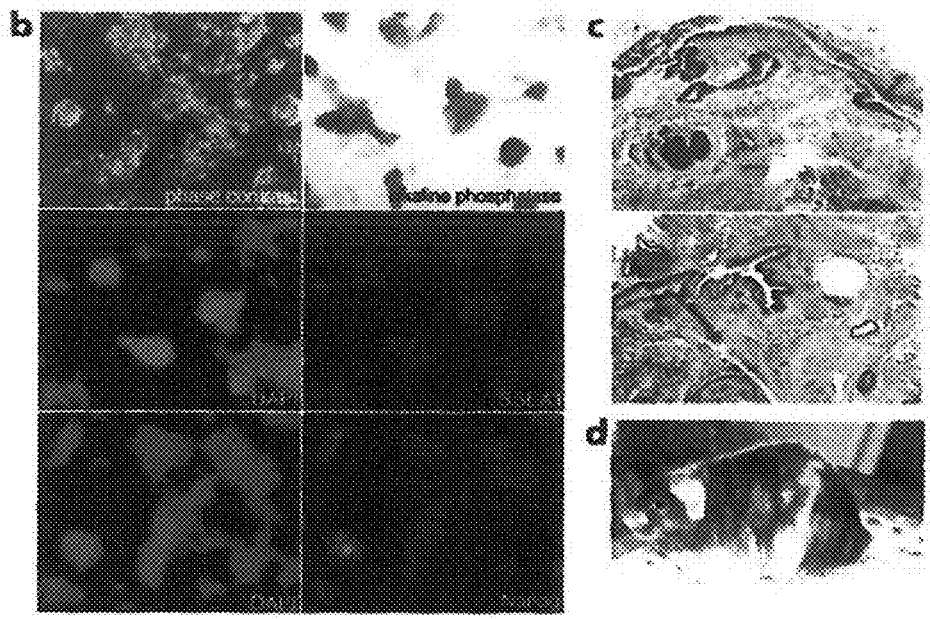
Figs. 1A-AD

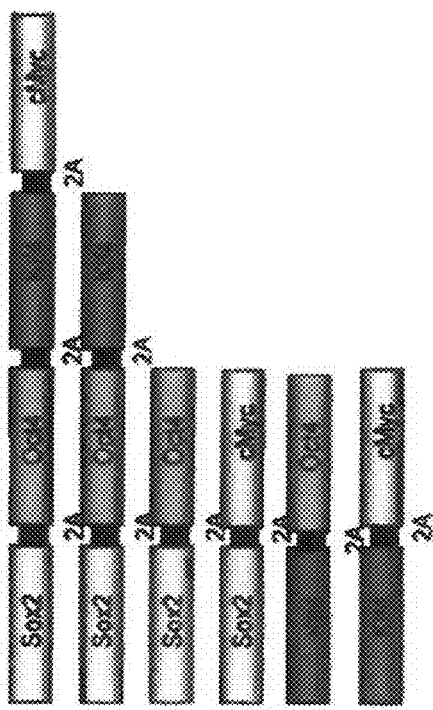
Fig. 13A
A

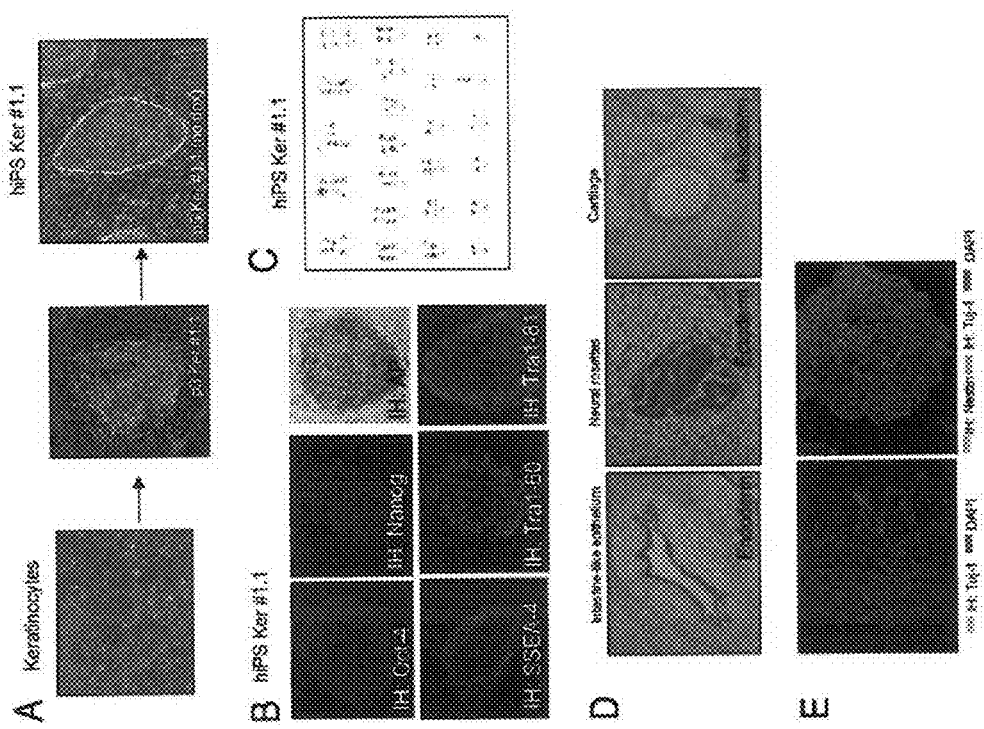
Figs. 17A-E

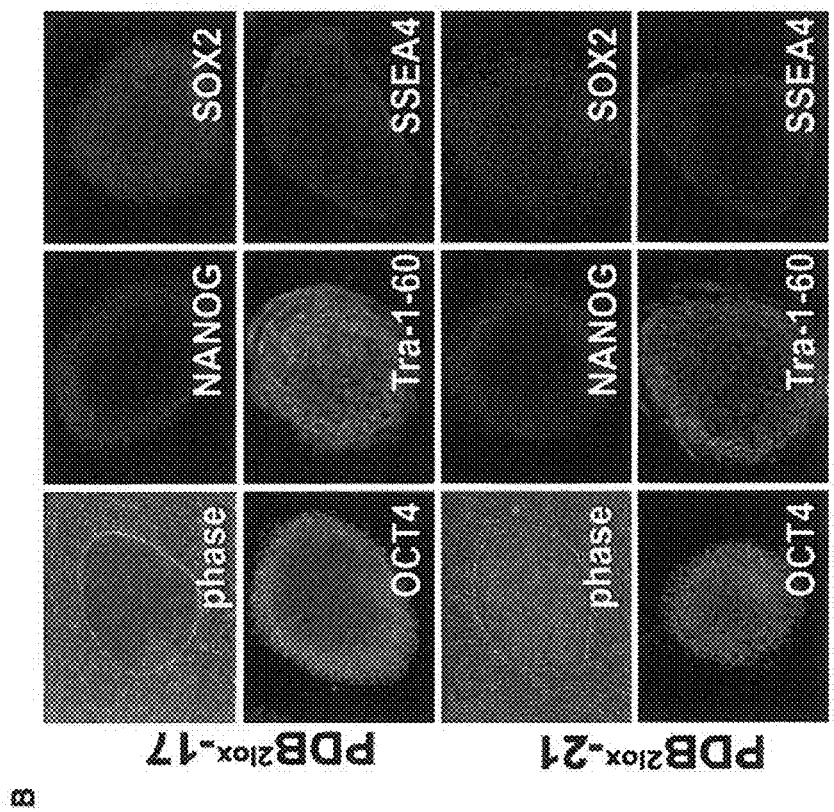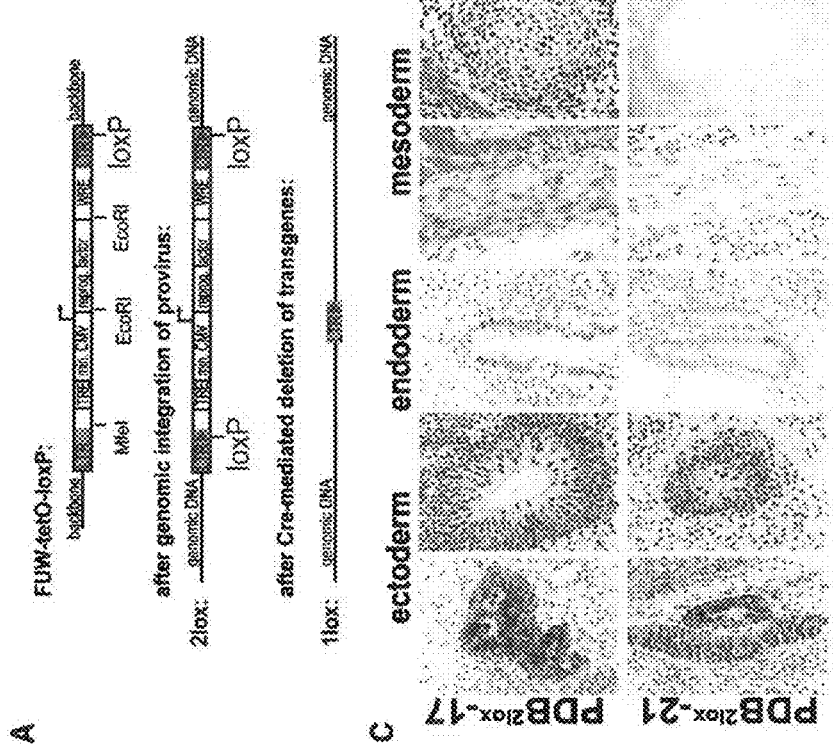
Figs. 29A-C

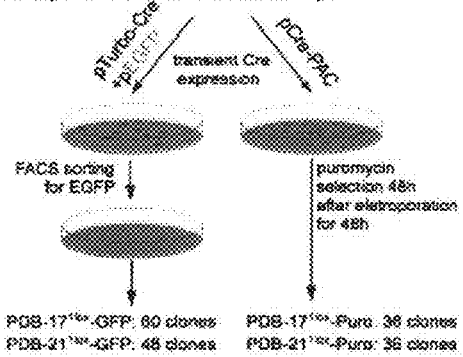
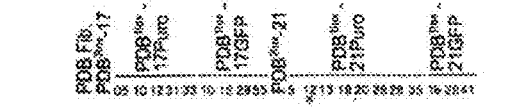
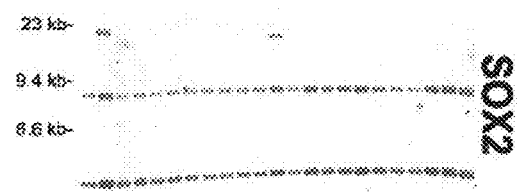
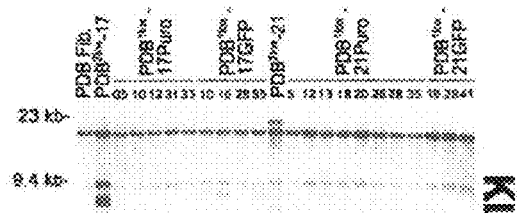
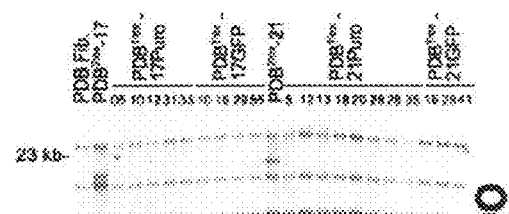
Figs. 30A-30D

SEQUENCE LISTING

<160> NUMBER OF SEQ ID NOS: 35

<210> SEQ ID NO 1
<211> LENGTH: 25
<212> TYPE: DNA
<213> ORGANISM: Artificial
<220> FEATURE:
<223> OTHER INFORMATION: Oct4 forward primer

<400> SEQUENCE: 1
gttgttttgt tttggttttg gatat                                          25

<210> SEQ ID NO 2

```
<211> LENGTH: 26
<212> TYPE: DNA
<213> ORGANISM: Artificial
<220> FEATURE:
<223> OTHER INFORMATION: Oct4 forward primer

<400> SEQUENCE: 2
atgggttgaa atattgggtt tattta                                          26

<210> SEQ ID NO 3
<211> LENGTH: 25
<212> TYPE: DNA
<213> ORGANISM: Artificial
<220> FEATURE:
<223> OTHER INFORMATION: Oct4 reverse primer

<400> SEQUENCE: 3
ccaccctcta accttaacct ctaac                                           25

<210> SEQ ID NO 4
<211> LENGTH: 24
<212> TYPE: DNA
<213> ORGANISM: Artificial
<220> FEATURE:
<223> OTHER INFORMATION: Nanog forward primer

<400> SEQUENCE: 4
gaggatgttt tttaagtttt tttt                                            24

<210> SEQ ID NO 5
<211> LENGTH: 25
<212> TYPE: DNA
<213> ORGANISM: Artificial
<220> FEATURE:
<223> OTHER INFORMATION: Nanog forward primer

<400> SEQUENCE: 5
aatgtttatg gtggattttg taggt                                           25

<210> SEQ ID NO 6
<211> LENGTH: 25
<212> TYPE: DNA
<213> ORGANISM: Artificial
<220> FEATURE:
<223> OTHER INFORMATION: Nanog reverse primer

<400> SEQUENCE: 6
cccacactca tatcaatata ataac                                           25

<210> SEQ ID NO 7
<211> LENGTH: 19
<212> TYPE: DNA
<213> ORGANISM: Artificial
<220> FEATURE:
<223> OTHER INFORMATION: Oct4 primer

<400> SEQUENCE: 7
acatcgccaa tcagcttgg                                                  19

<210> SEQ ID NO 8
<211> LENGTH: 23
<212> TYPE: DNA
<213> ORGANISM: Artificial
<220> FEATURE:
<223> OTHER INFORMATION: Oct4 primer

<400> SEQUENCE: 8
```

```
agaaccatac tcgaaccaca tcc                                              23

<210> SEQ ID NO 9
<211> LENGTH: 19
<212> TYPE: DNA
<213> ORGANISM: Artificial
<220> FEATURE:
<223> OTHER INFORMATION: c-myc primer

<400> SEQUENCE: 9
ccaccagcag cgactctga                                                   19

<210> SEQ ID NO 10
<211> LENGTH: 21
<212> TYPE: DNA
<213> ORGANISM: Artificial
<220> FEATURE:
<223> OTHER INFORMATION: c-myc primer

<400> SEQUENCE: 10
tgcctcttct ccacagacac c                                                21

<210> SEQ ID NO 11
<211> LENGTH: 20
<212> TYPE: DNA
<213> ORGANISM: Artificial
<220> FEATURE:
<223> OTHER INFORMATION: Klf4 primer

<400> SEQUENCE: 11
gcacacctgc gaactcacac                                                  20

<210> SEQ ID NO 12
<211> LENGTH: 21
<212> TYPE: DNA
<213> ORGANISM: Artificial
<220> FEATURE:
<223> OTHER INFORMATION: Klf4 primer

<400> SEQUENCE: 12
ccgtcccagt cacagtggta a                                                21

<210> SEQ ID NO 13
<211> LENGTH: 20
<212> TYPE: DNA
<213> ORGANISM: Artificial
<220> FEATURE:
<223> OTHER INFORMATION: Sox2 primer

<400> SEQUENCE: 13
acagatgcaa ccgatgcacc                                                  20

<210> SEQ ID NO 14
<211> LENGTH: 20
<212> TYPE: DNA
<213> ORGANISM: Artificial
<220> FEATURE:
<223> OTHER INFORMATION: Sox2 primer

<400> SEQUENCE: 14
tggagttgta ctgcagggcg                                                  20

<210> SEQ ID NO 15
<211> LENGTH: 22
<212> TYPE: DNA
```

```
<213> ORGANISM: Artificial
<220> FEATURE:
<223> OTHER INFORMATION: Nanog primer

<400> SEQUENCE: 15
cctccagcag atgcaagaac tc                                              22

<210> SEQ ID NO 16
<211> LENGTH: 23
<212> TYPE: DNA
<213> ORGANISM: Artificial
<220> FEATURE:
<223> OTHER INFORMATION: Nanog primer

<400> SEQUENCE: 16
cttcaaccac tggtttttct gcc                                             23

<210> SEQ ID NO 17
<211> LENGTH: 20
<212> TYPE: DNA
<213> ORGANISM: Artificial
<220> FEATURE:
<223> OTHER INFORMATION: GAPDH primer

<400> SEQUENCE: 17
ttcaccacca tggagaaggc                                                 20

<210> SEQ ID NO 18
<211> LENGTH: 18
<212> TYPE: DNA
<213> ORGANISM: Artificial
<220> FEATURE:
<223> OTHER INFORMATION: GAPDH primer

<400> SEQUENCE: 18 ccctttggc tccaccct                                                    18

<210> SEQ ID NO 19

<400> SEQUENCE: 19

000

<210> SEQ ID NO 20

<400> SEQUENCE: 20

000

<210> SEQ ID NO 21
<211> LENGTH: 57
<212> TYPE: DNA
<213> ORGANISM: Artificial
<220> FEATURE:
<223> OTHER INFORMATION: 2A peptide vector sequence

<400> SEQUENCE: 21
gccacgaact tctctctgtt aaagcaagca ggagatgttg aagaaaaccc cgggcct       57

<210> SEQ ID NO 22
<211> LENGTH: 54
<212> TYPE: DNA
<213> ORGANISM: Artificial
<220> FEATURE:
<223> OTHER INFORMATION: 2A peptide vector sequence

<400> SEQUENCE: 22
```
gagggcagag gaagtcttct aacatgcggt gacgtggagg agaatcccgg ccct        54

<210> SEQ ID NO 23
<211> LENGTH: 60
<212> TYPE: DNA
<213> ORGANISM: Artificial
<220> FEATURE:
<223> OTHER INFORMATION: 2A peptide vector sequence

<400> SEQUENCE: 23
cagtgtacta attatgctct cttgaaattg gctggagatg ttgagagcaa cccaggtccc    60

<210> SEQ ID NO 24
<211> LENGTH: 19
<212> TYPE: DNA
<213> ORGANISM: Artificial
<220> FEATURE:
<223> OTHER INFORMATION: Oct4 primer

<400> SEQUENCE: 24
acatcgccaa tcagcttgg                                                 19

<210> SEQ ID NO 25
<211> LENGTH: 23
<212> TYPE: DNA
<213> ORGANISM: Artificial
<220> FEATURE:
<223> OTHER INFORMATION: Oct4 primer

<400> SEQUENCE: 25
agaaccatac tcgaaccaca tcc                                            23

<210> SEQ ID NO 26
<211> LENGTH: 20
<212> TYPE: DNA
<213> ORGANISM: Artificial
<220> FEATURE:
<223> OTHER INFORMATION: Sox2 primer

<400> SEQUENCE: 26
acagatgcaa ccgatgcacc                                                20

<210> SEQ ID NO 27
<211> LENGTH: 20
<212> TYPE: DNA
<213> ORGANISM: Artificial
<220> FEATURE:
<223> OTHER INFORMATION: Sox2 primer

<400> SEQUENCE: 27
tggagttgta ctgcagggcg                                                20

<210> SEQ ID NO 28
<211> LENGTH: 21
<212> TYPE: DNA
<213> ORGANISM: Artificial
<220> FEATURE:
<223> OTHER INFORMATION: 4F2A primer

<400> SEQUENCE: 28
ggctggagat gttgagagca a                                              21

<210> SEQ ID NO 29
<211> LENGTH: 19
<212> TYPE: DNA

```
<213> ORGANISM: Artificial
<220> FEATURE:
<223> OTHER INFORMATION: 4F2A primer

<400> SEQUENCE: 29
aaaggaaatc cagtggcgc                                                    19

<210> SEQ ID NO 30
<211> LENGTH: 20
<212> TYPE: DNA
<213> ORGANISM: Artificial
<220> FEATURE:
<223> OTHER INFORMATION: GAPDH primer

<400> SEQUENCE: 30
ttcaccacca tggagaaggc                                                   20

<210> SEQ ID NO 31
<211> LENGTH: 18
<212> TYPE: DNA
<213> ORGANISM: Artificial
<220> FEATURE:
<223> OTHER INFORMATION: GAPDH primer

<400> SEQUENCE: 31
cccttttggc tccaccct                                                     18

<210> SEQ ID NO 32
<211> LENGTH: 25
<212> TYPE: DNA
<213> ORGANISM: Artificial
<220> FEATURE:
<223> OTHER INFORMATION: Oct4 primer

<400> SEQUENCE: 32
atttgttttt tgggtagtta aaggt                                             25

<210> SEQ ID NO 33
<211> LENGTH: 27
<212> TYPE: DNA
<213> ORGANISM: Artificial
<220> FEATURE:
<223> OTHER INFORMATION: Oct4 primer

<400> SEQUENCE: 33
ccaactatct tcatcttaat aacatcc                                           27

<210> SEQ ID NO 34
<211> LENGTH: 7
<212> TYPE: PRT
<213> ORGANISM: Artificial
<220> FEATURE:
<223> OTHER INFORMATION: Aphthovirus 2A peptide
<220> FEATURE:
<221> NAME/KEY: misc_feature
<222> LOCATION: (2)..(2)
<223> OTHER INFORMATION: Xaa can be valine or isoleucine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Asp Xaa Glu Xaa Asn Pro Gly
1               5

<210> SEQ ID NO 35
```

```
<211> LENGTH: 22
<212> TYPE: PRT
<213> ORGANISM: Artificial
<220> FEATURE:
<223> OTHER INFORMATION: Aphthovirus 2A peptide

<400> SEQUENCE: 35

Val Lys Gln Thr Leu Asn Phe Asp Leu Leu Lys Leu Ala Gly Asp Val
1               5                   10                  15

Glu Ser Asn Pro Gly Pro
            20
```

NUCLEIC ACID CONSTRUCTS ENCODING REPROGRAMMING FACTORS LINKED BY SELF-CLEAVING PEPTIDES

RELATED APPLICATIONS

This application is a national stage filing under 35 U.S.C. 371 of International Application PCT/US2009/047423, filed Jun. 15, 2009, which claims the benefit of U.S. Provisional Application No. 61/061,525, filed Jun. 13, 2008 and U.S. Provisional Application No. 61/077,068, filed Jun. 30, 2008. The entire teachings of these applications are incorporated herein by reference.

GOVERNMENT SUPPORT

The invention was supported, in whole or in part, by a grants 5-RO1-HD045022, 5-R37-CA084198 and 5-RO1-CA087869 from The National Institutes of Health. The Government has certain rights in the invention.

BACKGROUND OF THE INVENTION

Embryonic development and cellular differentiation are considered unidirectional pathways because cells undergo a progressive loss of developmental potency during cell fate specification. Two categories of pluripotent stem cells are known to date: embryonic stem cells and embryonic germ cells. Embryonic stem cells are pluripotent stem cells that are derived directly from an embryo. Embryonic germ cells are pluripotent stem cells that are derived directly from the fetal tissue of aborted fetuses. For purposes of simplicity, embryonic stem cells and embryonic germ cells will be collectively referred to as "ES" cells herein.

The generation of live animals by nuclear transfer (NT) demonstrated that the epigenetic state of somatic cells, including that of terminally differentiated cells, is labile and can be reset to an embryonic state that is capable of directing development of a new organism. The nuclear cloning technology is of potential interest for transplantation medicine but any medical application is hampered by the inefficiency of the cloning process, the lack of knowledge of the underlying mechanisms and ethical concerns. A major breakthrough in solving these issues has been the in vitro derivation of reprogrammed somatic cells (designated as "induced Pluripotent Stem" or "iPS" cells) by the ectopic expression of the four transcription factors Oct4, Sox2, c-myc and Klf4 bp Yamanaka (designated below as "reprogramming factors" or "factors") (Takahashi and Yamanaka, *Cell* 126:663-676 (2006)).

Further advancement in the area of reprogramming would be facilitated by establishing robust methods for reprogramming human somatic cells and defining effective protocols for manipulating human ES and iPS cells.

SUMMARY OF THE INVENTION

The invention relates generally to the dedifferentiation of differentiated somatic cells, to methods of generating secondary iPS cells and the secondary iPS cells produced by the methods, to chimeric animals, e.g., mice, produced from said secondary iPS cells, and to methods of screening for reprogramming agents utilizing the secondary iPS cells and chimeric animals.

In one embodiment the invention relates to a method of reprogramming a differentiated somatic cell to a pluripotent state, comprising the steps contacting a differentiated somatic cell with at least one reprogramming agent that contributes to reprogramming of said cell to a pluripotent state; maintaining said cell under conditions appropriate for proliferation of the cell and for activity of the at least one reprogramming agent for a period of time sufficient to begin reprogramming of the cell; and functionally inactivating the at least one reprogramming agent.

In another embodiment the invention relates to a method of reprogramming a differentiated somatic cell to a pluripotent state, comprising the steps of providing a differentiated somatic cell that contains at least one exogenously introduced factor that contributes to reprogramming of said cell to a pluripotent state; maintaining the cell under conditions appropriate for proliferation of the cell and for activity of the at least one exogenously introduced factor for a period of time sufficient to activate at least one endogenous pluripotency gene; and functionally inactivating the at least one exogenously introduced factor.

In a further embodiment the invention pertains to a method of selecting a differentiated somatic cell that has been reprogrammed to a pluripotent state, comprising the steps of providing a differentiated somatic cell that contains at least one exogenously introduced factor that contributes to reprogramming of the cell to a pluripotent state; maintaining the cell under conditions appropriate for proliferation of the cell and for activity of the at least one exogenously introduced factor for a period of time sufficient to activate at least one endogenous pluripotency gene; functionally inactivating the at least one exogenously introduced factor; and differentiating or distinguishing between cells which display one or more markers of pluripotency and cells which do not. In one embodiment differentiating or distinguishing between cells which display one or more markers of pluripotency and cells which do not comprises selection or enrichment for cells displaying one or more markers of pluripotency and/or selection against cells which do not display one or more markers of pluripotency.

In some embodiments of the invention the differentiated somatic cell is partially differentiated. In other embodiments of the invention the differentiated somatic cell is fully differentiated.

In some embodiments of the invention the differentiated somatic cell is cell of hematopoetic lineage or is a mesenchymal stem cell; in some embodiments the differentiated somatic cell is obtained from peripheral blood. In one embodiment of the invention the differentiated somatic cell is an immune system cell. In one embodiment the differentiated somatic cell is a macrophage. In one embodiment the differentiated somatic cell is a lymphoid cell. In other embodiments of the invention the differentiated somatic cell is a B cell, such as an immature (e.g., pro-B cell or pre-B cell) or mature (e.g., non-naïve) B-cell. In still other embodiments the differentiated cell is a neural progenitor cell, an adrenal gland cell, a keratinocyte, a muscle cell, or an intestinal epithelium cell.

In some embodiments of the invention the at least one exogenously introduced factor is a polynucleotide. In other embodiments the at least one exogenously introduced factor is a polypeptide. In one embodiment the at least one exogenously introduced factor is selected from the group consisting of Oct4, Sox2, Klf-4, Nanog, Lin28, c-Myc and combinations thereof. In particular embodiments of the invention the differentiated somatic cell contains exogenously introduced Oct4, Sox2, and Klf-4 exogenously introduced Oct4, Sox2, Klf-4 and c-Myc.

In one embodiment of the invention the at least one exogenously introduced factor is selected from the group consisting of Oct4, Sox2, Klf-4, c-Myc and combinations thereof and the differentiated somatic cell further contains at least one exogenously introduced factor (e.g., a polynucleotide or polypeptide) capable of inducing dedifferentiation of the differentiated somatic cell. In some embodiments the factor capable of inducing dedifferentiation of said differentiated somatic cell is selected from the group consisting of at least one polynucleotide which downregulates B cell late specific markers, at least one polynucleotide which inhibits expression of Pax5, at least one polypeptide which downregulates B cell late specific markers, at least one polypeptide which inhibits expression of Pax5, and combinations thereof. In one embodiment of the invention the factor capable of inducing dedifferentiation of said differentiated somatic cell is C/EBPα or a human homolog of C/EBPα.

In particular embodiments of the invention the at least one exogenously introduced factor is introduced using a vector, e.g., an inducible vector or a conditionally expressed vector. In one aspect the at least one exogenously introduced factor is introduced using a vector which is not subject to methylation-mediated silencing. In yet another embodiment the at least one exogenously introduced factor is introduced using a viral vector such as a retroviral or lentiviral vector.

The present invention also provides methods for producing a cloned animal. In the methods, a somatic cell is isolated from an animal having desired characteristics, and reprogrammed using the methods of the invention to produce one or more reprogrammed pluripotent somatic cell ("RPSC"). The RPSCs are then inserted into a recipient embryo, and the resulting embryo is cultured to produce an embryo of suitable size for implantation into a recipient female, which is then transferred into a recipient female to produce a pregnant female. The pregnant female is maintained under conditions appropriate for carrying the embryo to term to produce chimeric animal progeny. The chimeric animal can further be mated to a wild type animal as desired. The invention further relates to a chimeric animal, e.g., a chimeric mouse, produced by the methods of the invention.

The invention further relates to an isolated pluripotent cell produced by a method comprising (a) providing a differentiated somatic cell that contains at least one exogenously introduced factor that contributes to reprogramming of said cell to a pluripotent state; (b) maintaining said cell under conditions appropriate for proliferation of said cell and for activity of said at least one exogenously introduced factor for a period of time sufficient to activate at least one endogenous pluripotency gene; (c) functionally inactivating said at least one exogenously introduced factor; and (d) differentiating cells which display one or more markers of pluripotency from cells which do not.

The invention also relates to a purified population of somatic cells comprising at least 70% pluripotent cells derived from reprogrammed differentiated somatic cells produced by a method comprising (a) providing a differentiated somatic cell that contains at least one exogenously introduced factor that contributes to reprogramming of said cell to a pluripotent state; (b) maintaining said cell under conditions appropriate for proliferation of said cell and for activity of said at least one exogenously introduced factor for a period of time sufficient begin reprogramming of said cell or to activate at least one endogenous pluripotency gene; (c) functionally inactivating said at least one exogenously introduced factor; and (d) differentiating cells which display one or more markers of pluripotency and cells which do not.

In another aspect the invention relates to a method of producing a pluripotent cell from a somatic cell, comprising the steps of (a) providing one or more somatic cells that each contain at least one exogenously introduced factor that contributes to reprogramming of said cell to a pluripotent state, wherein said exogenously introduced factor is introduced using an inducible vector which is not subject to methylation-induced silencing; (b) maintaining said one or more cells under conditions appropriate for proliferation of said cells and for activity of said at least one exogenously introduced factor for a period of time sufficient begin reprogramming of said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor for a period of time sufficient to begin reprogramming said cell or to activate at least one endogenous pluripotency gene; and (h) differentiating between cells which display one or more markers of pluripotency and cells which do not. In a particular embodiment the method yields a purified population of somatic cells comprising at least 70% pluripotent cells derived from reprogrammed differentiated somatic cells The invention also relates to an isolated pluripotent cell produced by a method comprising (a) providing one or more somatic cells that each contain at least one exogenously introduced factor that contributes to reprogramming of said cell to a pluripotent state, wherein said exogenously introduced factor is introduced using an inducible vector which is not subject to methylation-induced silencing; (b) maintaining said one or more cells under conditions appropriate for proliferation of said cells and for activity of said at least one exogenously introduced factor for a period of time sufficient to begin reprogramming said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor for a period of time sufficient to activate at least one endogenous pluripotency gene; and (h) differentiating cells which display one or more markers of pluripotency and cells which do not.

In preferred embodiments of the invention the methods yield a purified population of somatic cells comprising at least 70% (e.g., 70%, 75%, 80%, 85%, 90%, 95%, 99%) pluripotent cells derived from reprogrammed differentiated somatic cells. In particular embodiments the pluripotent cells are genetically homogenous.

The invention also relates to a method of identifying a reprogramming agent comprising (a) providing one or more somatic cells that each contain at least one exogenously introduced factor that contributes to reprogramming of said cell to a pluripotent state, wherein each of said exogenously introduced factors is introduced using an inducible vector which is not subject to methylation-induced silencing and the expression of which is controlled by regulatory elements induced by distinct inducers; (b) maintaining said one or more cells under conditions appropriate for proliferation of said cells and for activity of said at least one exogenously introduced factor for a period of time sufficient to reprogram said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor wherein activity of said at least one exogenously introduced factor is insufficient by itself to activate at least one endogenous pluripotency gene; (h) contacting the somatic cell of (g) with one or more candidate reprogramming agents; and (i) identifying cells contacted with said one or more candidate reprogramming agents which display one or more markers of pluripotency, wherein candidate reprogramming agents which induce the somatic cell of (g) to display one or more markers of pluripotency are identified as reprogramming agents.

The invention also relates to methods utilizing known inducible promoter systems. As one example, inducible vectors, e.g., DOX and tamoxifen inducible lentiviral vectors, are encompassed. DOX inducible retroviral vectors have been important to define the sequential activation of pluripotency markers and the minimum time of vector expression during reprogramming of somatic mouse cells. As described herein we have generated inducible lentiviral vectors that will allow the temporally restricted expression of the reprogramming factors. Following the same strategy as used for murine genes, we have generated lentiviral vectors that transduce the human OCT4, SOX2, KLF4 and C-MYC c-DNAs either constitutively or under the control of a DOX inducible promoter. To generate a DOX inducible system we infected human fibroblasts with a lentiviral vector carrying the rtTA transactivator.

To enable independent inducible control of vectors we also generated OCT4, SOX2 and C-MYC estrogen receptor (ER) fusion constructs by fusing the factors to the estrogen ligand binding domain to allow for tamoxifen dependent expression. Addition of tamoxifen to cells transduced with a SOX2-ER fusion construct leads to translocation of the SOX2 protein from the cytoplasm to the nucleus as expected for drug induced activation. These results show that the DOX and ER fusion inducible systems can be used to independently control the expression of transduced factors.

One embodiment of the invention relates to the use of multiple, e.g., two, different regulatable systems, each controlling expression of a subset of the factors. For example, one might place 3 of the factors under control of a first inducible (e.g., dox-inducible) promoter and the 4th factor under control of a second inducible (e.g., tamoxifen-inducible) promoter. Then, one could generate an iPS cell by inducing expression from both promoters, generate a mouse from this iPS cell, and isolate fibroblasts (or any other cell type) from the mouse. These fibroblasts would be genetically homogenous and would be reprogrammable without need for viral infection. One would then attempt to reprogram the fibroblasts under conditions in which only the first promoter is active, in the presence of different small molecules that could potentially substitute for the 4th factor, in order to identify small molecule "reprogramming agents" or optimize transient transfection or other protocols for introducing the 4th factor. A number of variations are possible; for example, one might stably induce expression of 3 factors and transiently induce expression of the 4th factor, etc. Any combination of factors can be assessed using the described methods. Also, one can modulate expression levels of the factors by using different concentrations of inducing agent.

Another approach is to place the gene that encodes one of the factors between sites for a recombinase and then induce expression of the recombinase to turn off expression of that factor. For example, a heterologous sequence could be positioned between the promoter and the coding sequence, wherein the heterologous sequence is located between sites for a recombinase; the heterologous sequence prevents expression. A recombinase is introduced into the cells (e.g., by introducing an expression vector that encodes the recombinase, e.g., Adenovirus-Cre) and causes excision of the heterologous sequence, thereby allowing expression of the transgene. Also, transgenes can be integrated at a variety of non-essential loci (e.g., loci whose disruption doesn't significantly affect development, exemplified by Collagen I or Rosa26 loci).

These systems are useful, e.g., for identifying reprogramming agents and studying the requirements and events that occur in reprogramming (including discovering cell-type specific differences).

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D illustrate the generation of genetically homogenous cell cultures for epigenetic reprogramming FIG. 1A shows a scheme for infection of puromycin-resistant, Nanog-GFP or Nanog-neo primary MEFs expressing the reverse tetracycline transactivator (M2rtTA) with dox-inducible lentiviruses encoding the 4 reprogramming factors followed by induction of reprogramming, primary iPS colony selection, dox withdrawal, chimera formation, and puromycin selection for iPS-derived secondary somatic cells. FIG. 1B illustrates that NNeo secondary MEFs isolated from chimeras undergo complete epigenetic reprogramming. Dox-independent cultures express the pluripotency-associated genes alkaline phosphatase, SSEA1, and Nanog. FIG. 1C shows that MEF-derived NNeo and NGFP2 secondary iPS cells generate cells of all three germ layers in teratoma formation assays, and contribute to chimera formation when injected into blastocysts, as indicated by the presence of iPS-derived agouti coat color on a black background (FIG. 1D).

As shown in FIG. 2A, secondary MEFs from three 'primary' iPS cell lines were treated with dox and reprogramming was monitored visually. The different MEF populations exhibited morphologic differences 6 days after dox administration, but all formed colonies with ES cell morphology within 12 days (arrows). FIG. 2B shows that neomycin resistant and alkaline phosphate positive colonies were present in NNeo cultures when the drug was added to the media as early as day 4 after dox induction. FIG. 2C illustrates flow cytometric analysis for reactivation of SSEA1 and the Nanog-GFP reporter allele (in NGFP2 and NGFP3 lines) over 18 days of dox culture. As shown in FIG. 2D secondary NGFP2 MEFs were plated at densities varying from 0.025-500 cells/mm$^2$ followed by dox addition. GFP+ colonies were counted 4 weeks later. As shown in FIG. 2E, single secondary MEFs were plated in 96 well plates containing a γ-irradiated MEF feeder layer followed by dox induction. The percentage of single cells able to proliferate sufficiently to form a visible colony on the MEF feeder layer (light grey bars) and the percentage of single cells able to form GFP+ or Neo resistant secondary iPS colonies (dark grey bars) were scored 4 weeks later.

FIG. 3A shows quantitative RT-PCR examining induction of expression of the 4 reprogramming factors in response to 72 hours of dox treatment, relative to Gapdh levels. FIG. 3B shows immunofluorescence detection of Oct4 and Sox2 in secondary MEF cultures 72 hours after dox induction. As shown in FIG. 3C, NGFP2 secondary MEFs were cultured in the presence of dox for the indicated time (5-22 days, red bars) followed by dox withdrawal. Cultures were monitored daily for the first instance of GFP activation (green bars). Blue bars indicate periods in which GFP+ colonies appeared during dox treatment. FIG. 3D shows that NGFP2 MEFs were cultured in the presence of dox for 10-15 days, at which point dox was withdrawn, and GFP+ colonies were scored at day 34. As illustrated in FIG. 3E NGFP2 MEFs were cultured in the presence of dox for either 9 (blue) or 22 days (red line), and the appearance of GFP+ colonies was scored daily until day 29. Note the appearance of GFP-positive colonies as late as 15 days after dox withdrawal (blue line). As illustrated in FIG. 3F, NGFP3 secondary MEFs were cultured in the presence or absence of dox, dox+5-Aza, or dox+TSA, and GFP+ colonies were scored 3 weeks later.

As shown in FIG. 4A, NNeo secondary intestinal epithelial crypt-villus structures were isolated from chimeras, and after 24 hours of culture in the presence of dox, spheroids began appearing in suspension (FIG. 4B, inset). FIG. 4C illustrates that within 72 hours of dox culture, suspended spheroids attached to the γ-irradiated feeder layer and took on ES-like morphology. As shown in FIG. 4D, colonies continued to grow during two weeks of dox treatment, but differentiated and became indistinguishable from the feeder layer upon dox withdrawal (FIG. 4E). FIG. 4F shows that sox-dependent intestinal epithelial colonies were neomycin resistant two weeks after dox administration. FIG. 4G shows bisulfite sequencing of the endogenous Oct4 and Nanog promoters in freshly isolated NNeo secondary intestinal epithelium, partially reprogrammed dox dependent cells, fully reprogrammed NNeo iPS cells after infection with Sox2 and Klf4 viruses. As shown in FIG. 4H, qRT-PCR analyses of expression of the 4 factors and Nanog revealed that dox-dependent NNeo intestinal epithelial colonies express high levels of Oct4 and cMyc in comparison with ES cells, but very low amounts of Sox2 and Klf4. FIG. 4I shows that NGFP2 secondary intestinal epithelial cells formed spheroids in suspension within 24 hours of dox addition and took on ES-like morphology within 72 hours (FIG. 4J). FIGS. 4K and 4L illustrates that NGFP2 intestinal epithelium gave rise to dox-independent secondary iPS colonies that express GFP from the endogenous Nanog locus. As shown in FIG. 4M, EDTA-DTT based fractionation of intestinal villi from differentiated cells of the tip (fraction 1) to the progenitor cells of the crypt (fraction 7)[28] followed by 4 days dox induction demonstrates that crypt fractions in both NNeo and NGFP2 secondary lines are more efficient at initial colony formation. As shown in FIG. 4N, qRT-PCR analysis showed that with the exception of Klf4, the transgenes were more efficiently induced in fraction 7 (crypt) than in fraction 1 (villus tip) of the NNeo and NGFP2 intestinal epithelial cells.

FIGS. 5A and 5B show NNeo mesenchymal stem cells (MSCs) before and after 3 weeks of dox administration. FIGS. 5C and 5D show NGFP2 MSCs before and after 10 days of dox treatment forming ES-like colonies. FIGS. 5E and 5F show that NGFP2 MSCs gave rise to dox-independent iPS colonies that express GFP from the endogenous Nanog locus. As shown in FIG. 5G, colonies of dermal keratinocytes from NNeo chimeras with typical epithelial morphology (inset) began to exhibit ES cell morphology within 12 days of dox treatment (FIG. 5H). These cells fully reprogrammed to form neomycin resistant secondary iPS colonies (FIG. 5I). As illustrated in FIG. 5J, after expansion in serum-free media, plated NNeo-derived neurospheres readily differentiated into astrocytic cells in response to dox and serum-containing ES cell media. When plated neurosphere cells were expanded in adherent conditions with EGF and FGF2 for another 3 weeks and then exposed to dox-containing media iPS cell-like colonies appeared both in ES cell (FIG. 5K) and serum-free media (FIG. 5L).

FIG. 7A shows qRT-PCR analysis of endogenous Oct4, Sox2, Klf4, and c-Myc transcripts in NGFP2 MEFs during the time course of reprogramming in response to dox treatment. Also shown are expression levels in two ES cell RNA preparations (V6.5 line) and the NGFP2 iPS cell line. FIG. 7B shows a comparison of the interexperimental variability in iPS colony formation efficiency between direct infection and the secondary system. $3\times10^5$ Oct4-neo MEFs[1] were infected with the 4 factors encoded by Moloney-based retroviral vectors on a 10 cm plate, neomycin selection was initiated on day 6, and resistant colonies were counted on day 20 (left—direct infection). $3\times10^4$ secondary NGFP2 MEFs were plated in a 6 well dish, exposed to dox-containing media, and GFP-positive colonies were counted 3 weeks later (right—secondary system). The bars represent colony numbers in each of the 4 independent experiments. FIG. 7C shows Southern analysis of secondary iPS lines NGFP3, NGFP2, and NNeo with Klf4, c-Myc, Sox2, and Oct4 cDNA probes. Endogenous bands are marked with an arrow, and proviral insertions are marked with an arrowhead, with the exception of Oct4 in the NNeo line, which is a transgene targeted to the collagen I locus.

FIG. 8A shows NGFP2 secondary tail tip fibroblasts successfully reprogrammed into dox-independent, GFP+iPS cells. FIG. 8B shows that iPS cells derived from NGFP2 secondary intestinal epithelium express endogenous Nanog and SSEA1. FIG. 8C shows that iPS cells derived from NGFP2 secondary mesenchymal stem cells express endogenous Nanog and SSEA1. As shown in FIG. 8D, primary mesenchymal stem cells harboring the reverse tetracycline transactivator at the Rosa 26 locus and the Oct4 coding sequence under control of the Tet-operator 16 were infected with viruses encoding Sox2, c-Myc, and Klf4. Addition of dox to the infected MSCs resulted in fully reprogrammed, dox-independent iPS cells that express endogenous Nanog protein (immunofluorescence).

FIG. 9F shows secondary intestinal epithelium isolated from NNeo chimeras and cultured in the presence of dox for 8, 10, or 12 days and stained for alkaline phosphatase activity. As shown in FIG. 9G, NNeo secondary intestinal epithelial cells became doxindependent iPS cells after infection with additional Sox2 and Klf4 viruses. Immunofluorescence analysis (red, top row) revealed expression of Oct4, Sox2, Nanog, and SSEA1 in fully reprogrammed cells (blue, bottom row represents the nuclear DAPI stain).

As shown in FIG. 11A, human fibroblasts were infected with lentivirus vectors carrying DOX inducible factors (Brambrink et al., *Cell Stem Cell, February* 7, 2(2):151-159 (2008)). When DOX was added to the cultures, analysis by qPCR detected strong factor expression, whereas little if any transcript was seen in the absence of DOX. Also, iPS cells derived from the infected fibroblasts displayed DOX dependent expression (right two panels). As shown in FIG. 11B, fibroblasts were infected with vectors containing a SOX2-ER fusion construct. Tamoxifen addition to the medium resulted in translocation of the cytoplasmic protein to the nucleus indicating drug dependent protein activation.

As shown in FIG. 12A, OCT4 and NANOG expression was quantitated by qPCR and shown to be in a similar range as in control huES cells. FIG. 12B shows examples of iPS cells generated from adult human fibroblasts. The human iPS cells formed tight colonies and stained for SSEA4, TRA 160 and OCT4. FIG. 12C shows teratomas with differentiated cell types formed after injection of the iPS cells into SCID mice.

FIGS. 13A-13C show reprogramming of mouse fibroblasts after transduction of the four factors via a polycistronic retroviral vector. FIG. 13A shows a schematic illustration of vectors carrying the four transcription factors Sox2, Oct4, Klf4 and c-myc, each separated by 2A sequences or various combinations of 3 or 2 factors. As shown in FIG. 13B, fibroblasts were co-infected with the 4 factor polycistronic vector shown in the upper part of the panel and a single Oct4 virus. Reprogrammed iPS cells expressed alkaline phosphatase (AP), SSEA1, Nanog and Oct4. FIG. 13C shows the results of Southern blot analysis for proviral integrations of 3 independent iPS lines. The DNA was digested with Spe1 which cleaves once in the PBS of the vector (giving 1 band per provirus) and the blots were sequentially probed with a Sox2, Klf4, c-myc and Oct4 probe. Lines 4FO#5 and #9 carried one and line 4FO#14 two polycistronic vectors (one of the latter was truncated and had lost the 5' cMYC sequences). However, hybridization with an Oct4 probe revealed between 8 and 11 additional Oct4 proviruses.

FIG. 14A shows FUW lentivirus constructs tested by transient transfection (also shown in the previous figure). In total four 2A peptides (F2A, T2A, E2A, and P2A) were used. FIG. 14B shows transient transfection of 293 cells with FUW 2A lentiviruses. Cells were harvested after 48 hours and analyzed by western blot (WB). Efficient protein expression was observed in all constructs tested, indicating four unique 2A peptides support robust protein expression. NOTE: Sox2 protein is not detected in ES cells because only a short exposure was used. FIG. 14C shows a schematic of the 4F2A DOX-inducible lentivirus containing three types of 2A peptides (P2A, T2A, and E2A). Murine cDNAs for Oct4, Sox2, Klf4, and c-Myc. This particular sequence of factors and 2A peptides is subsequently referred to as "4F2A. " FIG. 14 D shows RT-PCR analysis of mRNA induction in cells transduced with OSKM 4F2A+rtTA for 3-days. Total Oct4 or Sox2 induction was used to test levels of 4F2A induction relative to ES cells. E2A-cMyc primers were used to detect viral-specific transcripts. Error bars represent s.d. of the mean of triplicate reactions. FIG. 14E shows the results of Western blot analysis of MEFs transduced with 4F2A+rtTA for three days. Cells infected with 4F2A DOX-inducible lentivirus+rtTA produce all four reprogramming factors upon addition of doxycycline, DOX.

As shown in FIG. 15A, immunostaining of Oct4 protein indicates high titre infections can be achieved with the 4F2A. MEFs were cultured in DOX media for 2 days after transduction with 4F2A+rtTA. FIG. 15B illustrates morphology changes in NanogGFP-MEFs transduced with 4F2A+rtTA cultured in ES media+DOX. Colonies appeared ~8 days similar to cells infected with single viruses. Nanog GFP+ colonies were observed by day 25 after DOX media removal at day 20. Two columns show typical colonies observed on the plate. FIG. 15C shows 4F2A iPS lines generated from Nanog-GFP MEFs or 14-week tail-tip fibroblasts (TTFs) that stain positive for pluripotency markers AP, SSEA1, Oct4 and have reactivated the endogenous Nanog locus (GFP+ for MEFs and by immunostaining for TTF).

FIG. 16A shows in vivo differentiation of 4F2A MEF-iPS lines #1,2, and 4. Histological analysis of teratomas induced after subcutaneous injection into SCID mice indicates iPS lines contribute to all three germ layers. FIG. 16B shows moderate to high contribution postnatal chimeric mice as detected by agouti coat color from 4F2A iPS line #4. FIG. 16C shows the results of Southern blot analysis of 4F2A proviral integrations in MEF-iPS cell lines #1-4. iPS cell DNA was digested with BamHI. Hybridization of the same molecular weight fragment using all four probes indicates presence of 4F2A provirus. Red arrow highlights iPS line #4 which contained one proviral copy of the 4F2A. * indicates endogenous allele.

FIGS. 17A-17E show generation of human iPS lines using a single 4F2A polycistronic virus. FIG. 17A shows Neonatal human foreskin keritinocytes (NHFK) transduced with 4F2A (carrying mouse cDNAs)+rtTA. On day 22 a single colony was picked and expanded, giving rise to colonies resembling hES colonies. These colonies were picked and a stable hiPS line was established. FIG. 17B shows Ker hiPS #1.1 immunostaining for pluripotency markers AP, Oct4, Nanog, SSEA-4, Tra1-60, and Tra1-81. DAPI stain is in lower panels. FIG. 17C illustrates that-karyotype of Ker hiPS #1.1 is normal 46 XY. FIG. 17D shows in vivo differentiation of Ker hiPS #1.1. Hematoxylin and eosin staining of teratoma sections generated by Ker hiPS #1.1. FIG. 17E shows in vitro differentiation of Ker hiPS #1.1. (Left) Ker-iPS #1.1-derived neural precursors exposed to differentiation conditions for 6 days produce terminally differentiated neurons as detected by anti-Tuj1 immunostaining (green). (Right) Ker-iPS #1.1 neural precursors (NPs) undergo spontaneous differentiation. NPs were detected by anti-Nestin immunostaining and differentiated neurons by anti-Tuj1 (red). DAPI stain for DNA in both pictures is blue.

FIG. 18A shows Southern blot analysis of 4F2A MEF iPS lines. A second digest was performed (XbaI) to confirm the proviral copy number. In this digest iPS line #2 and #4 show 1 proviral copy, however only #4 had 1 proviral copy in both digests. FIG. 18B shows Dox-withdrawl after 8 days post-infection of Nanog GFP MEFs with rtTA+OSKM generated two iPS lines. Both generated stable iPS lines after 1-2 passages.

FIG. 20A shows infection efficiency from two experiments as detected by Oct4 immunostaining in Keratinocytes infected with 4F2A+rtTA and cultured in hES media+DOX for 48 hours. Efficiency of infection was ~10-20% based on fraction of cells positive for Oct4 protein. FIG. 20B shows human iPS lines stain positive for pluripotency markers expressed in hES cells (Ker iPS #3 is shown).

FIG. 21A shows Southern blot analysis of Ker-iPS lines. 10 mg of genomic DNA was harvested and digested with XbaI. Hybridization of the same molecular weight fragment indicates presence of 4F2A provirus. Probes for Sox2, Klf4, and c-Myc suggested 2 (#1.1) and 1 (#3) proviral copies. Common bands observed between the two iPS lines are not viral integration as these were derived from independent infections. FIG. 21B shows Southern blot analysis of Ker-iPS lines. 10 mg of genomic DNA was harvested and digested with BamHI. Hybridization of the same molecular weight fragment indicates presence of 4F2A provirus. Probes for Oct4 and c-Myc indicate 3 (#1.1) and 2 (#3) proviral copies.

As illustrated in FIG. 23A "primary" fibroblasts carrying GFP in the OCT4 locus were transduced with all four factors using DOX inducible vectors as well as a vector carrying the tet rtTA transactivator, and "primary" iPS cells were generated after DOX induction. The cells were differentiated in the absence of DOX to "secondary" fibroblasts carrying the same combination of vectors that had allowed the derivation of the primary iPS cells. As shown in FIG. 23B, reprogramming the secondary fibroblasts to secondary iPS cells requires only DOX induction of the proviruses instead of infection with new viruses.

FIG. 27A shows phase contrast picture and immunofluorescence staining of hiPSC lines $M^{3F}$-1 (non-PD hiPSCs), $PDA^{3F}$-1, $PDB^{3F}$-5, $PDC^{3F}$-1, $PDD^{3F}$-1, and $PDE^{3F}$-3 for pluripotency markers SSEA4, Tra-1-60, OCT4, SOX2 and NANOG. FIG. 28A shows quantitative RT-PCR for the reactivation of the endogenous pluripotency related genes NANOG, OCT4 and SOX2 in independent hiPSC lines, hESCs and primary fibroblasts. Relative expression levels were normalized to expression of these genes in fibroblasts.

FIGS. 28A-28C illustrate that PD patient-derived hiPSCs carry low copy numbers of viral integrations. FIG. 28A shows hematoxylin and eosin staining of teratoma sections generated from hiPSC lines A6 (non-PD hiPSCs), $PDA^{3F}$-1, $PDB^{3F}$-1, $PDC^{3F}$-1, $PDD^{3F}$-1, and $PDE^{3F}$-3 showing: Top row panels: pigmented neural epithelium; 2nd row panels: neural rosettes; 3rd row panels: intestinal epithelium; 4th row panels: bone/cartilage; bottom row panels: smooth muscle. FIG. 28B shows the results of Southern blot analysis of hESC line BG01, mouse embryonic fibroblast (MEF) feeder cells and the indicated PD patient-derived hiPSCs (and non-PD hiPSC line $M^{3F}$-1) for proviral integrations of XbaI digested genomic DNA using 32P-labelled DNA probes against OCT4, KLF4, SOX2 and c-MYC. FIG. 28C is a table summarizing the approximate number of proviral integrations for the four reprogramming factors in hiPSCs based on Southern blot analysis shown in 28B.

FIGS. 29A-29C show generation of PD patient-derived hiPSCs using loxP excisable reprogramming factors. FIG. 29A is a schematic drawing of the DOX-inducible lentiviral construct FUW-tetO-loxP, the genomic locus after proviral integration (2lox) and after Cre-recombinase mediated excision (1lox). The FUW-TetO-loxP vector contains a tetracycline response element (TRE) located 5' of a minimal CMV promoter and a unique MfeI site used for diagnostic Southern blot digests. The reprogramming factors are flanked by EcoRI restriction sites. The 3' LTR of this lentiviral vector contains a single loxP site, which is duplicated during proviral replication into the 5'LTR. This duplication results in a transgene flanked by 2 loxP sites after genomic integration of the provirus (2lox). This allows the excision of the transgene in combination with the complete promoter sequences using Cre-recombinase (1lox). (WRE=Woodchuck Response Element). FIG. 29B shows phase contrast picture and immunofluorescence staining of hiPSC lines PDB$^{2lox}$-17 and PDB-21 for pluripotency markers SSEA4, Tra-1-60, OCT4, SOX2 and NANOG. PDB$^{2lox}$-17 and PDB$^{2lox}$-21 were derived by expression of the three reprogramming factors OCT4, SOX2 and KLF4 from the FUW-tetO-loxP virus shown in A. In these cells all three reprogramming factors are flanked by loxP sites at their genomic integration site. FIG. 29C shows hematoxylin and eosin staining of a teratoma section generated from PDB$^{2lox}$-17 and PDB$^{2lox}$-21 cells carrying excisable reprogramming factors.

FIGS. 30A-30D show generation and characterization of reprogramming factor-free hiPSCs. FIG. 30A is a schematic overview of Cre-mediated excision of the transgenes to generate reprogramming factor free hiPSCs. IPS PDB$^{2lox}$ cells were derived using FUW-tetO-loxP lentiviral vectors transducing 3 reprogramming factors OCT4, KLF4 and SOX2. FIG. 30B shows Southern blot analysis for proviral integrations of parental fibroblasts (PDB), provirus-carrying PDB$^{2lox}$ clones (PDB$^{2lox}$-17 and PDB$^{2lox}$-21) and the indicated PDB$^{1lox}$ clones after Cre-recombinase mediated excision of the transgenes. Puro indicates PDB$^{1lox}$ clones, which were isolated by puromycin selection; GFP indicates PDB$^{1lox}$ clones isolated by FACS sorting for EGFP (as shown in 30A). Genomic DNA was digested with XbaI and probed for proviral integrations using $^{32}$P-labelled DNA probes against OCT4, KLF4, and SOX2. PDB$^{1lox}$ clones indicated in blue were disregarded because of remaining transgene integrations based on the MfeI digest shown in FIG. 34. FIG. 30C shows cytogenetic analysis of hiPSC lines PDB$^{1lox}$-17Puro-5, and PDB$^{1lox}$-21 Puro-12 shows normal karyotype after Cre-mediated excision of the transgenes. FIG. 30D is a summary of the generation of factor-free hiPSCs.

FIG. 31A shows phase contrast picture and immunofluorescence staining of reprogramming factor-free hiPSC lines PDB$^{1lox}$-17Puro-5 and PDB$^{1lox}$-21Puro-12 for pluripotency markers SSEA4, Tra-1-60, OCT4, SOX2 and NANOG. FIG. 31B shows quantitative RT-PCR for the reactivation of the endogenous pluripotency related genes NANOG, OCT4 and SOX2 in hESCs, fibroblasts (PDB), provirus-carrying PDB$^{2lox}$ clones (PDB$^{2lox}$-17 and PDB$^{2lox}$-21) and indicated PDB$^{1lox}$ clones after Cre-recombinase mediated excision of the transgenes. Relative expression levels were normalized to expression of these genes in fibroblasts. FIG. 31C shows hematoxylin and eosin staining of a teratoma sections generated from factor-free PDB$^{1lox}$-17puro-5 and PDB$^{1lox}$-21puro-26 cells. FIG. 31D shows quantitative RT-PCR for residual transgene expression of OCT4, KLF4 and SOX2 in hESCs (BG01), primary fibroblasts (PDB), primary infected fibroblasts (PDD$^{3F}$+/−DOX), hiPSCs (M3$^{F3}$-1), PD-derived hiPSCs (PDA$^{3F}$-1, PDB$^{3F}$-5, PDC$^{3F}$-1, PDD$^{3F}$-1, PDE$^{3F}$-3), provirus carrying PDB$^{2lox}$ clones (PDB$^{2lox}$-17 and PDB$^{2lox}$-21) and the reprogramming factor free PDB$^{1lox}$ clones (PDB$^{1lox}$-17Puro-5, PDB$^{1lox}$-17Puro-31, PDB$^{1lox}$-21Puro-12, PDB$^{1lox}$-21Puro-20). Relative expression levels are normalized to DOX-induced expression in primary infected fibroblasts. FIG. 31E is a Venn diagram displaying the number of differentially expressed genes (p<0.05 determined by moderated t-test, corrected for false discovery rate) between provirus-carrying PDB$^{2lox}$ lines (PDB$^{2lox}$-5, PDB$^{2lox}$-17, PDB$^{2lox}$-21, PDB$^{2lox}$-22) compared to hESCs (H9, BG01) or reprogramming factor-free PDB$^{lox}$ lines (PDB$^{1lox}$-17Puro-5, PDB$^{1lox}$-17Puro-10, PDB$^{1lox}$-21Puro-20, PDB$^{1lox}$-21Puro-26) compared to hESCs (H9, BG01) respectively.

FIG. 32A shows Immunofluorescence staining of primary fibroblasts (PDB) transduced with the 4 reprogramming factors OCT4, KLF4, SOX2 and c-MYC. Cells were fixed and stained for the expression of NANOG (red) and Tra-1-60 (green) at different time points (top panel at day 8; bottom panel at day 10) after DOX-induced transgene expression. No NANOG/Tra-1-60 positive cells were detected earlier than 8 days or in cultures that were not treated with DOX. NANOG and Tra-1-60 colonies were also detectable in all cultures that were stained at later time points (12, 14, 16, 18, 20 days). FIG. 32B shows immunofluorescence staining for pluripotency related markers SSEA4, TRA-1-60, OCT4, SOX2 and NANOG of hiPSC clones PDB$^{4F}$-1 and PDB$^{3F}$-12d. To determine the temporal requirement for transgene expression, primary fibroblasts (PDB) were infected with DOX-inducible lentiviruses carrying the reprogramming factors. Transgene expression was induced by the addition of DOX. At different time points the medium was changed to hESC medium without DOX and iPSCs were isolated at 24 days after initial DOX addition. The left panel shows hiPSC clone PDB$^{4F}$-1 that was isolated from a culture that was transduced with the four reprogramming factors and exposed to DOX for 8 days. The right panel shows the hiPSC clone PDB$^{3F}$-12d that was isolated from a culture that was transduced with the three reprogramming factors and exposed to DOX for 12 days. FIG. 32C shows quantitative RT-PCR for the reactivation of the endogenous pluripotency related genes NANOG, OCT4 and SOX2 in the following lines: hiPSC lines PDB$^{4F}$-1 and PDB$^{4F}$-2, D4, A6, hESCs and primary fibroblasts. Relative expression levels were normalized to expression of these genes in fibroblasts. PDB$^{4F}$-1 and PDB$^{4F}$-2 iPSCs were isolated after 8 days of transgene expression of the four reprogramming factors OCT4, SOX2, KLF4 and c-MYC.

FIG. 32D shows hematoxylin and eosin staining of teratoma sections generated from hiPSC line PDB$^{3F}$-12d and PDB$^{4F}$-2. PDB$^{3F}$-12d was derived by DOX-induced transgene expression of the three reprogramming factors OCT4, SOX2, KLF4 for 12 days. PDB$^{4F}$-2 was derived by DOX-induced transgene expression of the four reprogramming factors OCT4, SOX2, KLF4 and c-MYC for 8 days.

Figures 2A, 2B, 2C, 2D, 2E:
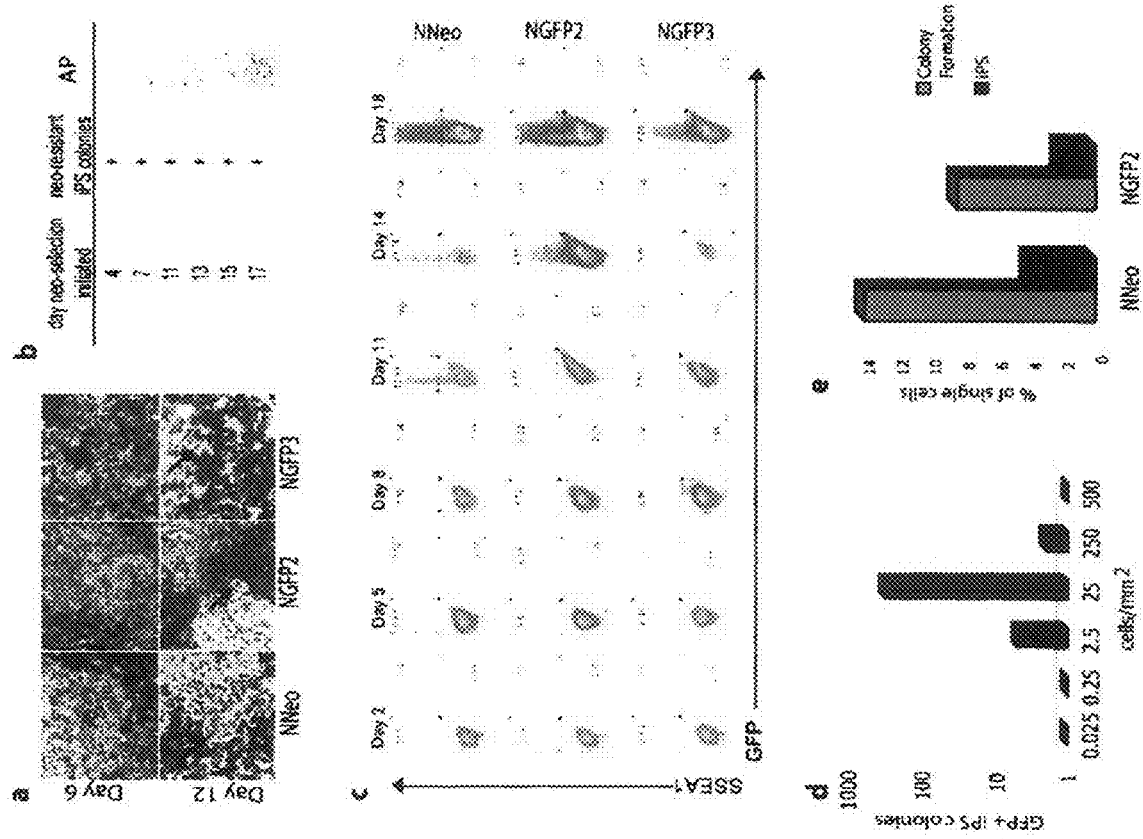
FIGS. 2A-2E illustrate that reprogramming kinetics and efficiencies vary between MEFs from distinct iPS cell lines.

Table 1: Human iPS cells derived from factor transduced embryonic or adult human fibroblasts. Fibroblasts were infected with constitutive or DOX inducible Lenti virus vectors transducing different combinations of factors. Between 50 and 100 clones were picked in each experiment. Southern blots for viral integrations showed that the iPS lines were derived from independently infected fibroblasts. (O=OCT4, S=SOX2, K=KLF4, M=C-MYC, L=LIN28, N=NANOG).

Table 2: Summary of transgenic human ES or iPS cell lines used in this proposal. DOX inducible polycistronic vectors carrying different combinations of factors will be integrated into the 3'UTR of the COL1A1 locus or GFP will be inserted into the OCT4 locus or the indicated neural specific genes. The table also indicates the specific aims where the cells will be used.

DETAILED DESCRIPTION OF THE INVENTION

The teachings of PCT Application Serial No. PCT/US08/004,516, filed Apr. 7, 2008 and U.S. patent application Ser. No. 10/997,146, filed Nov. 24, 2004 are incorporated herein by reference in their entirety. It is contemplated that the various embodiments and aspects of the invention described herein are applicable to all different aspects and embodiments of the invention. It is also contemplated that any of the embodiments or aspects can be freely combined with one or more other such embodiments or aspects whenever appropriate.

The study of induced pluripotency is complicated by the need for infection with high titer retroviral vectors resulting in genetically heterogeneous cell populations. We generated genetically homogeneous "secondary" somatic cells that carry the reprogramming factors as defined doxycycline (dox)-inducible transgenes. These cells were produced by infecting fibroblasts with dox-inducible lentiviruses, reprogramming by dox addition, selecting iPS cells, and producing chimeric mice. Cells derived from these chimeras efficiently reprogram upon dox exposure without the need for viral infection. Utilizing this system we demonstrate that (i) various induction levels of the reprogramming factors can induce pluripotency, (ii) the duration of transgene activity directly correlates with reprogramming efficiency, (iii) cells from many somatic tissues can be reprogrammed and, (iv) different cell types require different induction levels. This system facilitates the characterization of reprogramming and provides a unique platform for genetic or chemical screens to enhance reprogramming or replace individual factors.

It has recently been shown that mouse[1-4] and human[5-8] fibroblasts can be reprogrammed to a pluripotent state through retroviral-mediated introduction of four transcription factors Oct4, Sox2, Klf4, and c-Myc. Reprogramming can also be achieved in the absence of c-Myc though with decreased efficiency[9,10]. Nevertheless, with these approaches only a very small fraction of cells infected with all 4 factors will eventually reprogram[11]. The random viral infection results in genetic heterogeneity in the infected cell culture that likely plays a significant role in the low observed frequency of induced pluripotent stem (iPS) cell formation. Therefore, faithfully reprogrammed cells must be selected for by the reactivation of endogenous pluripotency genes[1-3], or based on morphological criteria[11,12]. The reprogramming process has been shown to require approximately 10 to 12 days of sustained transgene expression after viral transduction and follows a sequential activation of pluripotency markers, with initial activation of alkaline phosphatase and stage-specific embryonic antigen (SSEA1) followed by reactivation of the endogenous Oct4 and Nanog genes, after which the cultures are able to sustain the pluripotent state in the absence of transgene activity[13,14].

The cellular and genetic heterogeneity of randomly infected fibroblasts complicates the exploration of important molecular events occurring during reprogramming and limits the scalability required for high throughput analyses. To overcome these problems we developed a system to generate genetically identical cell populations amenable to reprogramming without any further genetic interference. To this end primary fibroblasts were infected with doxycycline-inducible lentiviruses encoding the 4 reprogramming factors. Following blastocyst injection chimeric mice were generated consisting of tissue types clonally derived from reprogrammed fibroblasts. From these mice homogeneous donor cell populations could be derived harboring preselected vector integrations permissible for reprogramming, allowing for the robust and simple doxycycline-induced reprogramming of primary cell types without the need for direct viral transduction of the reprogramming factors. This technology facilitates the generation of large numbers of genetically identical donor cells and represents a powerful platform for genetic or chemical screening applications to improve reprogramming. In addition, the same approach can be utilized to screen for small molecules replacing each of the 4 factors by genetic deletion of one particular factor in the pluripotent, reprogrammed fibroblasts[15]. Furthermore, this tool is not limited to fibroblast cultures but can in principle be similarly applied to all other somatic cell types, providing an attractive way to induce genes in cell types that are difficult to infect with retroviruses such as lymphocytes or intestinal epithelial cells.

Results

Generation of Genetically Homogenous Cell Populations for Drug-Inducible Reprogramming To generate cell populations homogenous with respect to the number and location of proviral integrations, we utilized a doxycycline (dox)-inducible transgene system[16,17] and constructed dox-inducible lentiviral vectors encoding the 4 reprogramming factors. Mouse embryonic fibroblasts (MEFs) containing both a reverse tetracycline transactivator and a PGK promoter-driven puromycin resistance gene targeted to the ROSA locus (ROSA-M2rtTA) in addition to a green fluorescent protein (GFP) targeted to the endogenous Nanog locus (NGFP) were infected with the 4 lentiviruses. Similarly, we infected Rosa-M2rtTA MEFs harboring the Oct4 cDNA under control of the tetracycline operator targeted to the Type I Collagen locus[16] and a neomycin resistance gene in the endogenous Nanog locus[1,18] (NNeo) with dox-inducible lentiviruses encoding Klf4, Sox2, and c-Myc (FIG. 1a).

After viral transduction, doxycycline was added to the culture medium to activate the transgenes and initiate the reprogramming process. As expected, Nanog-GFP positive and Nanog-neo resistant iPS colonies appeared and clonal iPS cell lines were established. All iPS cell lines could be expanded in the absence of dox, exhibited alkaline phosphatase activity and homogenously expressed the pluripotency markers SSEA1, and Nanog (not shown). This indicates that these "primary" iPS cell lines had activated their endogenous pluripotency core transcriptional network and no longer relied upon exogenous expression of the 4 reprogramming factors[19]. To generate somatic tissues that were composed of genetically homogenous cells carrying identical proviral insertions known to achieve reprogramming in primary fibroblasts, we injected several of these clonal primary iPS lines into blastocysts. The resulting dox-inducible iPS cell chimeras were allowed to gestate until E13.5, at which point MEFs were isolated. Puromycin selection was then used to select against cells derived from the host blastocyst leaving only iPS-derived cells. We will refer to such cells as "secondary" MEFs as they are derived from the primary iPS cells and thus carry a specific set of proviral insertions that is able to reprogram somatic cells (FIG. 1A).

Figure 6:
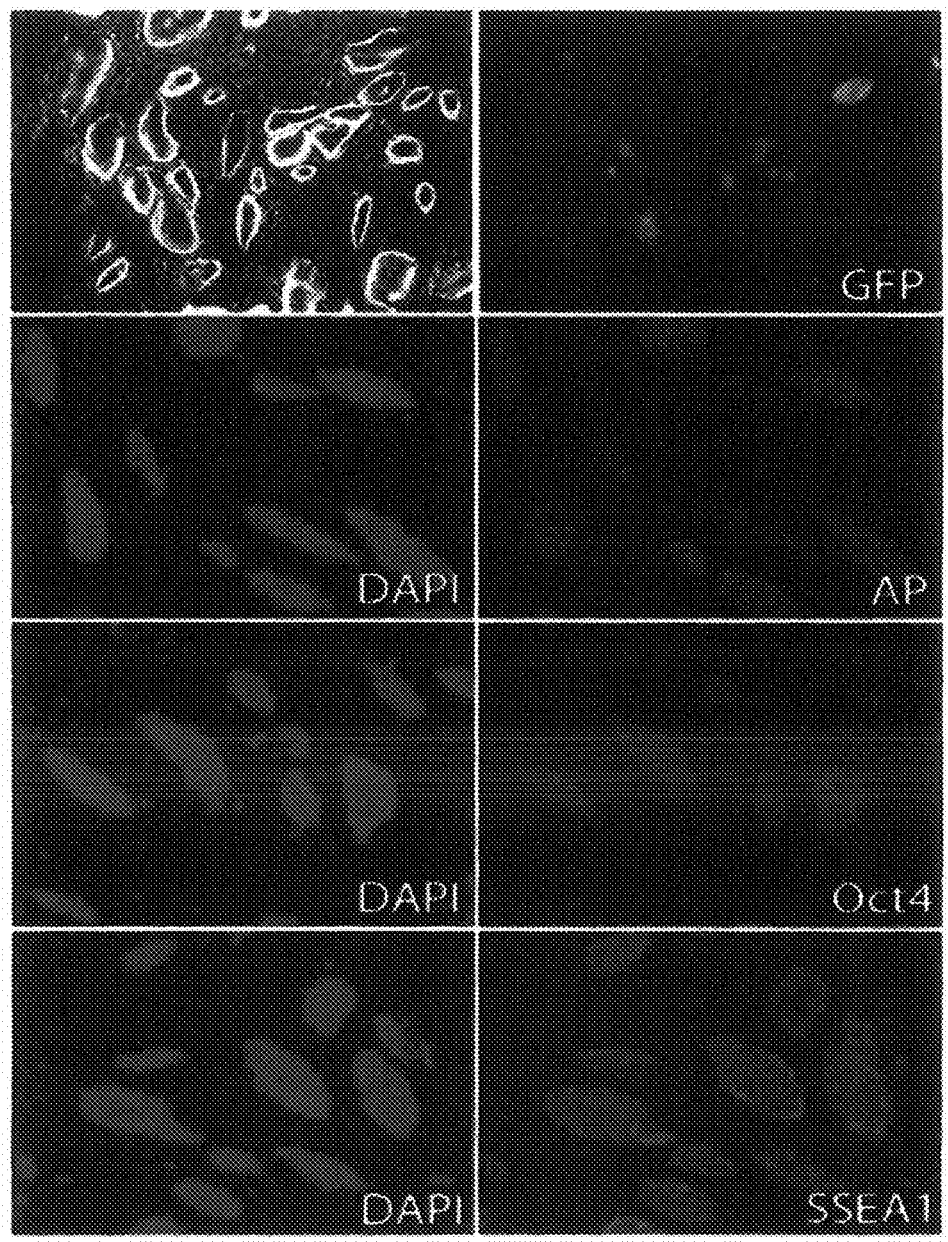
FIG. 6 shows that fully reprogrammed NGFP2 secondary MEFs reactivated the endogenous Nanog locus, express Oct4, AP, and SSEA1, and could be maintained in the absence of dox.

Secondary MEFs were isolated from chimeric iPS cell embryos generated from three distinct, clonal primary iPS cell lines (one Nanog-neo and two Nanog-GFP lines) and were cultured in the presence of dox to determine whether the integrated lentiviral vectors retained competence to mediate epigenetic reprogramming after differentiation in the developing embryo. The addition of dox to these cultures initiated dramatic morphological changes and "secondary" iPS cell lines were efficiently isolated from these cultures by neo selection or GFP expression and subsequently propagated in the absence of dox. Immunofluorescence demonstrated that secondary iPS cells had reactivated the ES cell pluripotency markers alkaline phosphatase, SSEA1, and the endogenous Nanog gene (FIG. 1B and FIG. 6). The pluripotency of these cell lines was confirmed by their ability to form cells of endodermal, ectodermal, and mesodermal lineages in teratoma formation assays and by their ability to contribute to adult chimeric mice upon blastocyst injection (FIGS. 1C, 1D).

Transgene Induction Levels, Reprogramming Kinetics, and Efficiencies Vary Between Secondary MEFS Derived from Distinct iPS Cell Lines While secondary MEFs derived from all three dox-inducible iPS cell lines underwent reprogramming to form secondary iPS cell lines, we noticed differences with respect to their morphological changes and proliferation rates after dox treatment. Initially, MEFs from both Nanog-GFP lines proliferated to form a confluent fibroblastic monolayer after exposure to dox. The cells from Nanog-GFP line 3 (NGFP3) then underwent robust post confluent proliferation including growth of cells in suspension, while cells from NanogGFP line 2 (NGFP2) grew slower, forming discreet, alkaline phosphatase positive, ES like colonies upon the fibroblastic monolayer (FIG. 2A). The fibroblasts derived from the Nanog-neo line never formed a confluent monolayer upon dox addition, but generated large, three-dimensional colonies. After 12 days of dox administration, iPS cell colonies with ES cell morphology were readily visible in all three cultures (FIG. 2A, arrows).

To evaluate the reprogramming kinetics in more detail, MEFs from the three lines were cultured in dox-containing media and flow cytometric analysis was utilized to monitor the reactivation of SSEA1 and GFP (FIG. 2C). All three secondary MEFs exhibited a gradual increase of SSEA1-positive cells over the time course, but some differences in timing were observed. The NNeo MEFs showed the earliest increase of SSEA1-positive cells from 1.3% to 17.8% between days 8 and 11. The NGFP2 MEFs showed a similar increase but at a much later time point (from 4.4% to 29% between days 14 and 18). In contrast, MEFs from the iPS cell line NGFP3 exhibited a slower, gradual activation of SSEA1 reaching about 10% on day 14. The first GFP-positive cells were detected as early as day 14 in NGFP2 and on day 18 in NGFP3 MEFs.

To monitor the timing of reactivation of the endogenous Nanog locus in NNeo secondary MEFs, we plated cells and began drug selection at various time points after dox treatment. In contrast to activation of the Nanog-GFP reporter gene around 2 weeks after induction, NNeo MEFs were neomycin resistant when neo was added to the cultures as early as day 4 (FIG. 2B). This might reflect a faster reactivation of the Nanog locus similar to what we observed for SSEA1 expression in this line (FIG. 2C). Alternatively, neo resistant colonies may appear earlier because a low level of Nanog gene activation is sufficient to give drug resistance in contrast to GFP detection which necessitates higher expression[14,20]. Although the generation of secondary cells selects for a specific set of proviral integrations the expression of which is able to induce the formation of primary iPS cell lines, the overall kinetics of pluripotency marker activation were similar to that seen in direct infection of MEFs[1,13,14]. This supports the notion that the reprogramming process requires a series of sequential epigenetic changes[11,20].

Next we compared the reprogramming efficiencies of the various secondary MEFs. To determine the optimal plating density, we plated secondary NGFP2 MEFs at densities ranging from 0.25-500 cells/mm$^2$ in dox-containing media and counted GFP-positive colonies 4 weeks later. As shown in FIG. 2D, the plating density had a profound effect on iPS formation. Remarkably, both low and high plating densities completely inhibited GFP-positive colony formation. We speculate that paracrine factors might initially be required to facilitate growth, and essential cell proliferation is impeded if cells are contact inhibited prior to activation of the transgenes.

In order to stringently determine the reprogramming efficiency in the secondary system we plated single fibroblasts from the NNeo and NGFP2 lines into 96 well plates containing γ-irradiated MEFs as feeder cells to provide optimal growth support. We observed that only ~14% and ~8% of the seeded cells from the NNeo and NGFP2 MEFs, respectively, had proliferated sufficiently to form distinct colonies after dox administration (light grey bars in FIG. 2E). However, approximately one quarter of those colonies eventually became neomycin resistant or GFP-positive after 4 weeks in culture resulting in an overall reprogramming efficiency of ~4% for the NNeo line and ~2% for the NGFP2 line (dark grey bars in FIG. 2E). This is 25-50 times more efficient than what was originally reported for drug resistance-based iPS selection[1,12] and between 4-8 times more efficient than morphology-based iPS selection in cultures of primary infected fibroblasts[11].

Figures 7A, 7B, 7C:
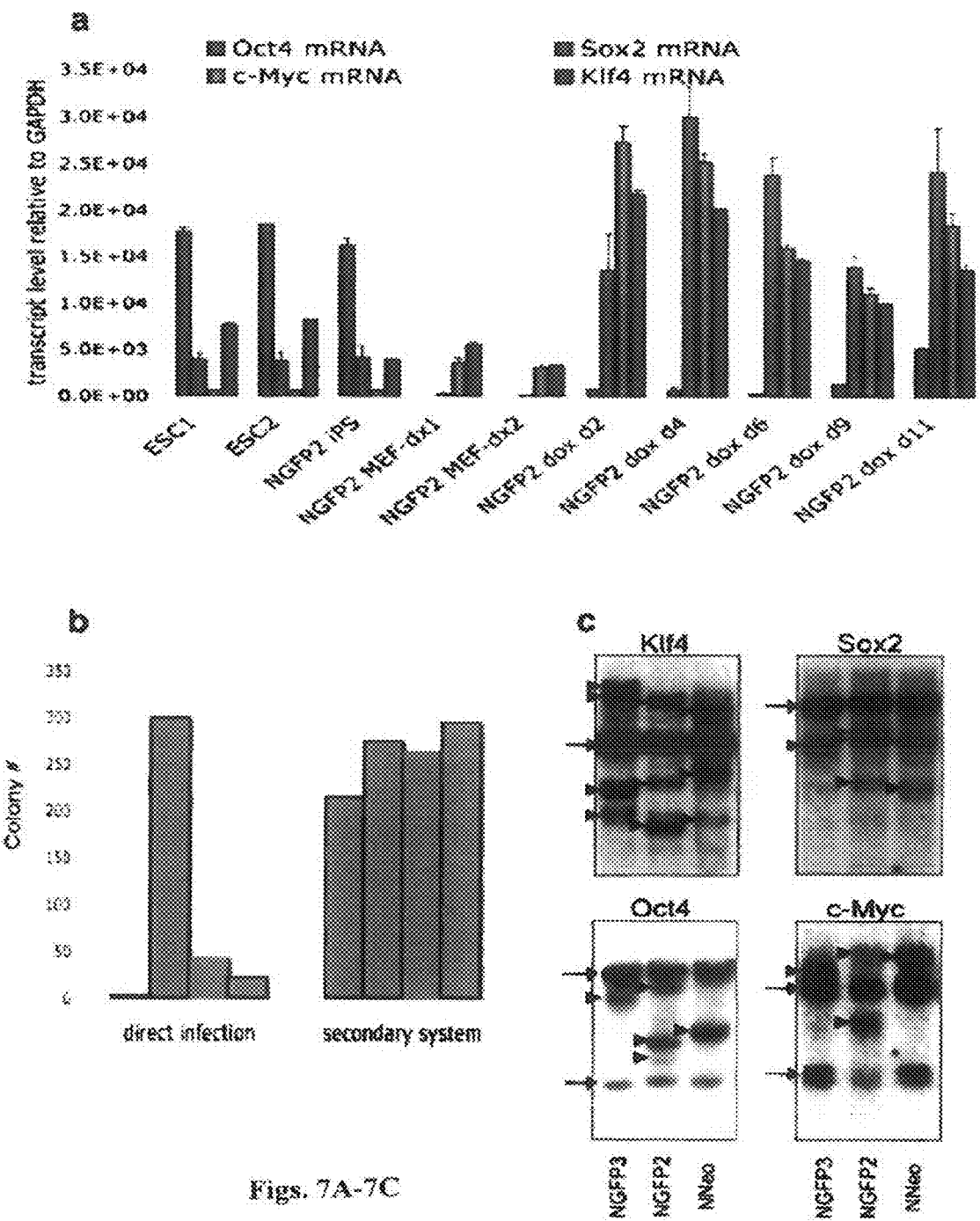
FIGS. 7A-7C show additional analysis.

We next compared the reproducibility of the secondary MEF system with direct infections. We infected Oct4-neo MEFs[1] with Moloney-based viruses encoding the 4 reprogramming factors and counted neo-resistant colonies on day 20. Four independent experiments revealed a high degree of inter-experimental variability of iPS formation using this method (FIG. 7B). In contrast, we noticed a much smaller degree of variability in the secondary system when we counted Nanog-GFP positive colonies from doxycycline-treated NGFP2 MEFs in 4 independent experiments.

Figures 3A, 3B, 3C, 3D, 3E, 3F:
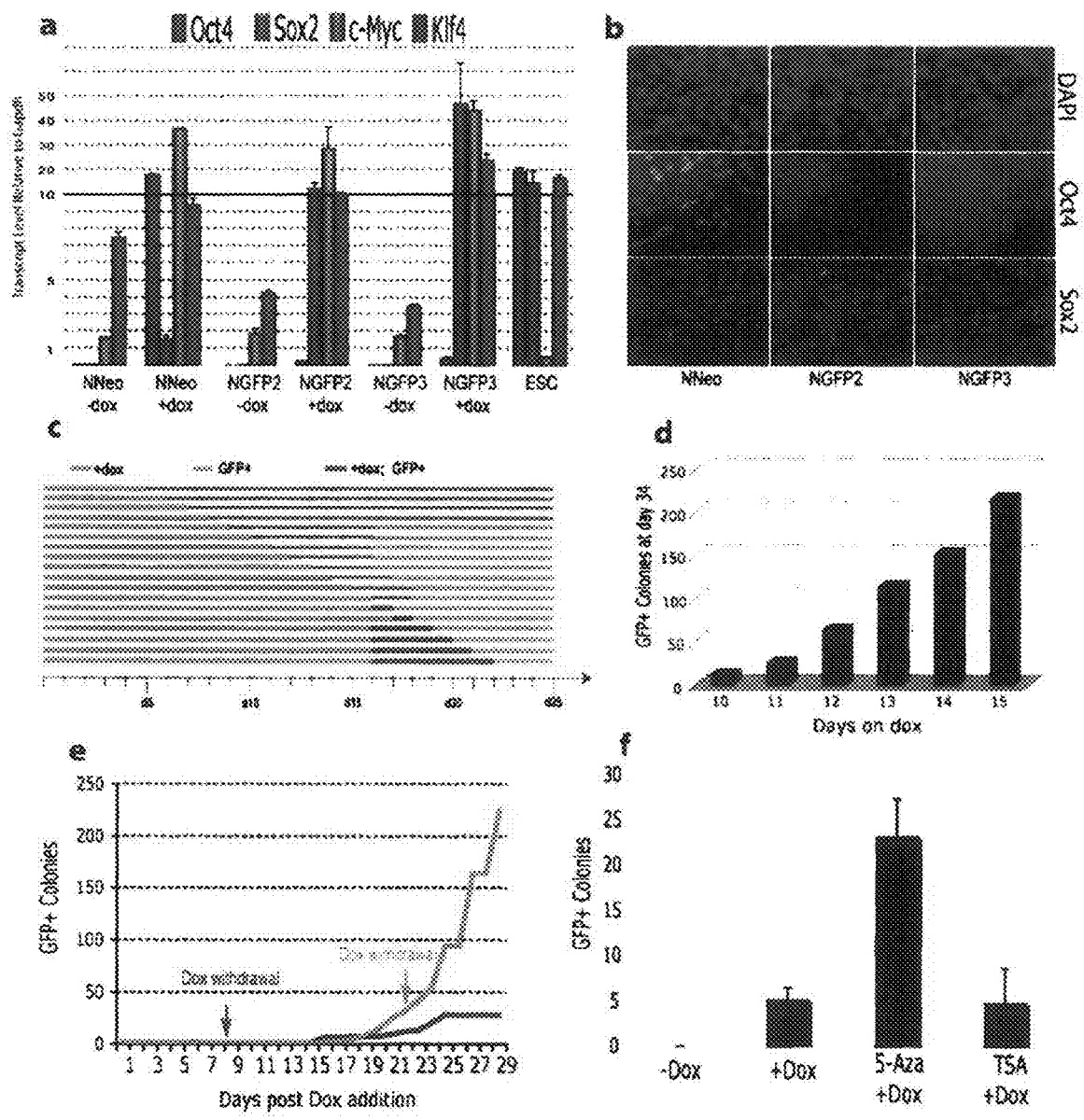
FIGS. 3A-3F show the requirement and expression of 4 factor transgenes in secondary MEFs.

To correlate the phenotypic behavior of the three secondary MEF populations with transgene induction, equal numbers of secondary MEFs were plated in the presence or absence of dox for 72 hours at which point the total transcript levels of the 4 factors were determined by quantitative RT-PCR. Surprisingly, both Nanog-GFP lines induced Oct4 at much lower levels than the NNeo line which expressed Oct4 from the transgene in the collagen 1A1 locus at levels similar to ES cells (FIG. 3A). Conversely, Sox2 induction in the Nanog-GFP lines reached levels much closer to that of endogenous Sox2 in ES cells, whereas NNeo expressed Sox2 at significantly lower levels in response to dox. c-Myc expression was higher in uninduced MEFs in comparison to ES cells, and the addition of dox resulted in a dramatic induction of transcript levels in all three secondary MEF lines. In contrast, total Klf4 levels were similar to those in ES cells in all 3 secondary MEF populations after transgene induction. The observation that total Oct4 levels in doxtreated NNeo secondary MEFs was closest to ES cells might explain the faster and more efficient reprogramming kinetics observed in this line (see above). We then determined the expression levels at later stages of reprogramming in NGFP2 MEFs. Sox2, Klf4, and c-Myc were always robustly induced with only little variation whereas Oct4 expression slowly increased over time (FIG. 7A). This might reflect the selection of cells with higher Oct4 induction over time in culture. Southern blot analysis indicated the genomic integration of 1-2 c-Myc, 1-3 Oct4, 1-3 Sox2, and 3-4 Klf4 proviruses in the three lines studied (FIG. 7C).

Despite their genetic homogeneity, dox induction resulted in activation of the transgenes that varied at the single cell level as determined by immunofluorescence analysis of Oct4 and Sox2 (FIG. 3B). Since not all secondary MEFs induced the transgenes equally in response to dox, we cannot rule out the possibility that a specific stoichiometry of transgene expression is required for reprogramming and occurs in only a subset of the secondary MEFs.

Effect of Transgene Expression on Reprogramming Efficiency and Timing

To investigate how long expression of the 4 reprogramming factors was required for stable reprogramming to occur, secondary NGFP2 MEFs were plated at optimal density (see above), exposed to doxycycline for various periods of time ranging from 5 to 22 days and monitored daily for GFP fluorescence. The minimum length of dox exposure resulting in GFP+ colonies was 9 days, with the first GFP+ colonies appearing seven days after dox removal at day 16 (FIG. 3C). Strikingly, additional exposure to dox did not accelerate the appearance of GFP+ colonies, with GFP appearing between days 16 and 18 regardless of the length of dox administration. Similarly, NNeo secondary MEFs were found to require 11-13 days of dox exposure before stable, neomycin-resistant secondary iPS colonies could be established.

To correlate the duration of transgene expression with overall reprogramming efficiency we exposed secondary NGFP2 MEFs to doxycycline for 10-15 days and quantified GFP-positive colonies on day 34. We found a striking correlation between the length of transgene expression and number of GFP-positive colonies[14] (FIG. 3D). We then monitored the appearance of newly evolving GFP-positive colonies over time in the same dish. Surprisingly, MEFs that were exposed to doxycycline for only 9 days continued to generate GFP-positive colonies up to day 25 (15 days after dox withdrawal) (FIG. 3E, blue line). Twenty-two days of dox treatment yielded a much more pronounced increase in GFP-positive colony formation over time (FIG. 3E, red line). These findings are consistent with reprogramming being a gradual stochastic process even in this genetically homogenous system and are in agreement with previous conclusions based upon primary infections[11,13,14,20]. Furthermore, the reprogramming process continues and can be completed long after the 4 transgenes are down regulated in response to dox withdrawal.

We also tested whether the secondary cells could be used to assess the effect of drugs on the efficiency of reprogramming. For this we explored the effects of the DNA demethylating compound 5-Aza-deoxycytidine (5-Aza) and the histone deacetylase inhibitor trichostatin A (TSA). Because of their action on chromatin modifications both small molecules are candidates to improve the 5 reprogramming efficiency. FIG. 3F shows that addition of 5-Aza to the medium increased the reprogramming efficiency of MEFs from the NGFP3 line whereas TSA treatment had no obvious effect on the number of colonies.

Reprogramming of Other Cell Types

We sought to determine what range of tissue types are amenable to reprogramming by isolating secondary cells from iPS cell chimeras generated from the NNeo and NGFP2 lines and examined the reprogramming ability of multiple cell types derived from these chimeras. As summarized in Table 1, some cell types could readily be reprogrammed when isolated from the NGFP2 line but the same cell types isolated from the NNeo line did not yield iPS cells suggesting that different cell types require different transgene induction levels, which may result from the different proviral integration sites between the lines studied.

TABLE 1

Summary of secondary iPS cell generation from multiple tissue and cell types derived from NNeo and NGFP chimeras

| Tissue/Cell Type | NNeo | NGFP2 |
|---|---|---|
| Neural Progenitor | + | N/D |
| Adrenal Gland | + | N/D |
| Keratinocyte | + | N/D |
| Muscle | + | N/D |
| Intestinal Epithelium | − | + |
| Mesenchymal Stem Cell | − | + |
| Hematopoietic lineage | − | + |
| MEF | + | + |
| Tail Tip fibroblast | − | + |

Intestinal Epithelial Cells

Figures 8A, 8B, 8C, 8D:
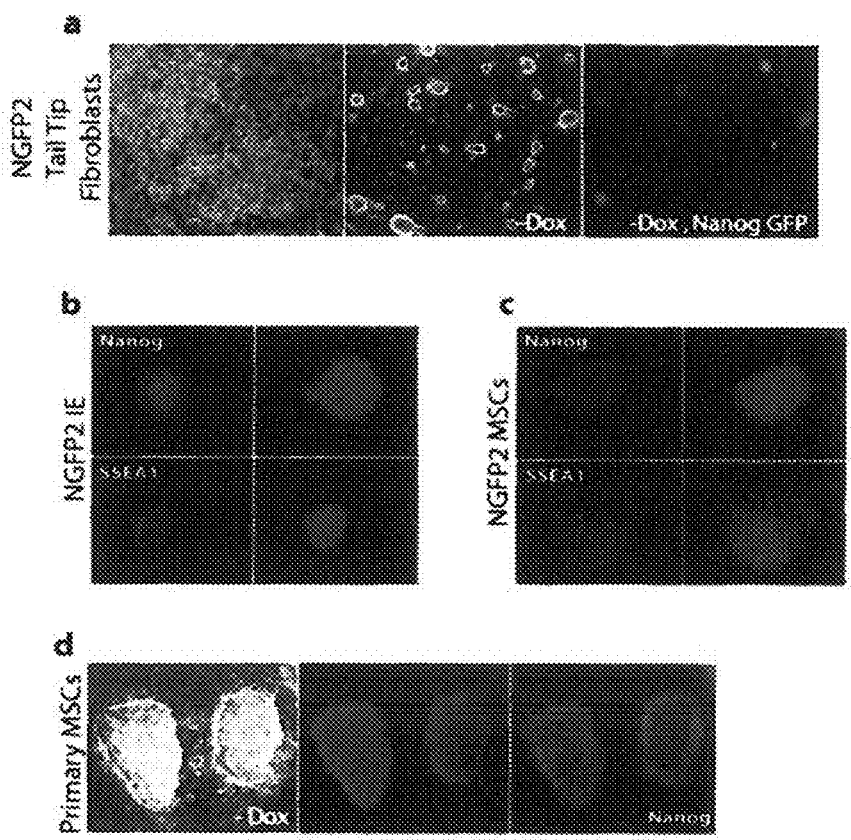
FIGS. 8A-8D show
Figures 9A, 9B, 9C, 9D, 9E, 9F, 9G:
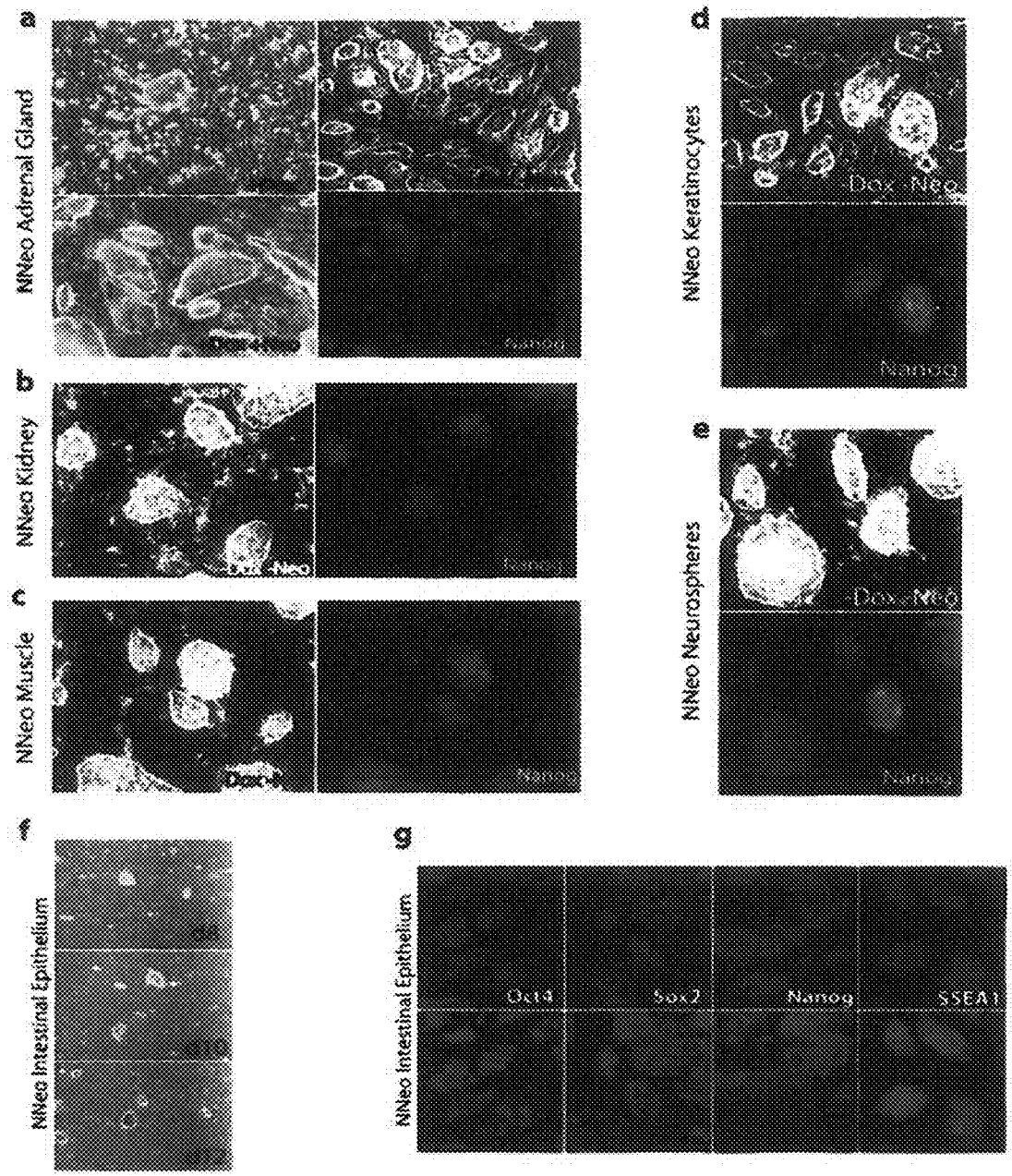
FIGS. 9A-9G show successful reprogramming of cell cultures derived from the adrenal gland (FIG. 9A), kidney (FIG. 9B), muscle (FIG. 9C), keratinocytes (FIG. 9D), and neurospheres (FIG. 9E) of NNeo secondary chimeras determined by dox independence, neomycin resistance, and Nanog expression (red, immunofluorescence).

Purified intestinal epithelial cells from both secondary NGFP2 and NNeo chimeras responded remarkably quickly to doxycycline treatment and formed spheroids in suspension within 48 hours which subsequently adhered to the MEF feeder layer and took on ES-like morphology within 3-4 days (FIGS. 4A-4C and 4I-4J). Alkaline phosphatase activity, however, was not detected prior to 10-12 days of culture with dox (FIG. 9F). Using a mechanical fractionation protocol (see Methods) we found that these colonies formed much more efficiently from fraction 7 (mostly crypt-derived cells) than from earlier fractions (enriched for villus tip-derived cells) (FIG. 4M). Cells derived from NGFP2 chimeras developed into dox-independent iPS cells that expressed endogenous Nanog after approximately two weeks of culture in the presence of dox (FIG. 4K-4L, FIG. 8B).

In contrast, cells derived from the NNeo chimera became neo resistant after two weeks of dox culture, but were unstable and lost their ES like morphology upon dox withdrawal (FIG. 4D-4F). Bisulfite sequencing revealed some degree of demethylation of the Nanog promoter but only minimal demethylation of the Oct4 promoter (FIG. 4G), and when injected under the skin of SCID mice, these cells were unable to generate teratomas in the presence or absence of doxycycline. Quantitative RT-PCR showed that these cells failed to induce Nanog and expressed only very low levels of Sox2 and Klf4 but high levels of Oct4 and c-Myc (FIG. 4H). Additional infection with Sox2 and Klf4 lead to the generation of fully reprogrammed, dox independent iPS cells expressing pluripotency markers and showing complete demethylation of their Oct4 and Nanog promoters (FIG. 4G and FIG. 9G).

Figures 4A, 4N:
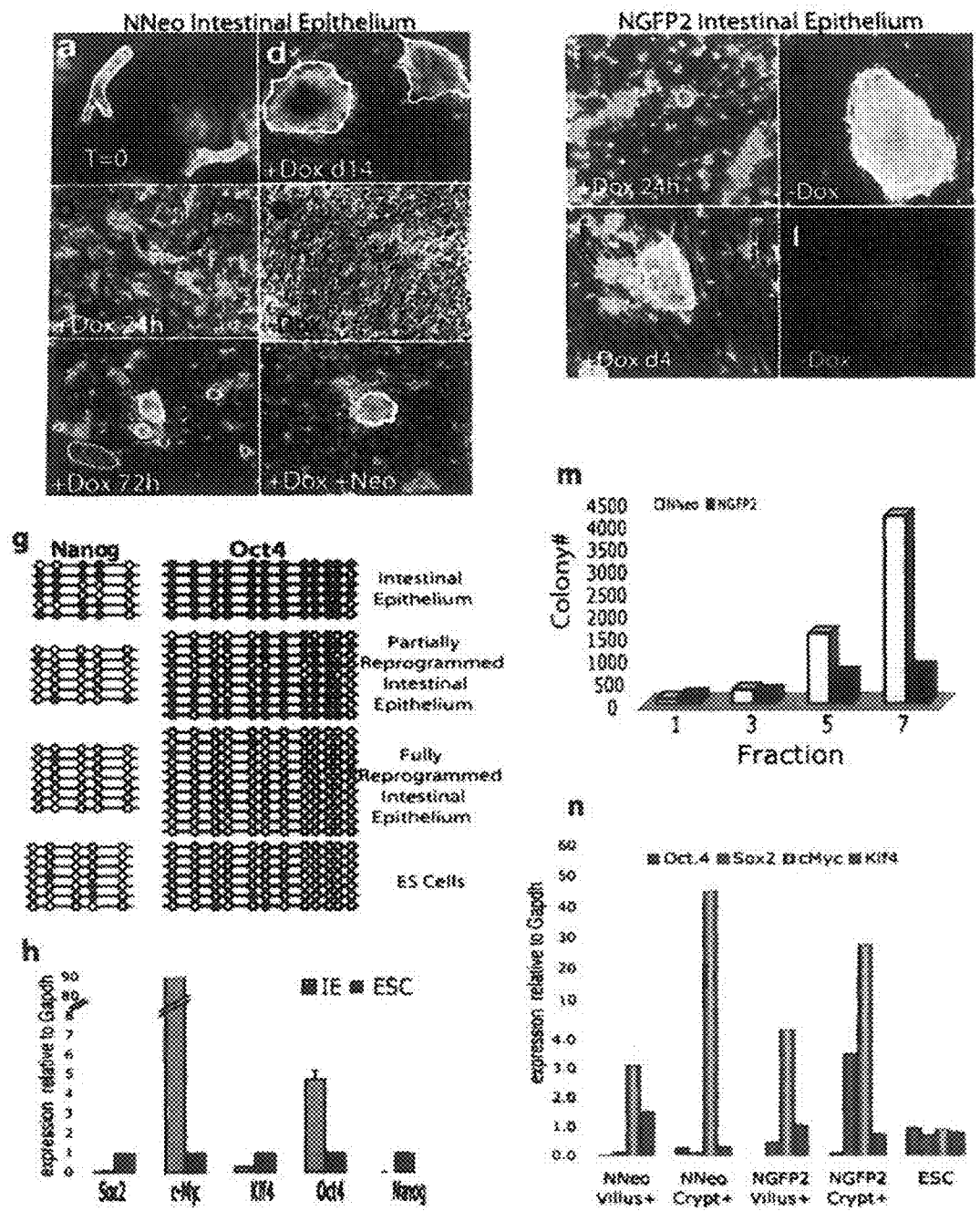
FIGS. 4A-4N show reprogramming of intestinal epithelial cells.

Comparison of transgene induction levels in NGFP2 and NNeo intestinal epithelial cells 48 hours after dox treatment revealed differences in induction levels similar to what was observed in secondary MEFs from these lines (FIG. 4N, compare to FIG. 3A). Intestinal epithelial cells derived from the crypt induced most transgenes more readily than cells from the villus, offering an explanation for their increased colony formation rate. These findings indicate the proviral integration sites in the NNeo line, while permissible for reprogramming of MEFs, are not competent to mediate full reprogramming in intestinal epithelial cells, in contrast to those present in NGFP2.

Mesenchymal Stem Cells and Tail Tip Fibroblasts

We next compared the reprogramming ability of bone marrow derived mesenchymal stem cells (MSCs) and tail tip fibroblasts (TTFs) isolated from NNeo and NGFP2 chimeras. These cells represent two mesenchymal populations that are amenable to reprogramming by direct infection[1,4,12] (Supplementary FIG. 8D). As with intestinal cells, secondary NGFP2 MSCs and TTFs were capable of generating iPS cells in response to dox, while those derived from NNeo chimeras were not (FIG. 5A-5F, FIGS. 8A,8C).

Keratinocytes

Cells isolated from the epidermis of NNeo chimeras were first propagated in the absence of doxycycline in growth conditions optimized for keratinocytes[21]. Homogeneous epithelial cultures were obtained (FIG. 5G), and doxycycline was added to the media. Clusters of epithelial cells proliferated and changed their morphology over time. After twelve days the medium was changed to doxycycline containing ES cell medium (FIG. 5H), and seven days later neomycin was added. Neo-resistant cells growing in tight colonies resembled ES cells (FIG. 5I) and were passaged onto γ-irradiated feeder cells at which point the cultures were maintained in the absence of dox and expressed endogenous Nanog (FIG. 9D).

Neural Progenitor Cells

Figures 5A, 5B, 5C, 5D, 5E, 5F, 5G, 5H, 5I, 5J, 5K, 5L:
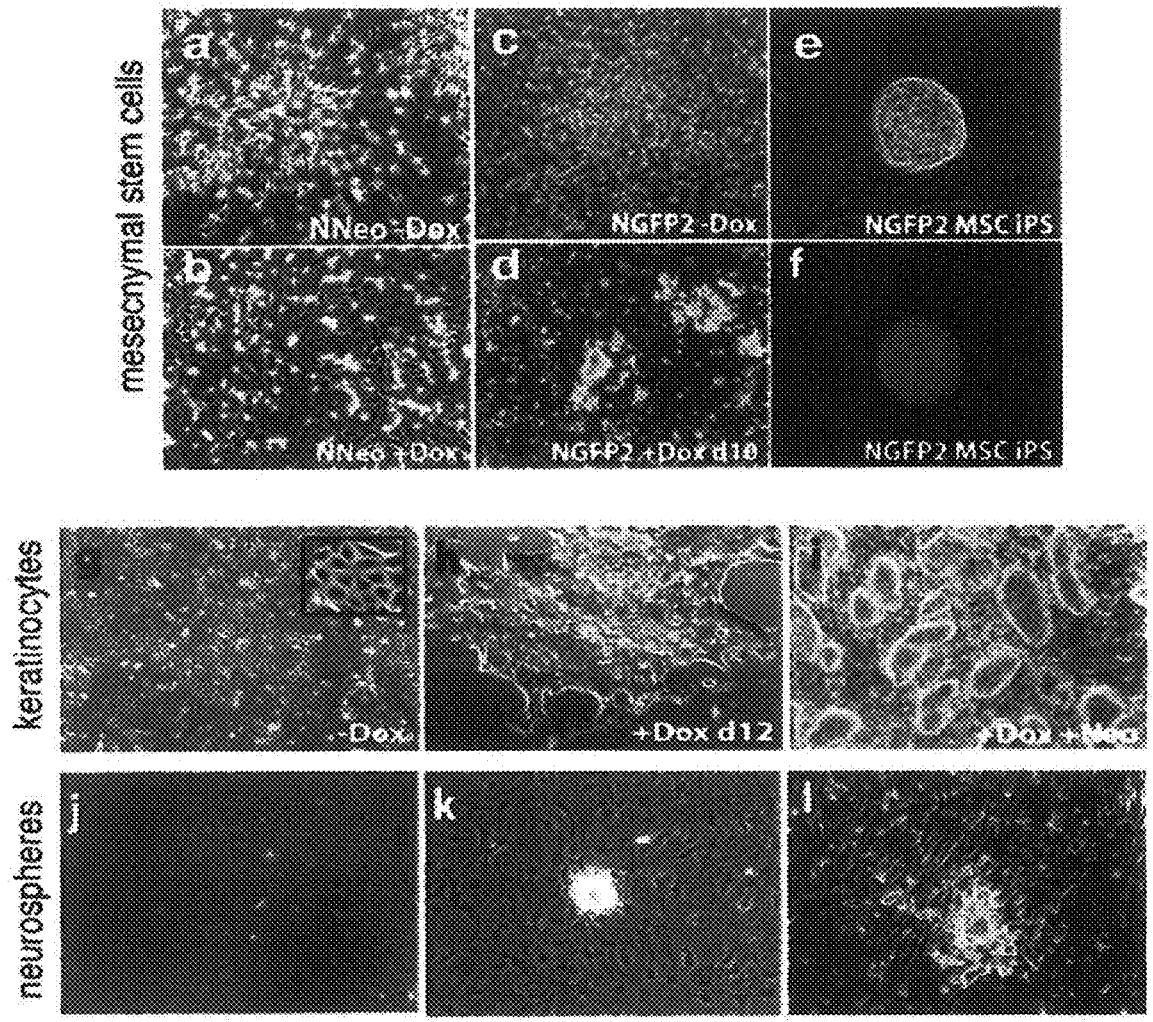
FIGS. 5A-5L show reprogramming of other somatic cell types.

Brains from NNeo chimeras were dissected and a tissue block around the lateral ventricles was dissociated into single cells and plated onto uncoated culture dishes in EGF and FGF2-containing serum-free media (N3EF) in the presence of puromycin to select for secondary cells. 4 weeks later neurospheres had formed that were subsequently plated onto polyornithine/laminin coated dishes in either ES cell or N3EF media containing dox to activate the lentiviral transgenes. As expected for neural precursors, the cells exposed to the serum-containing ES cell media differentiated into flat astrocytic cells and stopped dividing (FIG. 5J). In contrast, the cells plated in N3EF media continued to proliferate robustly resembling undifferentiated neuroepithelial cells. Three weeks later these proliferating cells were split, plated in either ES cell or N3EF media containing doxycycline. The cells exposed to serum mostly adopted a flat morphology, whereas in N3EF the cells maintained a bipolar morphology. In contrast to the previous passage however, small ES-like colonies appeared in both conditions over the next 2 weeks (FIGS. 5K, 5L). When passaged onto γ-irradiated feeder MEFs, neo-resistant, doxindependent iPS cell lines expressing endogenous Nanog were readily established (FIG. 9E).

Other Tissues

In addition, we also succeeded in generating secondary iPS cell lines from cells explanted from the adrenal gland, kidney, and muscle of NNeo chimeras. These tissues were dissected, dissociated in trypsin, and plated in ES cell media containing doxycycline. After 6-12 days in the presence of dox, colonies with ES cell morphology appeared that ultimately became neomycin resistant, dox-independent, and had activated Nanog (FIG. 9A-9C).

Reprogramming of the somatic epigenome to a pluripotent, embryonic state through the ectopic expression of the 4 transcription factors Klf4, Sox2, c-Myc, and Oct4 is a slow and inefficient process. The current method for induction of reprogramming is through retroviral gene delivery resulting in heterogeneous cell populations with proviral integrations varying in both number and genomic location, offering an explanation for the variability and inefficiency of direct reprogramming. Here we describe a novel system for reprogramming genetically homogeneous cell populations. Reprogramming with doxycycline-inducible lentiviral vectors and subsequent chimera formation yields tissues comprised of genetically homogenous cells that harbor identical proviral integrations and re-express the reprogramming factors upon exposure to doxycycline. This strategy selects for cells that carry the correct number of proviruses inserted at genomic loci that are favorable to drug-induced activation and eliminates the heterogeneity inherent in de novo viral infection of target cells. Surprisingly the timing of reprogramming in this system was similar to directly infected primary fibroblasts. The minimum length of time that dox was required to initiate reprogramming was 9-13 days. This timescale is consistent with the 10-14 day time frame observed in cells that have been directly infected with vectors[13,14]. We also observed that when dox was withdrawn from the cultures as early as day 9, GFP+ secondary iPS colonies continually appeared for the next several weeks in the absence of doxycycline. These results support the notion that reprogramming is driven by a stochastic sequence of epigenetic modifications requiring a minimum period of transgene expression.

The observed reprogramming efficiency of secondary MEFs was as high as 4% which is comparable to the reprogramming efficiency of mature B-cells[22] and vastly higher than the estimated 0.1% efficiency using de novo infection and drug selection, and about 8 fold higher than what has been reported using morphological selection criteria[1,11,12]. It has been well documented that iPS cells derived from infected MEFs carry on average 15 different proviral copies suggesting strong selection for the small fraction of the infected cells that carry the "correct" number of proviruses, or that express the 4 factors with the appropriate stoichiometry for successful reprogramming. Thus, the reprogramming frequency of secondary MEFs would be expected to be higher because these cells have been clonally derived from infected cells that carried the "correct" combination of proviruses. If so, why would 4% but not most, or all dox treated secondary cells give rise to secondary iPS cells? We consider several non-mutually exclusive explanations. (i) It has been established that genetically identical subclones of directly infected MEFs become reprogrammed at significantly different times or not at all[11,20]. As discussed previously, this suggests that reprogramming involves a sequence of stochastic events such that cells carrying an identical number of proviral copies will activate the endogenous pluripotency genes at different times. (ii) Our data also show that dox treatment does not activate the proviruses uniformly in all cells but rather that differences in induction levels exist between individual cells. Because of these variegated expression levels only a fraction of secondary MEFs may achieve high enough expression levels of or the correct relative expression levels between the factors and therefore be capable of generating secondary iPS cells.

While reprogramming is induced by viral transduction of the 4 factors, the maintenance of the pluripotent state depends on the re-establishment of the autoregulatory loop involving the activation of the four endogenous pluripotency factors Oct4, Nanog, Sox2 and Tcf3[20,23] and silencing of exogenous factors. Similarly, secondary MEFs were capable of being fully reprogrammed to a pluripotent state that was maintained in the absence of transgene expression.

We also utilized the secondary system to examine the reprogramming potential of several additional adult somatic cell types. iPS cells could be derived from many other tissues including brain, epidermis, intestinal epithelium, mesenchymal stem cells, tail tip fibroblasts, kidney, muscle and adrenal gland through dox treatment indicating that the proviruses were appropriately activated in cell types other than MEFs. This demonstrates that the 4 reprogramming factors can mediate epigenetic reprogramming in cells with different developmental origins and epigenetic states and highlights the usefulness of the secondary system for the study of reprogramming in a broad range of cell types. Although special care was taken to avoid other contaminating cell types, we cannot unequivocally demonstrate the cells of origin of iPS cells from these various tissue types. Genetic lineage tracing experiments have in fact demonstrated that iPS cells can be derived from liver and pancreas cells after transduction with Oct4, Sox2, c-Myc and Klf4[24,25]. However, not all cell types are permissive to reprogramming by these four factors. We have shown that reprogramming of mature but not of immature B cells required the transduction of an additional factor (c/EBP-alpha) or the inhibition of the B cells specific transcription factor Pax5[22]. It is possible that additional and as yet unknown factors are required to reprogram certain cell types. One practical advantage of the system described here is that cell types including those that might be refractory to ex vivo culture and retroviral infection such as intestinal epithelial cells can be studied.

The drug-inducible system described here represents a novel reprogramming platform with predictable and highly reproducible kinetics and efficiencies (see Supplementary FIG. 7B) that should facilitate the study of early molecular events leading to epigenetic reprogramming. In addition, the genetic homogeneity of secondary cell types provides the feasibility of chemical and genetic screening approaches to enhance the reprogramming efficiency. As one example, we demonstrate that the DNA demethylating agent 5-Aza-deoxycytidine substantially enhances the reprogramming efficiency. Furthermore, such screens can also be applied to identify compounds replacing the original reprogramming factors. Because the reprogrammed state is not dependent on the exogenous factors, the transgenes can be genetically excised and secondary cells can be generated by chimera formation that lack a particular reprogramming factor[15].

EXAMPLES

The teachings of all references cited herein are incorporated herein by reference in their entirety.

Example 1

Viral Preparation and Infection

Construction of lentiviral vectors containing Klf4, Sox2, Oct4, and c-Myc under control of the tetracycline operator and a minimal CMV promoter has been described previously[14]. Replication-incompetent lentiviral particles were packaged in 293T cells with a VSV-G coat and used to infect MEFs containing M2rtTA and PGK-Puro resistance gene at the R26 locus[17], as well as either a neomycin resistance or GFP allele targeted to the endogenous Nanog locus[1,11]. Viral supernatants from cultures packaging each of the 4 viruses were pooled, filtered through a 0.45 µM filter and mixed 1:1 with ES-cell medium (DMEM supplemented w/10% FBS (Hyclone, Logan, Utah), leukemia inhibitory factor, beta-mercaptoethanol (SIGMA-Aldrich), penicillin/streptomycin, L-glutamine, and nonessential amino acids (all from Invitrogen, Carlsbad, Calif.) before being applied to MEFs.

Primary iPS Isolation, Teratoma, and Chimera Formation

Approximately three weeks after the addition of dox (Sigma-Aldrich St. Louis Mo. 2 µg/mL), GFP+ or neomycin resistant iPS colonies were isolated and expanded in the absence of dox. The NanogGFP2 iPS line was picked from the same plate as line NanogGFP1 (described in[22] as MEF-iPS#1 line) whereas line NanogGFP3 was derived from an independent experiment. iPS lines were injected into C57/B6xDBA/1 F1 blastocysts. Blastocysts were placed in a drop of DMEM with 15% FBS under mineral oil. A flat-tip microinjection pipette with an internal diameter of 12-15 mm was used for iPS cell injection using a Piezo micromanipulator. About 10 iPS cells were injected into the blastocyst cavity and blastocysts were placed in KSOM (Specialty Media, Phillipsburg, N.J.) and incubated at 37° C. until they were transferred to recipient females. Fifteen injected blastocysts were transferred to the uterine horns of pseudopregnant C57/B6xDBA/1 F1 females at 2.5 days post coitum. For teratoma generation, $2\times10^6$ cells were injected subcutaneously into the flanks of recipient SCID mice, and tumors were isolated for histological analysis 3-6 weeks later. All animals were treated in accordance with institutional IACUC guidelines.

Secondary Somatic Cell Isolation and Culture

For MEF isolation, chimeric embryos were isolated at E13.5 and the head and internal (including reproductive) organs were removed. Remaining tissue was physically dissociated and incubated in trypsin at 37° C. for 20 minutes, after which cells were resuspended in MEF media containing puromycin (2 µg/mL) and expanded for two passages prior to freezing. Secondary MEFs used for the described experiments were thawed and experiments plated 1-2 passages after thawing. Kinetic experiments (FIG. 2) were performed by plating $4\times10^4$ secondary MEFs per well in 6 well plates and plates were stained or analyzed at the indicated times. Cell density experiments were performed in 12 well plates and GFP+iPS colonies were scored 4 weeks after dox induction. Single cell efficiency experiments were performed by plating single secondary MEFs onto a layer of wildtype feeder MEFS in 96 well plates prior to dox induction (using limiting dilutions, which were confirmed by eye in replicate plates lacking feeder MEFs). iPS formation was scored 4 weeks later. Representative experiments from 2-3 biological replicates are shown. For 5-Aza and TSA experiments, $1\times10^6$ secondary MEFs were plated in 6 well plates (approx 100 cells/mm$^2$) and pretreated with ES cell media containing 5-Aza (1 µM) or TSA (1 µM) for 48 h. After 48 h, secondary MEFs were cultured in ES cell media plus dox lacking 5-Aza or TSA. MEFS were exposed to 5-Aza or TSA for a second 48 h period between days 8-10 after induction, followed by culture with dox only until scoring GFP+ colonies on day 21.

Somatic organs were isolated from 3 to 4 month old chimeras. Epidermal keratinocytes were isolated and cultured as previously described[21,26]. Neural progenitor cells were isolated and cultured as previously described[27]. Total intestinal epithelium was dissociated using a solution of 3 mM EDTA and 0.05 mM DTT in PBS for 30 minutes at room temperature. The musculature was discarded and purified crypts/villi were plated on γ-irradiated feeder MEFs in the presence of dox. For crypt-villus fractionation, the same EDTA-DTT solution was used, but fractions were collected by gentle shaking for 10, 6, 5, 5, 9, 10, and 25 minutes (corresponding to fractions 1-7, respectively, with 1 representing the villus tip to 7 representing the crypt) after incubation as described in[28]. $8\times10^6$ epithelial cells from each fraction were plated on a MEF feeder layer in ES media containing 2 µg/mL dox. No growth was observed in cultures lacking dox. Whole marrow was isolated from secondary chimeric mice (or from Coll1-TetO-Oct4, Rosa26-M2rtTA mice[16] for direct infections) from the femur and tibia after removal of the condoles at the growth plate by flushing with a syringe and 30-gauge needle containing DMEM+5% Fetal BovineSerum (FBS) (Hyclone, Thermo Fisher Scientific). Mesenchymal stem cells were selected through differential plating on tissue culture plates for 72 hours in α-MEM supplemented with 15% FBS (HyClone). Colony formation of MSCs in culture was carried out by plating $4\times10^6$ nucleated cells from freshly isolated whole marrow onto 10 cm plates and allowed to expand for 5 days in the presence of puromycin to eliminate host-blastocyst derived cells, after which dox was introduced to induce reprogramming. Cultures derived from adrenal glands, muscle, and kidneys were dissected, mechanically dissociated, and digested in trypsin at 37° C. for 20 minutes prior to plating on gelatin-coated culture dishes with ES media containing dox.

Antibodies

For flow cytometric analysis we used an APC conjugated anti-mouse SSEA1 (R&D systems, Minneapolis, Minn.) and an alkaline phosphatase substrate kit: Vector Red substrate kit (Vector Laboratories, Burlingame, Calif.). For immunofluorescence, cells were fixed in 4% paraformaldehyde and we used mouse monoclonal antibodies against SSEA1 (Developmental Studies Hybridoma Bank), goat anti Sox2 (R&D Systems), mouse anti Oct4 (Santa Cruz), and rabbit anti Nanog (Bethyl). Fluorophore-labeled, appropriate secondary antibodies were purchased from Jackson ImmunoResearch.

Flow Cytometry

Cells were trypsinized, washed once in PBS and resuspended in FACS buffer (PBS+5% fetal bovine serum). $10^6$ cells were stained with 10 µl of a APC-conjugated anti-SSEA1 antibody in a 100 µl volume for 30 minutes, cells were then washed twice in PBS. Cells were then washed once with wash buffer and resuspended in FACS buffer for analysis on a FACS-caliber cell sorter.

Bisulfite Sequencing and Southern Blotting

Bisulfite treatment of DNA was done using the CpGenome DNA Modification Kit (Chemicon, Temecula, Calif.) following the manufacturer's instructions. The resulting modified DNA was amplified by nested polymerase chain reaction (PCR) using two forward (F) primers and one reverse (R) primer: Oct4 (F1, GTTGTTTTGTTTTG-GTTTTGGATAT; SEQ ID NO: 1); (F2, ATGGGTTGAAAT-ATTGGGTTTATTTA; SEQ ID NO: 2); (R, CCAC-CCTCTAACCTTAACCTCTAAC; SEQ ID NO: 3) and Nanog (F1, GAGGATGTTTTTTAAGTTTTTTTT, SEQ ID NO: 4; F2, AATGTTTATGGTGGATTTTGTAGGT, SEQ ID NO: 5; R, CCCACACTCTATATCAATATAATAAC, SEQ ID NO: 6). The first round of PCR was done as follows: 94° C. for 4 minutes; five cycles of 94° C. for 30 seconds, 56° C. for 1 minute (−1° C. per cycle), 72° C. for 1 minute; and 30 cycles of 94° C. for 30 seconds, 51° C. for 45 seconds, and 72° C. for 1 minute, 20 seconds. The second round of PCR was 94° C. for 4 minutes; 30 cycles of 94° C. for 30 seconds, 53.5° C. for 1 minute, and 72° C. for 1 minute 20 seconds. The resulting amplified products were gel-purified (Zymogen, Zymo Research, Orange, Calif.), subcloned into the TOPO TA vector (Invitrogen), and sequenced. Southern blotting of genomic DNA was carried out by digesting 10 µg of DNA with SpeI (which cuts once in the lentiviral vector backbone) followed by hybridization with random primed full-length cDNA probes for the four factors.

Quantitative RT-PCR

Total RNA was isolated using Trizol reagent (Invitrogen, Carlsbad, Calif.). Five micrograms of total RNA was treated with DNase I to remove potential contamination of genomic DNA using a DNA Free RNA kit (Zymo Research, Orange, Calif.). One microgram of DNase I-treated RNA was reverse transcribed using a First Strand Synthesis kit (Invitrogen) and ultimately resuspended in 100 µl of water. Quantitative PCR analysis was performed in triplicate using ⅟₅₀ of the reverse transcription reaction in an ABI Prism 7000 (Applied Biosystems, Foster City, Calif.) with Platinum SYBR green qPCR SuperMix-UDG with ROX (Invitrogen). Primers used for amplification were as follows: Oct4 F, 5'-ACATCGCCAATCAGCTTGG-3' SEQ ID NO: 7 and R, 5'AGAACCATACTCGAACCACATCC-3' SEQ ID NO: 8; c-myc F, 5'-CCACCAGCAGCGACTCTGA3' SEQ ID NO: 9 and R, 5'-TGCCTCTTCTCCACAGACACC-3' SEQ ID NO: 10; Klf4 F, 5'-GCACACCTGCGAACTCACAC-3' SEQ ID NO: 11 and R, 5'-CCGTCCCAGTCACAGTGG-TAA-3' SEQ ID NO: 12; Sox2 F, 5'-ACAGATGCAAC-CGATGCACC-3' SEQ ID NO: 13 and R, 5'-TGGAGTTG-TACTGCAGGGCG-3' SEQ ID NO: 14; Nanog F, 5'-CCTCCAGCAGATGCAAGAACTC3' SEQ ID NO: 15 and R, 5'-CTTCAACCACTGGTTTTTCTGCC-3' SEQ ID NO: 16. To ensure equal loading of cDNA into RT reactions, GAPDH mRNA was amplified using the following: F, 5-TTCACCACCATGGAGAAGGC-3' SEQ ID NO: 17; and R, 5'-CCCTTTTGGCTCCACCCT-3' SEQ ID NO: 18. Data were extracted from the linear range of amplification. All graphs of qRT-PCR data shown represent samples of RNA that were DNase treated, reverse transcribed, and amplified in parallel to avoid variation inherent in these procedures. Error bars represent standard deviation of the mean of triplicate reactions.

References for Example 1

1) Wernig, M. et al. In vitro reprogramming of fibroblasts into a pluripotent ES-cell-like state. Nature 448, 318-324 (2007).

2) Okita, K., Ichisaka, T. & Yamanaka, S. Generation of germline-competent induced pluripotent stem cells. Nature 448, 313-317 (2007).
3) Maherali, N. et al. Directly Reprogrammed Fibroblasts Show Global Epigenetic Remodeling and Widespread Tissue Contribution. Cell Stem Cell 1, 55-70 (2007).
4) Takahashi, K. & Yamanaka, S. Induction of pluripotent stem cells from mouse embryonic and adult fibroblast cultures by defined factors. Cell 126, 663-676 (2006).
5) Yu, J. et al. Induced pluripotent stem cell lines derived from human somatic cells. Science 318, 1917-1920 (2007).
6) Takahashi, K. et al. Induction of pluripotent stem cells from adult human fibroblasts by defined factors. Cell 131, 861-872 (2007).
7) Park, I. H. et al. Reprogramming of human somatic cells to pluripotency with defined factors. Nature 451, 141-146 (2008).
8) Lowry, W. E. et al. Generation of human induced pluripotent stem cells from dermal fibroblasts. Proc Natl Acad Sci USA 105, 2883-2888 (2008).
9) Wernig, M., Meissner, A., Cassady, J. P. & Jaenisch, R. c-Myc Is Dispensable for Direct Reprogramming of Mouse Fibroblasts. Cell Stem Cell 2, 10-12 (2008).
10) Nakagawa, M. et al. Generation of induced pluripotent stem cells without Myc from mouse and human fibroblasts. Nat Biotechnol 26, 101-106 (2008).
11) Meissner, A., Wernig, M. & Jaenisch, R. Direct reprogramming of genetically unmodified fibroblasts into pluripotent stem cells. Nat Biotechnol 25, 1177-1181 (2007).
12) Takahashi, K., Okita, K., Nakagawa, M. & Yamanaka, S. Induction of pluripotent stem cells from fibroblast cultures. Nat Protoc 2, 3081-3089 (2007).
13) Stadtfeld, M., Maherali, N., D. T., B. & Hochedlinger, K. Defining Molecular Cornerstones during Fibroblast to iPS Cell Reprogramming in Mouse. Cell Stem Cell 2, 230-240 (2008).
14) Brambrink, T. et al. Sequential Expression of Pluripotency Markers during Direct Reprogramming of Mouse Somatic Cells. Cell Stem Cell 2, 151-159 (2008).
15) Hanna, J. et al. Treatment of sickle cell anemia mouse model with iPS cells generated from autologous skin. Science 318, 1920-1923 (2007).
16) Hochedlinger, K., Yamada, Y., Beard, C. & Jaenisch, R. Ectopic expression of Oct-4 blocks progenitor-cell differentiation and causes dysplasia in epithelial tissues.
17) Cell 121, 465-477 (2005).
18) Beard, C., Hochedlinger, K., Plath, K., Wutz, A. & Jaenisch, R. Efficient method to generate single-copy transgenic mice by site-specific integration in embryonic stem cells. Genesis 44, 23-28 (2006).
19) Mitsui, K. et al. The homeoprotein Nanog is required for maintenance of pluripotency in mouse epiblast and ES cells. Cell 113, 631-642 (2003).
20) Boyer, L. A. et al. Core transcriptional regulatory circuitry in human embryonic stem cells. Cell 122, 947-956 (2005).
21) Jaenisch, R. & Young, R. Stem cells, the molecular circuitry of pluripotency and nuclear reprogramming. Cell 132, 567-582 (2008).
22) Jones, P. H. & Watt, F. M. Separation of human epidermal stem cells from transit amplifying cells on the basis of differences in integrin function and expression. Cell 73, 713-724 (1993).
23) Hanna, J. et al. Direct reprogramming of terminally differentiated mature B lymphocytes to pluripotency. Cell 133, 250-264 (2008).
24) Cole, M. F., Johnstone, S. E., Newman, J. J., Kagey, M. H. & Young, R. A. Tcf3 is an integral component of the core regulatory circuitry of embryonic stem cells. Genes Dev 22, 746-755 (2008).
25) Aoi, T. et al. Generation of Pluripotent Stem Cells from Adult Mouse Liver and Stomach Cells. Science (2008).
26) Stadtfeld, M., Brennand, K. & Hochedlinger, K. Reprogramming of Pancreatic beta Cells into Induced Pluripotent Stem Cells. Curr Biol (2008).
27) Rheinwald, J. in Cell Growth and Division: A Practical Approach. (ed. R. Baserga) 81-94 (Oxford Press, Oxford; 1989).
28) Vescovi, A. L., Galli, R. & Gritti, A. in Neural Stem Cells: Methods and Protocols. (eds. T. Zigova, P. R. Sanberg & J. R. Sanchez-Ramos) 115-123 (Humana Press, 2002).
29) Ferraris, R. P., Villenas, S. A. & Diamond, J. Regulation of brush-border enzyme activities and enterocyte migration rates in mouse small intestine. Am J Physiol 262, G1047-1059 (1992).

Example 2

I. Overview

A. Generation of Tools for the Genetic Manipulation of Human ES and IPS Cells

Work described herein provides robust approaches for targeting genes in huES cells and to generate tools for the reprogramming of somatic cells into iPS cells. More specifically, homologous recombination is used to insert GFP into key neural lineage genes of huES and iPS cells. The GFP marker is used to isolate neuronal precursor cells from manipulated iPS cells to assess their developmental potential. The current reprogramming protocols rely on retroviral vector-mediated transduction of transcription factors resulting in multiple proviral insertions in the iPS cells. This work describes methods that either avoid the use of multiple viral infections or all but eliminate the requirement for virus-mediated reprogramming.

1. DOX and Tamoxifen Inducible Retroviral Vectors

DOX inducible retroviral vectors have been important to define the sequential activation of pluripotency markers and the minimum time of vector expression during reprogramming of somatic mouse cells. We have generated inducible lentiviral vectors that will allow the temporally restricted expression of the reprogramming factors.

Figures 11A, 11B:
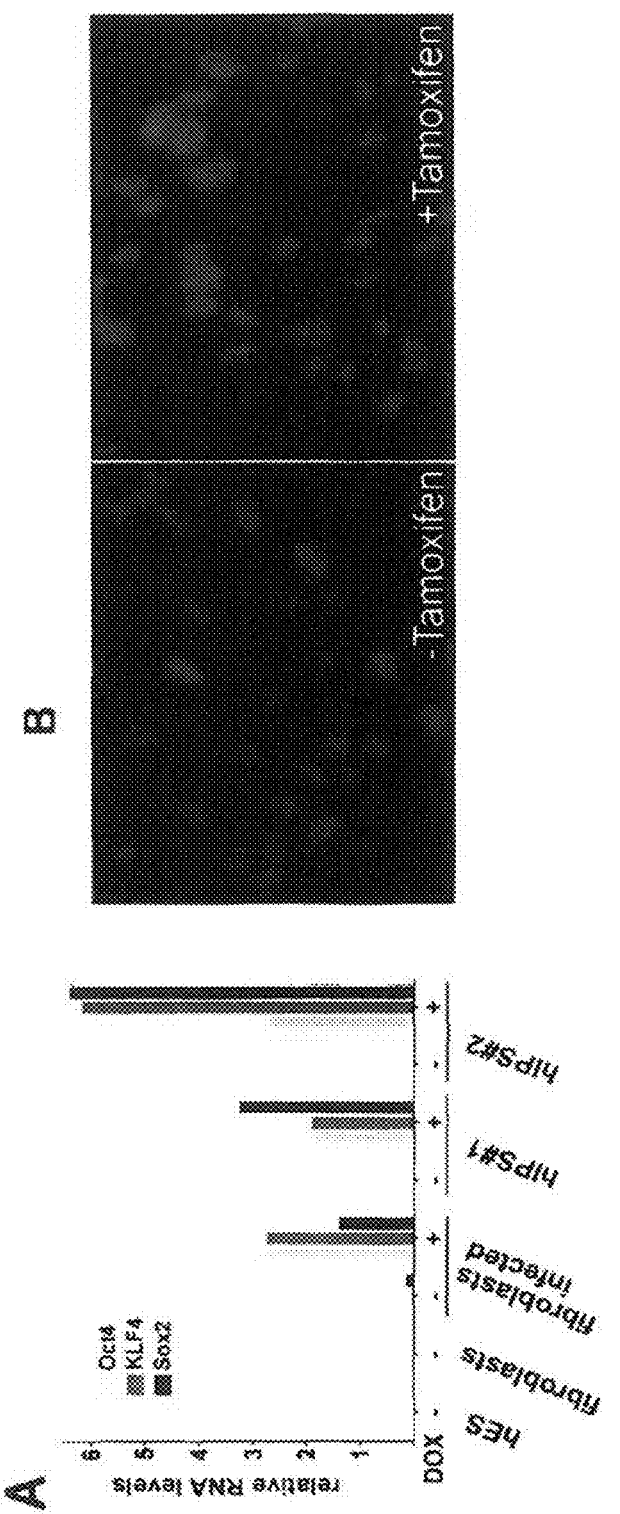
FIGS. 11A-11B show DOX and tamoxifen inducible factor expression.

(a) DOX inducible lentivirus vectors: Following the same strategy as used for murine genes we have generated lentiviral vectors that transduce the human OCT4, SOX2, KLF4 and C-MYC c-DNAs either constitutively or under the control of a DOX inducible promoter [Brambrink, 2008 #6877]. To generate a DOX inducible system we infected human fibroblasts with a lentiviral vector carrying the rtTA transactivator. FIG. 11A shows high DOX-dependent expression of OCT4, SOX2, and KLF4 in fibroblasts transduced with the respective DOX inducible vectors. Similarly, robust DOX dependent transgene expression was observed in iPS cells derived from the infected fibroblasts (right two panels of FIG. 11A).

(b) Tamoxifen inducible lentivirus vectors: To enable independent inducible control of vectors we also generated OCT4, SOX2 and C-MYC estrogen receptor (ER) fusion constructs by fusing the factors to the estrogen ligand binding domain to allow for tamoxifen dependent expression [Grandori, 1996 #6505]. As shown in FIG. 11B, addition of tamoxifen to cells transduced with a SOX2-ER fusion construct leads to translocation of the SOX2 protein from the cytoplasm to the nucleus as expected for drug induced activation. These results show that the DOX and ER fusion inducible systems can be used to independently control the expression of transduced factors.

One important concept is the use of two different regulatable systems, each controlling expression of a subset of the factors. For example, one might place 3 of the factors under control of a first inducible (e.g., dox-inducible) promoter and the $4^{th}$ factor under control of a second inducible (e.g., tamoxifen-inducible) promoter. Then, one could generate an iPS cell by inducing expression from both promoters, generate a mouse from this iPS cell, and isolate fibroblasts (or any other cell type) from the mouse. These fibroblasts would be genetically homogenous and would be reprogrammable without need for viral infection. One would then attempt to reprogram the fibroblasts under conditions in which only the first promoter is active, in the presence of different small molecules that could potentially substitute for the $4^{th}$ factor, in order to identify small molecule "reprogramming agents" or optimize transient transfection or other protocols for introducing the $4^{th}$ factor. A number of variations are possible; for example, one might stably induce expression of 3 factors and transiently induce expression of the $4^{th}$ factor, etc. Also, one can modulate expression levels of the factors by using different concentrations of inducing agent.

Another approach is to place the gene that encodes one of the factors between sites for a recombinase and then induce expression of the recombinase to turn off expression of that factor. Recombinase expression could be induced by infecting with a viral vector (e.g., Adenovirus-Cre). Hanna, et al, Science, 318, 1920-1923 (2007) describes such an approach, which was used to reduce the potential risk of tumor formation due to c-Myc transgene expression—Cells were infected with retroviruses encoding for Oct4, Sox2, and Klf4 factors and a lentivirus encoding a 2-lox c-Myc cDNA. iPS cells generated from these cells were infected with an adenovirus encoding Cre recombinase to delete the lentivirus-transduced c-Myc copies.

These systems are useful, e.g., for identifying reprogramming agents and studying the requirements and events that occur in reprogramming (including discovering cell-type specific differences).

2. Generation of Human iPS Cells Confirming that the Inducible System Works as Expected in Human as Well as Mouse.

Figures 12A, 12B, 12C:
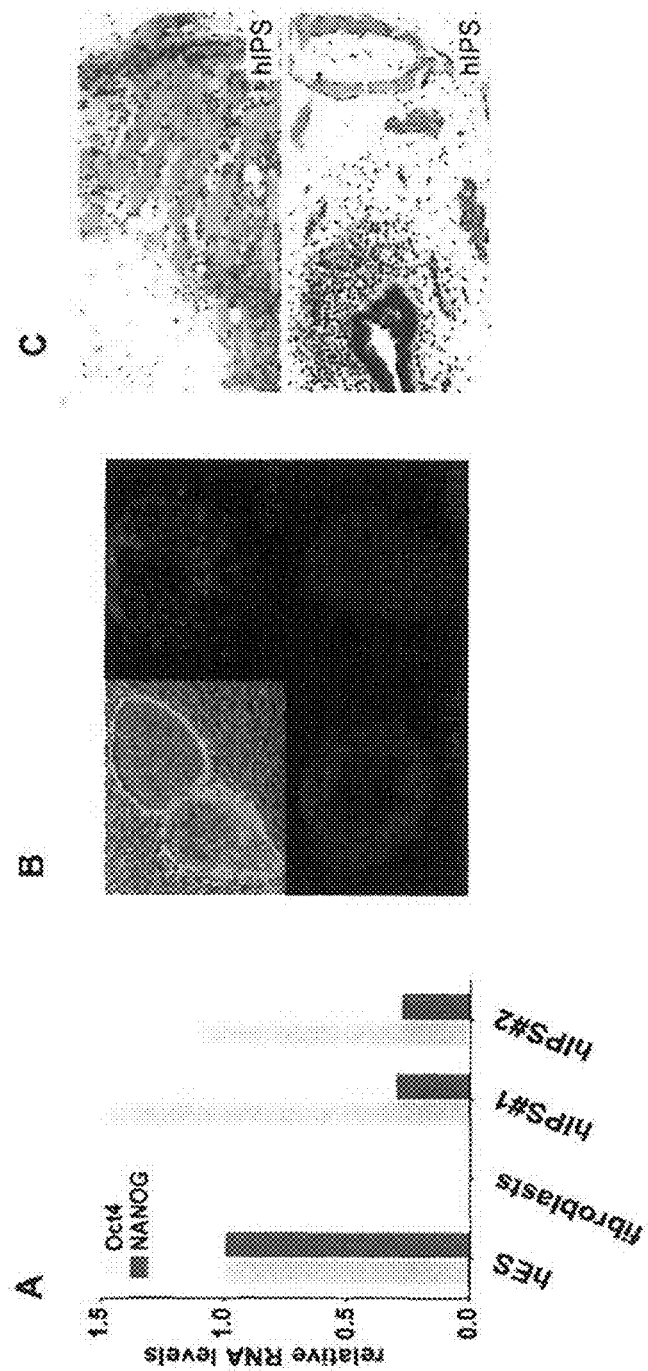
FIGS. 12A-12C show generation of iPS cells from human fibroblasts.

A number of different strategies have been shown to induce iPS cells from mouse or human somatic donor cells including the constitutive or inducible expression of the four transcription factors Oct4, Sox2, Klf4 and c-myc or a subset of the four factors or alternative factor combinations [Lowry, 2008 #6827; Park, 2008 #6783; Takahashi, 2007 #6769; Yu, 2007 #6793]. The utility of the different vector systems described in FIG. 11A for the reprogramming of human fibroblasts was compared. Table 1 shows that iPS cells were obtained by transduction of 4 or 3 (minus C-MYC) constitutively expressed or DOX inducible transcription factors. When the DOX inducible lentiviruses were used iPS clones appeared with a similar frequency and after about the same time in the infected cultures as has been published by others [Takahashi, 2007 #6769]. FIG. 12A shows that the endogenous OCT4 and NANOG genes were expressed in 2 iPS lines at similar levels as in huES cells. The reprogrammed iPS cells grew as tight colonies with morphology typical of human ES cells and they expressed the appropriate pluripotency markers (FIG. 12B). To test for pluripotency the iPS cells were injected into SCID mice. Histological examination of the resulting tumors showed typical teratomas containing multiple differentiated cell types (FIG. 12C).

B. Generation of Mouse and Human iPS Cells by a Polycistronic Retroviral Vector

Many current protocols to generate iPS cells call for transduction of the 4 transcription factors Oct4, Sox2, c-myc and Klf4 by four different retroviral vectors. Reprogramming in this manner involves the selection for the small fraction of infected cells that carry multiple integrated vectors (up to 15 or more proviruses) raising concerns of cancer due to the use of powerful oncogenes and/or retrovirus induced insertional mutagenesis. To reduce the number of independent proviral integrations required for reprogramming we have designed and used a polycistronic vector that can transduce any combination of the factors with a goal of reducing the number of proviral integrations.

Internal ribosomal entry sites (IRES) are widely used to express multiple genes from one promoter but this frequently leads to non-stoichiometric expression of the genes. The self-cleaving 18-22 amino acids long 2A peptides mediate 'ribosomal skipping' between the proline and glycine residues and inhibit peptide bond formation without affecting downstream translation. These peptides allow multiple proteins to be encoded as polyproteins, which dissociate into component proteins upon translation. Use of the term "self-cleaving" is not intended to imply proteolytic cleavage reaction.

Self-cleaving peptides are found in members of the Picornaviridae virus family, including aphthoviruses such as foot-and-mouth disease virus (FMDV), equine rhinitis A virus (ERAV), Thosea asigna virus (TaV) and porcine teschovirus-1 (PTV-1) (Donnelly, M L, et al., J. Gen. Virol., 82, 1027-101 (2001); Ryan, M D, et al., J. Gen. Virol., 72, 2727-2732 (2001) and cardioviruses such as Theilovirus (e.g., Theiler's murine encephalomyelitis) and encephalomyocarditis viruses. The 2A peptides derived from FMDV, ERAV, PTV-1, and TaV are sometimes referred to herein as "F2A", "E2A", "P2A", and "T2A", respectively. Aphthovirus 2A polypeptides are typically ~18-22 amino acids long and contain a Dx1Ex2NPG (SEQ ID NO: 34), where x1 is often valine or isoleucine. As noted above, the 2A sequence is believed to mediate 'ribosomal skipping' between the proline and glycine, impairing normal peptide bond formation between the P and G without affecting downstream translation. An exemplary 2A sequence is VKQTLNFDLLKLAGDVESNPGP (SEQ ID NO: 35) from FMDV, where underlined residues are conserved in many 2A peptides. The C terminus of cardiovirus 2A peptides is conserved, shows a high degree of similarity with FMDV 2A peptide, and has been shown to also mediate self-cleavage (Donnelly, M L, et al., J. Gen. Virol., 78, 13-21 (1997). FDMV 2A peptide has been shown to mediate cleavage of an artificial polyprotein (Ryan, M D and Drew, J., EMBO J., 13, 928-933 (1994). The ability to express four proteins efficiently and stoichiometrically from one polycistron in vivo was demonstrated recently using self-processing 2A peptides to express the four CD3 proteins (Szymczak et al., Nature Biotech. 5, 589-594, 2004). Polycistronic transgenes in which the individual cDNAs are separated by 2A peptides have been shown to promote polycistronic gene expression in transfected cells including huES cells (Hasegawa, K., et al., Stem Cells. 2007 July; 25(7):1707-12, 2007).

The present invention provides polycistronic nucleic acid constructs, expression cassettes, and vectors useful for generating induced pluripotent stem (iPS) cells. In certain embodiments the polycistronic nucleic acid constructs comprise a portion that encodes a self-cleaving peptide. The invention provides a polycistronic nucleic acid construct comprising at least two coding regions, wherein the coding regions are linked to each by a nucleic acid that encodes a self-cleaving peptide so as to form a single open reading frame, and wherein the coding regions encode first and second reprogramming factors capable, either alone or in combination with one or more additional reprogramming factors, of reprogramming a mammalian somatic cell to pluripotency. In some embodiments of the invention the construct comprises two coding regions separated by a self-cleaving peptide. In some embodiments of the invention the construct comprises three coding regions each encoding a reprogramming factor, wherein adjacent coding regions are separated by a self-cleaving peptide. In some embodiments of the invention the construct comprises four coding regions each encoding a reprogramming factor, wherein adjacent coding regions are separated by a self-cleaving peptide. The invention thus provides constructs that encode a polyprotein that comprises 2, 3, or 4 reprogramming factors, separated by self-cleaving peptides. In some embodiments the construct comprises expression control element(s), e.g., a promoter, suitable to direct expression in mammalian cells, wherein the portion of the construct that encodes the polyprotein is operably linked to the expression control element(s). The invention thus provides an expression cassette comprising a nucleic acid that encodes a polyprotein comprising the reprogramming factors, each reprogramming factor being linked to at least one other reprogramming factor by a self-cleaving peptide, operably linked to a promoter (or other suitable expression control element). The promoter drives transcription of a polycistronic message that encodes the reprogramming factors, each reprogramming factor being linked to at least one other reprogramming factor by a self-cleaving peptide. The promoter can be a viral promoter (e.g., a CMV promoter) or a mammalian promoter (e.g., a PGK promoter). The expression cassette or construct can comprise other genetic elements, e.g., to enhance expression or stability of a transcript. In some embodiments of the invention any of the foregoing constructs or expression cassettes may further include a coding region that does not encode a reprogramming factor, wherein the coding region is separated from adjacent coding region(s) by a self-cleaving peptide. In some embodiments the additional coding region encodes a selectable marker.

Specific reprogramming factors that may be encoded by the polycistronic construct include transcription factors Oct4, Sox2, Klf4, c-Myc, and Nanog, which are further described herein and known in the art. The invention encompasses all combinations of two or more of the foregoing factors, in each possible order. For purposes of brevity, not all of these combinations are individually listed herein. In some embodiments, the construct encodes Oct4, Klf4, and Sox2, separated by 2A peptides. In some embodiments the construct does not encode c-Myc. In some embodiments, the construct contains a coding region that encodes Lin28. In some embodiments, the construct contains a coding region that encodes C/EBP alpha.

In some embodiments the construct comprises one or more sites that mediates or facilitates integration of the construct into the genome of a mammalian cell. In some embodiments the construct comprises one or more sites that mediates or facilitates targeting the construct to a selected locus in the genome of a mammalian cell. For example, the construct could comprise one or more regions homologous to a selected locus in the genome.

In some embodiments the construct comprises sites for a recombinase that is functional in mammalian cells, wherein the sites flank at least the portion of the construct that comprises the coding regions for the factors (i.e., one site is positioned 5' and a second site is positioned 3' to the portion of the construct that encodes the polyprotein), so that the sequence encoding the factors can be excised from the genome after reprogramming. The recombinase can be, e.g., Cre or Flp, where the corresponding recombinase sites are LoxP sites and Frt sites. In some embodiments the recombinase is a transposase. It will be understood that the recombinase sites need not be directly adjacent to the region encoding the polyprotein but will be positioned such that a region whose eventual removal from the genome is desired is located between the sites. In some embodiments the recombinase sites are on the 5' and 3' ends of an expression cassette. Excision may result in a residual copy of the recombinase site remaining in the genome, which in some embodiments is the only genetic change resulting from the reprogramming process.

In some embodiments the construct comprises a single recombinase site, wherein the site is copied during insertion of the construct into the genome such that at least the portion of the construct that encodes polyprotein comprising the factors (and, optionally, any other portion of the construct whose eventual removal from the genome is desired) is flanked by two recombinase sites after integration into the genome. For example, the recombinase site can be in the 3' LTR of a retroviral (e.g., lentiviral) vector (see, e.g., Example 4).

In some aspects, the invention provides vectors comprising the polycistronic nucleic acid constructs. In some embodiments the vectors are retroviral vectors, e.g., lentiviral vectors. In other embodiments the vectors are non-retroviral vectors, e.g., which may be viral (e.g., adenoviral) or non-viral. Exemplary polycistronic nucleic acid constructs, expression cassettes, and vectors are described in Example 3

In some aspects, the invention provides cells and cell lines (e.g., somatic cells and cell lines such as fibroblasts, keratinocytes, and cells of other types discussed herein) in which a polycistronic nucleic acid construct or expression cassette (e.g., any of the constructs or expression cassettes described herein) is integrated into the genome. In some embodiments the cells are rodent cells, e.g., a murine cells. In some embodiments the cells are primate cells, e.g., human cells.

In some embodiments at least the portion of the construct that encodes the polyprotein is flanked by sites for a recombinase. After a reprogrammed cell is derived, a recombinase can be introduced into the cell, e.g., by protein transduction, or a gene encoding the recombinase can be introduced into the cell, e.g., using a vector such as an adenoviral vector. The recombinase excises the sequences encoding the exogenous reprogramming actors from the genome. In some embodiments the cells contain an inducible gene that encodes the recombinase, wherein the recombinase is expressed upon induction and excises the cassette. In some embodiments the inducible gene is integrated into the genome. In some embodiments the inducible gene is on an episome. In some embodiments the cells do not contain an inducible gene encoding the recombinase.

In some embodiments, the nucleic acid construct or cassette is targeted to a specific locus in the genome, e.g., using homologous recombination. In some embodiments the locus is one that is dispensable for normal development of most or all cell types in the body of a mammal. In some embodiments the locus is one into which insertion does not affect the ability to derive pluripotent iPS cells from a somatic cell having an insertion in the locus. In some embodiments the locus is one into which insertion would not perturb pluripotency of an ES cell. In some embodiments the locus is the COL1A1 locus or the AAV integration locus. In some embodiments the locus comprises a constitutive promoter. In some embodiments the construct or cassette is targeted so that expression of the polycistronic message encoding the polypeptide comprising the factors is driven from an endogenous promoter present in the locus to which the construct or cassette is targeted.

The invention further provides pluripotent reprogrammed cells (iPS cells) generated from the somatic cells that harbor the nucleic acid construct or expression cassette in their genome. The iPS cells can be used for any purpose contemplated for pluripotent cells. Further provided are differentiated cell lines (e.g., neural cells, hematopoietic cells, muscle cells, cardiac cells), derived from the pluripotent reprogrammed cells. Exemplary somatic cells and iPS cell generated therefrom are described in Example 3.

The present invention establishes that the reprogramming factors possess the requisite structural features to allow efficient processing of the 2A sequence when located between reprogramming factors, an important finding since it is recognized that cleavage is a structure-based event (Szymczak, supra). The present disclosure establishes that transcription factors having the additional ~17-21 amino acids from the 2A peptide at their C-terminus retain the ability to enter the nucleus and perform their functions. The present disclosure also establishes that reprogramming factors can tolerate the presence of the additional ~17-21 amino acids from the 2A peptide that remain on the C-terminus of the upstream protein and remain functional in reprogramming.

While reprogramming by infecting with high titer retroviral vectors to express the required reprogramming factors is highly reproducible, the process is relatively inefficient and the precise requirements in terms of timing and order of expression of the factors, as well as the absolute and relative levels of expression required, remain incompletely understood. Moreover, when iPS cells are generated by infecting cells with multiple viruses, each encoding a single factor, in many current protocols, each virus has been shown to cause integrations at between 2-6 locations, resulting in ~14-20 insertion events throughout the genome. This process creates iPS cells that are genetically modified and may contain unknown insertion-generated mutations. Furthermore, since only a small fraction of infected cells become reprogrammed, the results obtained using these multi-virus protocols leave open the question as to whether the location of the integrations and/or the relative timing at which expression from the transgenes occurs is an important determinant of whether a cell will become reprogrammed. The instant invention establishes that essentially simultaneous expression of multiple factors from a polycistronic transcript and at relative levels dependent on the efficiency of the 2A cleavage event, is effective to induce reprogramming. Furthermore, the invention establishes that a single copy of the factors is sufficient for reprogramming. Because the four factors are expressed from a defined location in certain embodiments of the invention (e.g., a location that is preselected or one that is determined after integration of the vector) the polycistronic vector system may simplify the study of reprogramming mechanisms and facilitates the excision of the vector. In some embodiments, such excision results in removal of at least the exogenous sequences encoding the reprogramming factors. In some embodiments, such excision results in iPS cells that carry no genetic modification other than, in some embodiments, a residual recombinase site. In other embodiments, there are no more than 2, 3, 4, or 5 residual recombinase sites. Without wishing to be bound by theory, reprogramming cells containing a single integrated construct will increase the likelihood or ease of recovering transgene-free iPS cells using recombinase-based approaches. It is also contemplated that polycistronic vectors encoding 2, 3, or 4 factors may be used in combination with small molecules, proteins, or other agents that enhance reprogramming and/or that substitute for one or more factors not encoded by the polycistronic vector.

Example 4 describes experiments in which human induced pluripotent stem cells (hiPSCs) free of reprogramming factors were derived using Cre-recombinase excisable viruses from fibroblasts from individuals with Parkinson's disease (PD). In some embodiments of the invention, iPS cells carrying no exogenous genes encoding reprogramming factors are derived as described in Example 4 or using similar methods, except that a single vector comprising a polycistronic nucleic acid construct encoding a polyprotein comprising multiple (2, 3, or 4 factors) is used rather than multiple vectors encoding single factors. Of course the methods described in Example 4 can also be used with multiple vectors encoding individual factors in order to obtain iPS cells without exogenous genes encoding reprogramming factors, wherein the resulting iPS cells have only a small number of residual recombinase sites. While fibroblasts from individuals with PD were used as an exemplary cell type in Example 4, the methods are applicable to derive iPS cells with minimal genetic alteration from normal somatic cells (e.g., fibroblasts or other cell types such as keratinocytes, intestinal cells, blood cells) or from somatic cells from individuals with a disease of interest. In some embodiments, the gene encoding the transactivator is also flanked by recombinase sites, so that it is removed from the genome as well.

The iPS cells and differentiated cells obtained from them are of use for research purposes (e.g., as a model system to study the disease and/or identify therapeutic agents for the disease) and/or for the development of cell-based therapies, which in some embodiments are patient-specific cell-based therapies.

C. Developmental Potential of Human iPS Cells and Derivation from Peripheral Blood An exciting potential of the iPS system is to derive patient specific pluripotent cells. Work described herein describes protocols that will allow the study of complex human diseases in vitro using patient specific iPS cells. For example, at present patient specific iPS cells are derived from deep skin biopsies. In an effort to establish a potentially more simple protocol to isolate iPS cells in a clinical setting procedures described here use peripheral blood as donor material for generating iPS cells.

D. Screen for Small Molecules

Work described herein provides high throughput systems for identifying small molecules that improve reprogramming efficiency. This allows for the establishment of a reprogramming method that does not require the genetic manipulation or insertion of exogenous genetic elements such as vector mediated transduction of oncogenes like C-MYC or KLF4.

II. Experimental Approach

In the mouse system the use of vectors that allowed for drug inducible expression of the transcription factors has been crucial to define the molecular events that cause reprogramming. These experiments indicated that reprogramming involves the sequential activation of ES cell markers such as alkaline phosphatase, SSEA1, Oct4 and Nanog and that the transduced transcription factors needed to be expressed for at least 12 days in order to give rise to iPS cells [Brambrink, 2008 #6877]. A major goal of aim A is to generate tools that will help in reprogramming somatic cells and allow the genetic manipulation of human ES and iPS cells. These tools will be important for aim B which focuses on the mechanism of human somatic cell reprogramming. The goal of aim C is establishing experimental systems to evaluate the potential of human iPS cells to differentiate into functional neuronal cells in vitro as well as in vivo in chimeric mice. Furthermore, we will design protocols to generate iPS cells from human peripheral blood. Finally, the focus of aim D is to screen for chemical compounds as alternatives to activating reprogramming pathways by genetic means.

A. Generation of Tools for the Genetic Manipulation of Human ES and iPS Cells

The ability to genetically alter endogenous genes by homologous recombination has revolutionized biology and, in combination with embryonic stem cells, holds great promise for molecular medicine. Although gene targeting is a routine procedure in mouse ES cells, it has previously been difficult to transfer this technology to human embryonic stem cells [Giudice, 2008 #6863]. Indeed, only 4 publications have appeared reporting successful targeting of an endogenous gene since the first isolation of human ES cells by Thomson 10 years ago [Davis, 2008 #6860; Irion, 2007 #6857; Zwaka, 2003 #6223; Urbach, 2004 #6163]. The difficulties of genetically modifying endogenous genes need to be overcome to realize the full potential of human ES cells.

The focus of this work is to establish tools that will allow for the efficient genetic manipulation of human ES and iPS cells. To produce huES cells carrying marker in lineage specific genes we will use two different approaches, genetically modified human ES cells were created carrying markers in key developmental regulators using conventional homologous recombination. These markers, inserted in lineage specific genes, will be used in subsequent aims for differentiation of iPS cells into specific neuronal lineages. An experimental system that allows for the efficient reprogramming of somatic cells in the absence of retrovirus mediated factor transduction was also developed.

Targeting of Lineage Specific Genes by Homologous Recombination

The derivation of differentiated cells from undifferentiated ES cells is facilitated by markers inserted into lineage specific endogenous genes that can be used for the isolation of a desired differentiated cell type. Our preliminary experiments demonstrated targeting of the OCT4 as well as the COL1A1 locus with GFP or drug resistance markers. Accordingly a goal was to generate ES and iPS cells that carry drug resistance markers and/or GFP (or other detectable marker) sequences in genes that are expressed in cells of the neural or other lineage and can be used for screening or selection of differentiated cell types that are affected in diseases such as Alzheimer's and Parkinson's.

(i) Gene Targeting of Neural Lineage Specific Target Genes by Homologous Recombination:

In contrast to mouse ES cells, human ES cells are usually passaged mechanically using only limited enzymatic digestion as cellular cloning selects for chromosomal aberrations that enhance single cell growth. This as well as the slow growth may be important reasons that gene targeting has been so inefficient in huES cells. Recently, application of the ROCK inhibitor Y-27632 to huES cells has been shown to markedly diminish dissociation-induced apoptosis and to increase cloning efficiency [Watanabe, 2007 #6549]. All experiments will, therefore, be done in the presence of this inhibitor.

For homologous recombination, targeting vectors containing GFP and neo resistance markers separated by 2A sequences will be constructed from isogenic genomic DNA of BGO2 or H9 ES cells using routine procedures. The DNA will be electroporated into the cells following published procedures [Costa, 2007 #6868], and DNA from drug resistant colonies will be isolated and analyzed for correct targeting. We will target genes that are activated at different times during neural differentiation and in different subsets of neurons as detailed below.

SOX1: The transcription factor SOX1 is the earliest known gene that is exclusively expressed in neural precursors of the mouse [Aubert, 2003 #6841]. GFP inserted into this gene will serve as a convenient marker for selecting huES or iPS cell-derived neural precursor cells.

FOXG1: Expression of this gene has been demonstrated in proliferating telencephalic precursor cells and in acetylcholinergic neurons of the basal forebrain [Hebert, 2000 #6844], cells that are affected in Alzheimer's.

PITX3: This homeodomain transcription factor is selectively expressed during terminal differentiation of tyrosine hydroxylase positive neurons and sorting of differentiated ES cells derived from PITX3-GFP transgenic mice has been shown to enrich for dopaminergic neurons [Hedlund, 2008 #6845; Zhao, 2004 #6846].

LMX1: This homeodomain transcription factor appears to be a crucial determinant of proliferating dopaminergic precursor cells [Andersson, 2006 #6840].

The marking of relevant lineage specific genes by GFP has been shown to aid in establishing robust differentiation protocols that allow for the isolation of enriched or even homogeneous populations of differentiated cells. HuES cells carrying GFP in the 4 genes will allow enrichment for precursors as well as more differentiated cells that are relevant for the study of iPS cells derived from patients with diseases such as Alzheimer's or Parkinson's disease.

Figures 10A, 10B, 10C, 10D:
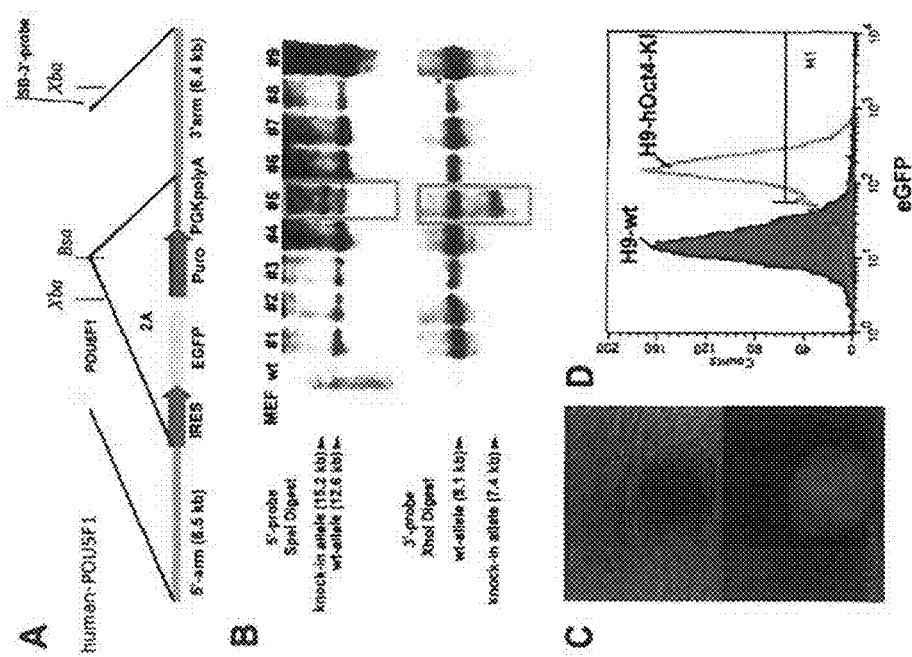
FIG. 10A-10D shows homologous insertion of GFP into the OCT4 locus. H9 huES cells were electroporated with the GFP—puroR gene trap vector targeted to the 3' UTR of the OCT4 locus as shown in FIG. 10A. A correctly targeted clones, identified by Southern analysis (FIG. 10B) stained for GFP and was puro resistant (FIGS. 10C, 10D) when undifferentiated but the marker and drug resistance genes were silenced when differentiated (not shown).

The difficulty of establishing efficient methods of homologous recombination has greatly impeded the utility of the huES cell system. Preliminary data are encouraging and demonstrate that two endogenous loci, OCT4 and COL1A1, have been targeted with GFP and puromycin resistance cDNAs (FIG. 10). However, so far only genes that are expressed in ES cells (OCT4, HPRT, ROSA26 [Irion, 2007 #6857; Zwaka, 2003 #6223; Urbach, 2004 #6163]) or that are poised to be expressed such as MOXL1 [Davis, 2008 #6860] have been targeted in human ES cells. Also, the COL1A1 locus is highly recombinogenic in mouse cells [Beard, 2006 #6199] and targeting of this locus may not be representative of other non-expressed genes. Thus, because our intent is to target non-expressed genes by homologous recombination, this aim poses a challenge.

"Secondary" iPS Cells Carrying Different Combinations of Reprogramming Factors

We have shown that mouse iPS cells may carry 15 or more proviral inserts [Wernig, 2007 #6641] suggesting a strong selection for the small fraction of cells that harbor multiple copies of each vector to achieve high levels or a certain stoichiometry of factor expression required for the initiation of the reprogramming process. Described herein is a system that circumvents the need for viral transduction and thus eliminates the necessity to select for the small fraction of cells carrying the "right" combination of proviruses. Indeed, the generation of "secondary" fibroblasts that were clonally derived from "primary" iPS cells and carried the appropriate number of DOX inducible proviruses that had achieved reprogramming in the first place allowed us to reprogram mature B cells to a pluripotent state [Hanna, 2008 #6842]. This approach was adapted to human cells and generated secondary fibroblasts that carry the reprogramming factors (i) either as proviral vectors integrated into pre-selected chromosomal positions or (ii) inserted by homologous recombination into a genomic expression locus. This system can be used to determine the mechanisms of reprogramming and to screen for small molecules that enhance reprogramming or replace any of the factors.

Figures 23A, 23B:
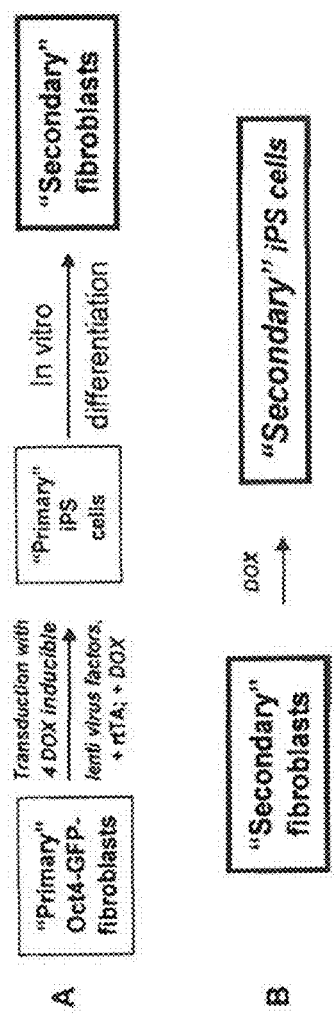
FIGS. 23A-23B show generation of secondary fibroblasts carrying DOX inducible vectors, permitting reprogramming without viral transduction.

(i). Secondary fibroblasts carrying pre-selected proviruses: To pre-select for cells that carry the "right" combination and number of retroviral copies, a two-step protocol may be utilized. FIGS. 23A-23B outline the approach, which follows the same logic utilized to reprogram mouse B cells into iPS cells [Hanna, 2008 #6842]. First, ES or iPS cells carrying the GFP marker in the OCT4 gene as well as a lentivirus transduced tet rtTA transactivator will be differentiated into fibroblasts. These "primary" fibroblasts will be transduced with all four factors using DOX inducible vectors and cultured in the presence of DOX and screened for OCT4 activation to isolate reprogrammed "primary" iPS cells. These iPS cells will be differentiated in the absence of DOX to generate "secondary" fibroblasts (FIG. 23A). The rationale for this approach is that secondary fibroblasts carry the "right" combination of vector copies because they were selected as "primary" iPS cells in the first step. These secondary fibroblasts are genetically homogenous since they arise from a single iPS colony. Upon addition of DOX to such cultures the integrated vectors will be reactivated resulting in the consistent generation of "secondary" iPS cells without requiring the new transduction of factors (FIG. 23B). This can be used to generate human secondary iPS cells (or mouse, monkey, etc.), without going through the process of generating an animal from the primary iPS cell. Alternatively, DOX inducible polycistronic vectors (FIG. 13A-13C) can be used instead of the single-factor vectors for the generation of primary iPS cells.

Figure 24:
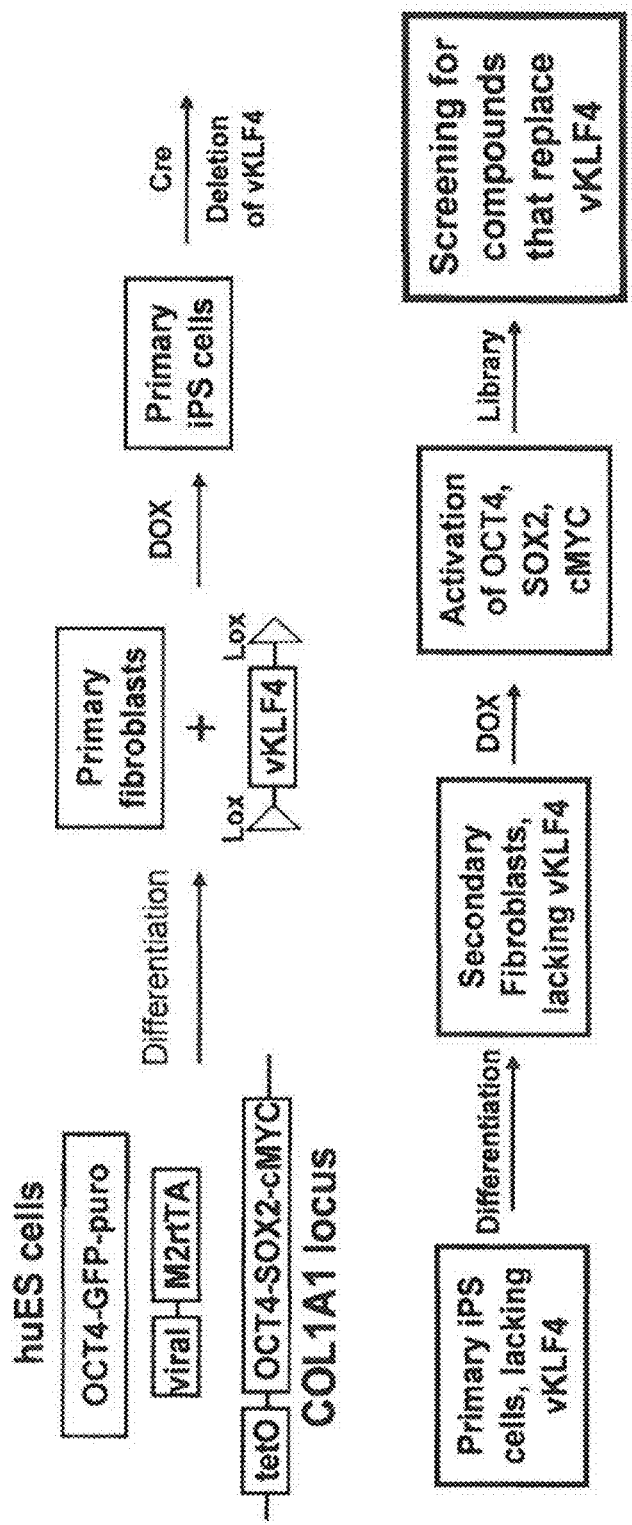
FIG. 24 shows reprogramming without vector-mediated factor transduction. Primary fibroblasts will be derived from huES cells carrying the OCT4-GFP marker, the tet transactivator M2rtTA, and the DOX inducible polycistronic construct expressing 3 reprogramming factors (in this example OCT4, SOX2, cMYC) described in FIG. 13 inserted into the COL1A1 locus. The cells will be infected with a vector flanked by 2Lox sites (Ventura et al., *Proc Natl Acad Sci USA*, July 13; 101(28):10380-5 (2004)) carrying the KF4. cDNA. DOX treatment will generate primary iPS cells which, after Cre expression, will delete the KLF4 vector. Secondary fibroblasts will be derived that, upon DOX treatment, will allow screening for small molecules that replace the deleted KLF4 factor.
Figure 25:
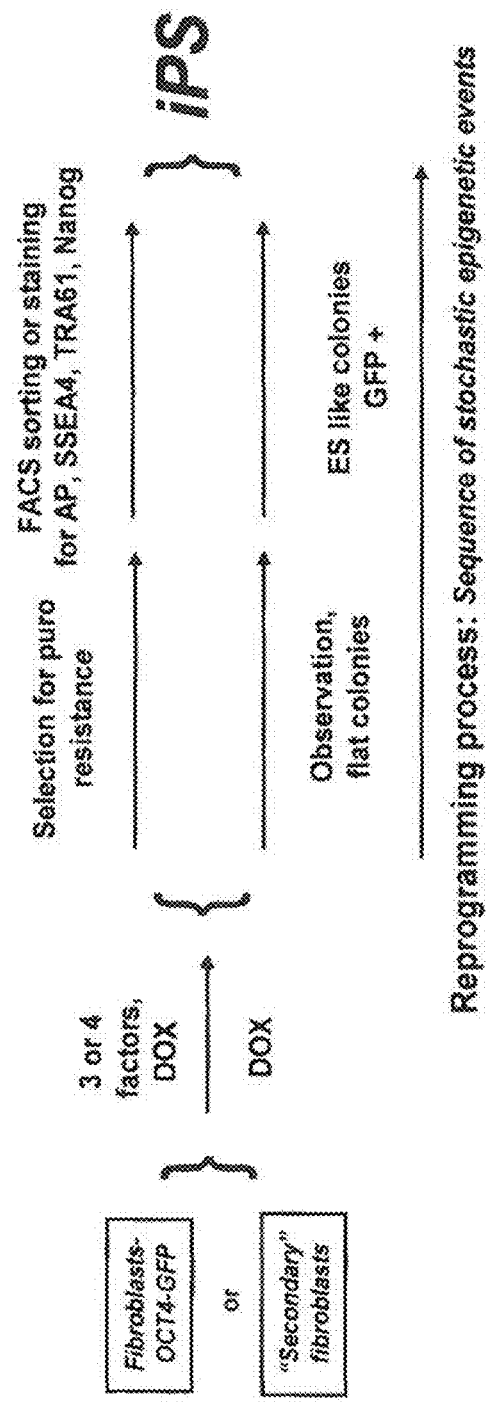
FIG. 25 shows a scheme for quantifying the efficiency of reprogramming by testing for different markers. Cells carrying the GFP and puro marker in the OCT4 locus were transduced with 3 or 4 factors. The fraction of drug resistant or GFP positive colonies and the appearance of cells that stain for alkaline phosphatase (AP), SSEA4, TRA61 or Nanog were determined in cell populations at different times after infection.

(ii). Secondary fibroblasts carrying reprogramming factors in the COL1A1 locus: In an effort to avoid all retrovirus infection secondary fibroblasts that carry all reprogramming factors in the COL1A1 locus or other non-essential locus such as ROSA26 or AAVS1 locus (a specific locus into which Adeno-associated virus (AAV) integrates) are produced. In mouse ES cells we have shown that the Col1a1 locus can be efficiently targeted resulting in reproducible ubiquitous or inducible expression of inserted transgenes [Beard, 2006 #6199; Hochedlinger, 2005 #5758]. Reporter cells will be constructed that carry, in addition to the Dox inducible rtTA transactivator and the OCT4 GFP reporter a polycistronic vector inserted into the COL1A1 locus encoding all or a subset of the reprogramming factors under the control of the tet operator (FIG. 24). In this illustration, OCT4, SOX2 and cMYC have been inserted into the COL1A1 locus. Primary fibroblasts will be derived in vitro and will be infected with a KLF4 virus flanked by two Lox sites. Primary iPS cells will be selected as above with the three factors being induced by DOX, the KLF4 virus will be deleted by Cre transduction [Hanna, 2007 #6781] and secondary fibroblasts lacking vKLF4 will be derived by in vitro differentiation. These cells can be screened for small molecules that replace the need for KLF4 in reprogramming (see later, Aim D) or for streamlining transient transfection protocols (Aim B.2, 4).

Reprogramming selects for the small fraction of iPS cells that carry a high number of proviral insertions. The experiments proposed in this aim seek to establish an experimental system that allows a more efficient and reproducible reprogramming as the process would be independent of random proviral insertions that select the rare iPS cells. The goal is to generate secondary fibroblasts that carry any combination of 2 or 3 DOX inducible factors and thus would allow screening for small molecules that replace the missing factor(s) for our aim to screen for small molecules that can enhance or induce reprogramming (Aim D). Also, this system will be important for studying the molecular mechanisms of reprogramming (Aim B.4).

B. In Vitro Reprogramming of Somatic Human Cells

The DOX inducible lentivirus system has been used to define the reprogramming kinetics of mouse fibroblasts. Work described herein uses the tools described above to determine the kinetics and minimal vector expression for reprogramming of human somatic cells. Furthermore, we will develop methods of reprogramming that would minimize or circumvent genetic alterations and we will use insertional mutagenesis to isolate additional genes that enhance reprogramming. Finally, we will define the epigenetic state of iPS cells as well as of intermediate stages of reprogramming.

C. Developmental Potential and Derivation from Blood Donor Cells

The most important application of patient specific iPS cells is their potential use in studying complex human diseases in the test tube. For this application robust experimental approaches need to be established before this technology can be used in a clinical setting. Work described herein establishes procedures that allow the reproducible in vitro differentiation of iPS and huES cells and the evaluation of the in vivo potential of iPS cells. Isolation of iPS cells from peripheral human blood samples may also be performed.

3. B Cells, T Cells and Macrophages as Donors

It is of interest to directly reprogram cells obtained from peripheral blood samples instead of from deep skin biopsies, as this would facilitate generating patient specific iPS cells in a clinical setting. We have recently shown that immature and mature mouse B cells can efficiently be reprogrammed to pluripotent iPS cells and that these cells carried the donor cell specific genetic rearrangements of the immunoglobulin locus [Hanna, 2008 #6842]. Surprisingly, the efficiency of reprogramming mature mouse B cells was 3%, which is substantially higher than that of adult fibroblasts or MEFs. This aim will seek to adapt the methods used for reprogramming of mouse lymphoid cells to human peripheral blood samples.

Donor cells: Transduction with the c/EBPa transcription factor was required to render mature mouse B cells susceptible to the action of the four reprogramming factors [Hanna, 2008 #6842]. We will isolate various cell populations from human peripheral blood and test their susceptibility to reprogramming.

(i) B and T cells: In an effort to adapt the protocol for mouse B cell reprogramming we will use established procedures to stimulate proliferation of B and T cells [Mercier-Letondal, 2008 #6855] and infect the cells with vectors transducing c/EBPa and the tet rtTA transactivator. After a few days of culture in cytokines the cells will be transduced with the four DOX inducible reprogramming factors OCT4, SOX2, C-MYC and KLF4 and cultured in ES cell medium. Reprogrammed colonies will be isolated by morphology and tested for the expression of pluripotency markers such as TRA160, SSEA3/4, NANOG and OCT4. To verify the donor cell origin of the iPS cells we will analyze genomic DNA for the presence of Ig or TCR rearrangements.

(ii) Monocytes: Our results with mouse suggested that an intermediate step in the reprogramming of mature B cells might be a macrophage-like cell [Hanna, 2008 #6842]. Monocytes will be isolated from buffy coats of human volunteers by Ficoll gradient centrifugation and adherent cells will be collected. The cells will be grown in IL4 and GM-CSF following established procedures [Damaj, 2007 #6854]. We will then transduce the cells with the four factors OCT4, SOX2, cMYC and KLF4 as above and continue cultivation in ES cell medium in the presence of DOX. Colonies with iPS morphology will be picked and analyzed for the expression of pluripotency markers as above. The developmental potential of the blood-derived iPS cells will be assessed by standard procedures such as teratoma formation and in vitro differentiation.

Presently, the strategy of isolating patient specific iPS cells envisions the reprogramming of donor cells derived from deep skin biopsies, a procedure that is more complex and painful than collecting blood. For the routine clinical application it would be of obvious interest to design reproducible protocols for the routine isolation of patient specific iPS cells from peripheral blood samples. We anticipate that the proposed experiments will help in establishing such protocols.

Given the ease and efficiency of mouse B cell reprogramming we are encouraged that this protocol should also be effective in reprogramming human peripheral blood derived cells. Because B or T cell-derived iPS cells would carry genetic rearrangements at the Ig or TCR locus, respectively, it may be advantageous for potential therapeutic applications to use macrophages or monocytes as donors as they would harbor no genetic changes. Although we do not know the mechanism that causes c/EBPalpha to render mature B cells susceptible to reprogramming by OCT4, SOX2, cMYC and KLF4, it may involve the conversion of B cell identity to that of macrophages [Xie, 2004 #5447]. These considerations suggest that deriving iPS cells from human monocytes may be straightforward. However, if the procedures developed in the mouse fail to yield blood derived human iPS cells, we will screen for additional factors using established approaches.

D. Screen for Small Molecules

The induction of reprogramming by retroviral vector mediated gene transfer, in particular the transduction of oncogenes, represents a serious impediment to the eventual therapeutic application of this approach. For example, we and others [Okita, 2007 #6542] have seen that tumors form in chimeras produced with iPS cells due to v-myc c-Myc activation. It is, therefore, of interest to identify small molecules that would either improve reprogramming efficiency or would activate a relevant pathway and thus could replace the need for expressing a given factor such as C-MYC or KLF4. The goal of this aim is to establish high-throughput cell-based assay systems to screen chemical libraries for such compounds.

D.1 Experimental Design and Reporter Cells for Small Molecule Library Screens

To detect reprogramming in a high-throughput screen we need cells carrying a marker such as GFP inserted into the endogenous OCT4 or NANOG locus. Such cells will not express the marker but can be used to screen for compounds that activate either of the endogenous genes.

For setting up a high-throughput screen for reprogramming we consider two major constraints that limit the experimental design.

Heterogeneous cell population: Arguably, the most critical limitation is that transduction of fibroblasts with the four factors will produce a genetically heterogeneous population of cells. As discussed above in V.A.3, it is likely that only the small fraction of infected cells that carry a specific number of viral vectors generating the "right" expression level or the "right" combination of expression levels of the four factors are the ones that are being selected when screening for reprogramming. Thus, infected cells in individual wells will differ with respect to viral integration and viral copy numbers precluding a meaningful comparison of wells exposed to different compounds in a screen.

Frequency of marker activation, sensitivity and time constraints of assay: Another important consideration for setting up the screen concerns the sensitivity of the detection system: how many cells need to express the OCT4-GFP reporter gene to be detectable in a given well? Reporter gene expression is an important constraint as the fraction of reprogrammed cells needs to be high enough to produce at least a single detectable reprogramming event in a well with an active compound. Furthermore, reprogrammed cells appear in a population of fibroblasts only 3 to 5 weeks after infection with the four factors. Thus, the infected cells need to survive and proliferate in 96- or 384-well formats for this time period, which limits the number of cells that can be plated.

To overcome these limitations we will generate fibroblast populations that are genetically homogenous because they (i) carry the identical number of vector integrations or (ii) carry various combinations of reprogramming factors inserted into an endogenous expression locus by homologous recombination.

(i). "Secondary" clonal fibroblasts that carry a specific and predetermined combination of proviruses: We have recently shown that "secondary" mouse iPS cells can be derived from "primary" iPS cells that had been generated by infection of fibroblasts with DOX inducible lentiviruses transducing the four transcription factors Oct4, Sox2, c-myc and Klf4 [Hanna, 2008 #6842]. Because the "right" combination and number of proviral copies was carried in the "secondary" fibroblasts, no viral infection was needed to induce reprogramming of B cells to secondary iPS cells.

We will follow a similar protocol to pre-select for cells that carry the "right" combination and number of retroviral copies. As shown in FIG. 23A-23B, "secondary" fibroblasts will be derived from "primary" iPS cells by in vitro differentiation without DOX. Instead of using vectors that transduce a single factor we will alternatively use a polycistronic construct as described in FIGS. 13A-13C and 14A-14E for transduction of different combinations of factors. As outlined in VI.A.3, this approach of using "secondary" fibroblasts or B cells resulted in efficient and DOX dependent activation of the reprogramming factors leading to iPS formation without requiring any additional virus infections [Hanna, 2008 #6842]. To assess the fraction of iPS cells that arise upon DOX addition we will plate 500 to 1000 cells per well of 96-well plates and about 100 cells per well in 384-well plates and assess the fraction of GFP positive cells. The results in the mouse system indicated that secondary iPS cells arise only two to three weeks after DOX induction.

Because the cells can be cultured for only about 7 days in 96- or 384-well plates we will pre-treat the secondary fibroblasts with DOX for different times prior to plating.

(ii). Transgenic fibroblasts that carry DOX-inducible reprogramming factors in the COL1A1 locus: We have shown that transgenes inserted into the Col1a1 locus are highly expressed in transgenic mice and, if under the control of the tet operator, are reproducibly activated in all tissues upon DOX application [Beard, 2006 #6199; Hochedlinger, 2005 #5758]. We will insert polycistronic constructs expressing different combinations of 3 or of all four reprogramming factors under the control of the tet operator into the COL1A1 locus of huES cells carrying the GFP marker in the OCT4 locus (FIG. 10). In addition, the cells will be infected with a lentivirus vector transducing the rtTA transactivator. The cells will be differentiated into secondary fibroblasts that can be screened for compounds that enhance reprogramming or replace a given factor (see later, FIG. 24).

D.2 Screen for Compounds that Enhance Reprogramming Efficiency

To screen for compounds that increase reprogramming efficiency we will culture secondary iPS cells carrying the "right" combination of all four factors or fibroblasts carrying all four factors in the COL1A1 locus in the presence of DOX (FIG. 24). In preliminary experiments we will determine the fraction of GFP positive cells that can be detected in the screens. Given that the fraction of reprogrammed cells arising from fibroblasts transduced with the four factors is low it may be difficult or impossible to detect a single reprogrammed cell in the 1000 or 100 cells that can be plated per 96- or 384-well plate, respectively, unless a given compound would significantly increase the fraction of reprogrammed cells. The assay has, however, a very low background that compensates for the inherently low signal.

In pilot screens we will test the fraction of GFP positive cells arising in the four factor reporter cells, which are cultured in the presence of DOX and have or have not been treated with 5-azadC or infected with the DNMT1 siRNA vector, both of which will decrease global DNA methylation levels, a treatment which has been shown to enhance reprogramming of mouse fibroblasts [Mikkelsen, 2008 #6891]. The fraction of GFP positive cells under any of these conditions will determine how many cells need to be plated per well to detect a compound that enhances the fraction of GFP positive cells in a less stringent screen. A more stringent screen would use cells that have not been treated with 5-azadC or infected with the DNMT1 siRNA vector as this would monitor non-sensitized cells for compounds that more efficiently activate the reporter than above.

D.3 Screen for Compounds that Replace any of the Four Factors

To screen for compounds that could replace any of the retrovirus transduced factors we will transduce cells with vectors that can be independently regulated. The concept of the approach is that 3 factors will be under the control of one inducible system and the fourth factor under independent inducible control. We will use two different strategies to produce the cells used for screening.

Figure 26:
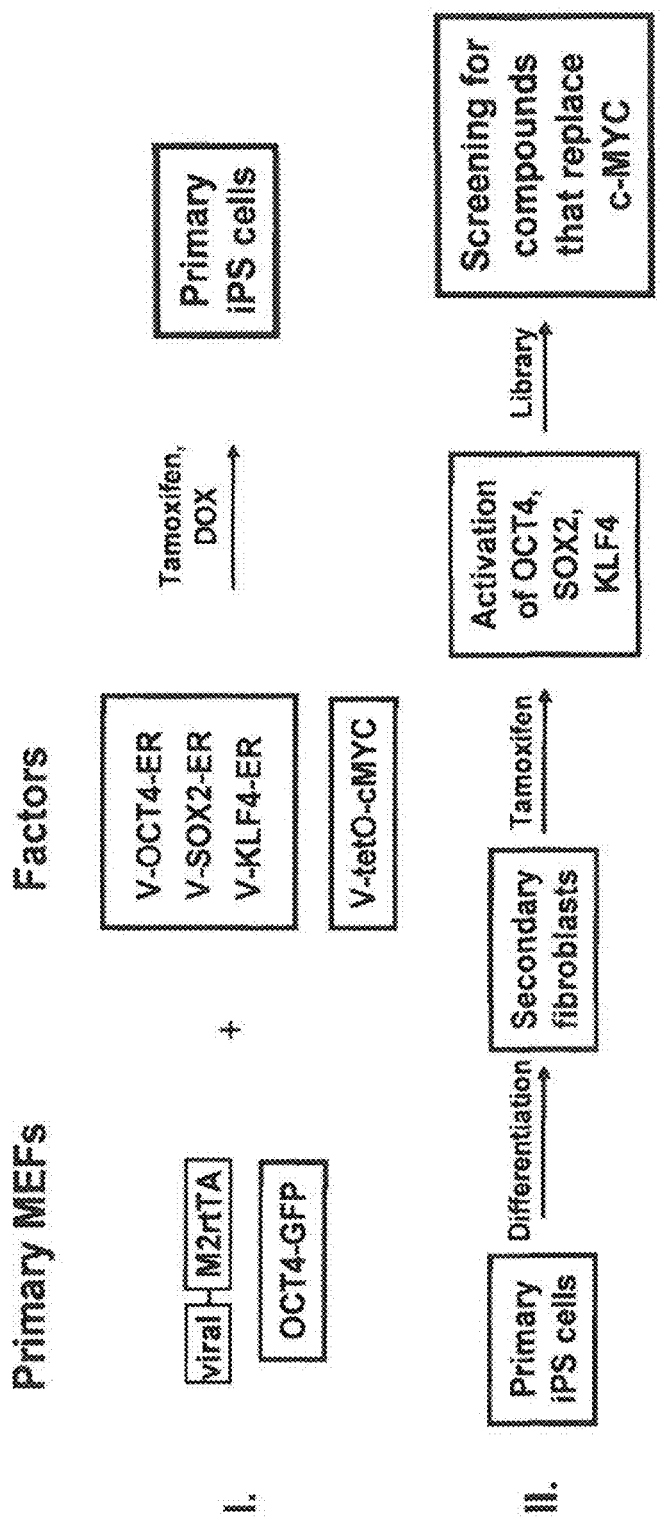
FIG. 26 illustrates screening for small molecules using secondary fibroblasts with factors that can be independently induced. Primary fibroblasts carrying the viral M2rtTA and the OCT4-GFP marker will be transduced with tamoxifen inducible vectors transducing 3 factors and with a DOX inducible vector transducing the 4th factor (in this case cMYC). Primary iPS cells will be derived by culture in tamoxifen and DOX and secondary fibroblasts will be derived. These cells, when cultured in tamoxifen, can be screened for small molecules that replace cMYC for reprogramming to secondary iPS cells.

(i) Tamoxifen inducible vectors: We have generated vectors transducing OCT4, SOX2, KLF4 and C-MYC estrogen receptor (ER) fusion constructs [Grandori, 1996 #6505] whose expression is activated by the addition of tamoxifen to the medium (FIG. 11B). As outlined in FIG. 26, OCT4-GFP reporter primary fibroblasts will be transduced with retroviruses expressing three tamoxifen inducible factors with the fourth factor expressed from a DOX dependent vector. The infected cells will be grown in medium containing tamoxifen and DOX and "primary" iPS cells will be selected by screening for GFP expression. As described above, secondary fibroblasts will be derived, exposed to tamoxifen to activate the three tamoxifen-dependent factors and will be screened for small molecule compounds that activate the GFP reporter in the absence of DOX and cMYC expression.

(ii) Transgenic fibroblasts carrying different combinations of factors in the COL1A1 locus: We will pursue an alternative strategy that avoids retroviral infection as outlined in FIG. 24. Primary fibroblasts will be derived from huES cells carrying in addition to the OCT4-GFP marker and a virus transduced tet M2rtTA transactivator a polycistronic construct encoding any combination of three reprogramming factors in the COL1A1 locus [Beard, 2006 #6199; Hochedlinger, 2005 #5758]; compare FIG. 13A-13C, 14A-14E). The fibroblasts will be transduced with a Lox flanked vector carrying the missing $4^{th}$ factor (KLF4 in FIG. 24) and primary iPS cells will be derived. After Cre transduction to delete the KLF4 vector secondary fibroblasts will be derived. DOX exposure will activate the three DOX dependent factors inserted into the COL1A1 locus and the cells will be screened for small molecules that activate the GFP reporter in the absence of the missing $4^{th}$ factor (in this case KLF4). To sensitize the screen we will use cells that have been treated with 5-aza-dC.

D.4 Screening Platforms

The screening of small molecule libraries will be performed in collaboration with the laboratory of S. Ding at Scripps (see letter by S. Ding). For example, the Ding laboratory has developed and optimized cell-based phenotypic high throughput screens [Xu, 2008 #6875] and identified the small molecule pluripotin that sustains self renewal of ES cells in chemically defined medium and in the absence of LIF [Chen, 2006 #6871]. The screen was based upon the expression of an Oct4 promoter driven GFP marker. We will screen the OCT4-GFP transgenic fibroblasts carrying the different combinations of factors as described above for GFP activation.

The activity of any compounds that score positive in the screens will be verified under defined culture conditions. A major issue will be to investigate the molecular pathways that are involved in the reprogramming process.

Possible outcome and interpretation: We expect that the screen for activation of the OCT4 gene will identify compounds that facilitate the transition from a somatic epigenetic state to one that is characteristic of pluripotent cells and thus render the reprogramming process more efficient. Another important goal of these experiments is to find small molecule compounds that could replace the need for genetic manipulations involving transduction of genes encoding oncogenes such as cMYC, OCT4 or KLF4.

The two most significant potential problems for a high-throughput screen are (i) the time required for reprogramming to take place and (ii) whether a rare reprogramming event can be detected in the limited number of cells that can be plated per well of a 96 or 384 well plate. As discussed above, we will precondition the cells to carry the "right" number and combination of factors and further sensitize the cells to increase the frequency of reprogramming-induced activation of the various reporter genes. Once compounds have been identified which increase reprogramming efficiency they will be used as sensitizers in subsequent screens for additional compounds that could further enhance iPS cell formation.

Significance: The present strategies to induce reprogramming rely on the transduction of powerful oncogenes, a stumbling block to any therapeutic application. This goal seeks to identify small molecules that could activate relevant pathways and thus would improve efficiency and possibly minimize the genetic alterations required for inducing reprogramming.

Significance and Long Term Implications

The method of the in vitro generation of pluripotent iPS cells promises to revolutionize the study of complex human diseases and has significant implications for the eventual treatment of degenerative diseases. In vitro reprogramming of mouse somatic cells to a pluripotent state has been shown to be reasonably efficient and the underlying molecular mechanisms of this process are being actively studied. However, reprogramming of human cells has proved to be more laborious and difficult and major technical issues need to be resolved before this technology could be adapted for clinical use. Work described herein seeks to define the molecular mechanisms that bring about the conversion of human somatic cells to a pluripotent state, to devise strategies for assessing the developmental potential of human iPS cells and to achieve reprogramming without the need for genetic manipulation. Work described herein will contribute to solving some of the crucial obstacles that presently hamper the application of the technology to study human diseases and to its eventual use for transplantation therapy of degenerative diseases.

Example 3

Reprogramming of Murine and Human Somatic Cells Using a Single Polycistronic Vector Materials and Methods
Viral Preparation and Infection.

Construction of 4F2A lentiviral vectors containing Oct4, Sox2, Klf4, and c-Myc under control of the tetracycline operator and a minimal CMV promoter was generated after EcoRI cloning from a FUW lentivirus backbone. All constructs were generated using unique restriction sites after amplification by PCR to place an individual factor between a respective 2A peptide ($1^{st}$ XbaI-NheI; $2^{nd}$ SphI; $3^{rd}$ XhoI; $4^{th}$ AscI). Respective 2A sequences:

```
                                       (SEQ ID NO: 21)
P2A-GCCACGAACTTCTCTCTGTTAAAGCAAGCAGGAGATGTTGAAGAA

AACCCCGGGCCT;

(SEQ ID NO: 22)
T2A-GAGGGCAGAGGAAGTCTTCTAACATGCGGTGACGTGGAGGAGAAT

CCCGGCCCT;

(SEQ ID NO: 23)
E2A-CAGTGTACTAATTATGCTCTCTTGAAATTGGCTGGAGATGTTGAG

AGCAACCCAGGTCCC.
```

Replication-incompetent lentiviral particles (4F2A and M2rtTA) were packaged in 293T cells with a VSV-G coat and used to infect MEFs containing a GFP allele targeted to the endogenous Nanog locus (25) (7). 14-week old tail tip fibroblasts were derived from mice previously published (12). Human keratinocytes (NHFK) were obtained from Coriell Institute for Medical Research Camden, N.J. Viral supernatants from cultures packaging each of the two viruses were pooled, filtered through a 0.45 muM filter and subjected to ultracentrifugation for concentration. Virus pellets were resuspended in ES cell medium (DMEM supplemented with 10% FBS (Hyclone), leukemia inhibitory factor, β-mercaptoethanol (Sigma-Aldrich), penicillin/streptomycin, L-glutamine and nonessential amino acids (all from Invitrogen) before being applied to cells for 24 hours.

Western Blot

100 µl of lysis buffer containing 2% SDS, 10 mM dithiothreitol, 10% glycerol, 12% urea, 10 mM Tris-HCl (pH 7.5), 1 mM phenylmethylsulfonyl fluoride, 1× protease inhibitor mixture (Roche), 25 µM MG132 proteosome inhibitor, and boiled for 5 min. Proteins were then quantified using Bradford reagent (Pierce) and taking spectrophotometric readings at 590 nm. Concentrations were estimated against a standard curve generated using bovine serum albumin. Total protein (5 µg) was subjected to electrophoreses in a denaturing 10% polyacrylamide gel containing 10% SDS. Proteins were then transferred onto Immobilon-P membranes (Millipore) using a semi-dry transfer apparatus. Membranes were blocked in PBS, 0.01% Tween 20 containing 2% nonfat powdered milk (Bio-Rad). Proteins were detected by incubating with antibodies at a concentration of 50 ng/ml in blocking solution. Antibodies used were Oct4 (h-134 Santa Cruz Biotechnology); Sox2 (mouse monoclonal R&D Biosystems); c-Myc (06-340 Upstate); Klf4 (H-180 Santa Cruz Biotechnology); GAPDH (sc-25778 Santa Cruz Biotechnology).

Quantitative RT-PCR

Total RNA was isolated using Trizol reagent (Invitrogen). Five micrograms of total RNA was treated with DNase I to remove potential contamination of genomic DNA using a DNA Free RNA kit (Zymo Research). One microgram of DNase I—treated RNA was reverse transcribed using a First Strand Synthesis kit (Invitrogen) and ultimately resuspended in 100 mul of water. Quantitative PCR analysis was performed in triplicate using ⅟₅₀ of the reverse transcription reaction in an ABI Prism 7000 (Applied Biosystems) with Platinum SYBR green qPCR SuperMix-UDG with ROX (Invitrogen). Equal loading was achieved by amplifying GAPDH mRNA and all reactions were performed in triplicate. Primers used for amplification were as follows:

```
Oct4
F, 5'-ACATCGCCAATCAGCTTGG-3'     (SEQ ID NO: 24)
and

R, 5'-AGAACCATACTCGAACCACATCC-3' (SEQ ID NO: 25)

Sox2
F, 5'-ACAGATGCAACCGATGCACC-3'    (SEQ ID NO: 26)
and

R, 5'-TGGAGTTGTACTGCAGGGCG-3'    (SEQ ID NO: 27)

4F2A (E2A-cMyc)
F, 5'-GGCTGGAGATGTTGAGAGCAA-3'   (SEQ ID NO: 28)
and

R, 5'-AAAGGAAATCCAGTGGCGC-3'     (SEQ ID NO: 29)

GAPDH
F, 5'-TTCACCACCATGGAGAAGGC-3'    (SEQ ID NO: 30)
and

R, 5'-CCCTTTTGGCTCCACCCT-3'      (SEQ ID NO: 31)
```

Error bars represent s.d. of the mean of triplicate reactions.

Southern Blotting

10 µg of BamHI digested genomic DNA was separated on a 0.7% agarose gel, transferred to a nylon membrane (Amersham) and hybridized with $^{32}$P random primer (Stratagene) labeled probes for OCT4 (EcoRI-PstI fragment of pFUW-tetO-OCT4 plasmid), KLF4 (full length KLF4 cDNA), c-MYC (full length c-MYC cDNA) and SOX2 (full length fragment of pFUW-tetO-SOX2 plasmid).

Immunofluorescent Staining

Cells were fixed in 4% paraformaldehyde for 20 minutes at 25° C., washed 3 times with PBS and blocked for 15 min with 5% FBS in PBS containing 0.1% Triton-X. After incubation with primary antibodies against Oct4 (Santa Cruz h-134), Sox2 (R&D Biosystems), Nanog (anti-ms R&D and anti-h), Tra-1-60, (mouse monoclonal, Chemicon International); hNANOG (goat polyclonal R&D Systems); mNANOG (Bethyl A300-398A), Tra1-81 (mouse monoclonal, Chemicon International), SSEA4 and SSEA1 (monoclonal mouse, Developmental Studies Hybridoma Bank) for 1 h in 1% FBS in PBS containing 0.1% Triton-X, cells were washed 3 times with PBS and incubated with fluorophore-labeled appropriate secondary antibodies purchased from Jackson Immunoresearch. Specimens were analyzed on an Olympus Fluorescence microscope and images were acquired with a Zeiss Axiocam camera.

Mouse Chimera and Teratoma Formation

Diploid blastocysts (94-98 h after hCG injection) were placed in a drop of Hepes-CZB medium under mineral oil. A flat tip microinjection pipette with an internal diameter of 16 μm was used for iPS cell injections. Each blastocyst received 8-10 iPS cells. After injection, blastocysts were cultured in potassium simplex optimization medium (KSOM) and placed at 37° C. until transferred to recipient females. About 10 injected blastocysts were transferred to each uterine horn of 2.5-day-postcoitum pseudo-pregnant B6D2F1 female. Pups were recovered at day 19.5 and fostered to lactating B6D2F1 mothers when necessary. Teratoma formation was performed by depositing $2 \times 10^6$ cells under the flanks of recipient SCID or Rag2−/− mice. Tumors were isolated 3-6 weeks later for histological analysis.

Human Teratoma Formation and Analysis hiPSCs were collected by collagenase treatment (1.5 mg/ml) and separated from feeder cells by subsequent washes with medium and sedimentation of iPSC colonies. iPSC aggregates were collected by centrifugation and resuspended in a ratio of $10^6$ cells in 250 μl of iPSC culture media. iPSCs were injected subcutaneously by 21 gauge needle in the back of SCID mice (Taconic). A tumor developed within 6 weeks and the animal was sacrificed before tumor size exceeded 1.5 cm in diameter. Teratomas were isolated after sacrificing the mice and fixed in formalin. After sectioning, teratomas were diagnosed base on hematoxylin and eosin staining. Karyotype analysis was done with CLGenetics (Madison, Wis.).

In Vitro Differentiation of Human iPS Cells into Neuronal Progenitors:

Human keratinocyte iPS cells were allowed to outgrow in culture without passing for 2 weeks with daily medium change. At day 15 after passage distinct neural rossets were observed and picked mechanically by pooled glass pipette (26). Rosettes were replated on dishes precoated with 15 μg/ml polyornithine/10 μg/ml of laminin (Po/Lam) in N2B27 medium supplemented with FGF2 (20 ng/ml) EGF (20 ng/ml) (All R&D Systems). After 5-7 d cells were dissociated by scraping with cell lifter and pippeting to single cells in N2B27 medium and replated to Po/Lam culture dishes.

Differentiation and Immunocytochemistry

Induction of differentiation of neural progenitors was performed by withdrawal of FGF2 and EGF from culture medium for 5 days. Cells were fixed in 4% paraformaldehyde for 20 min and stained for human nestin (Chemicon; 1:100) and Tuj-1 (1:100) and subsequently washed 3 times with PBS and incubated with fluorophore-labeled appropriate secondary antibodies purchased from Jackson Immunoresearch. Specimens were analyzed on an Olympus Fluorescence microscope and images were acquired with a Zeiss Axiocam camera.

Results

Figure 13B:
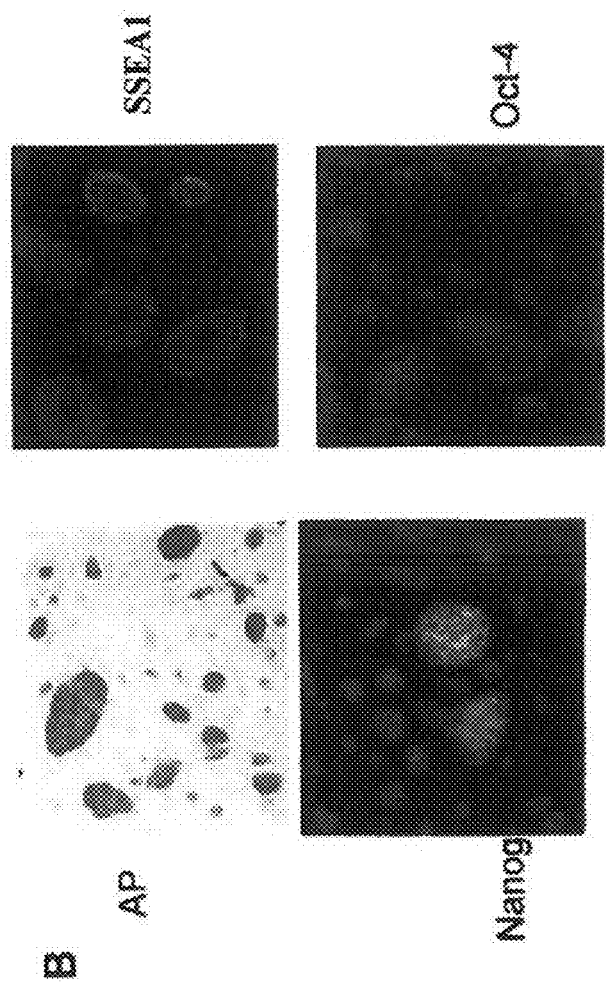
Figures 14A, 14B, 14C, 14D, 14E:
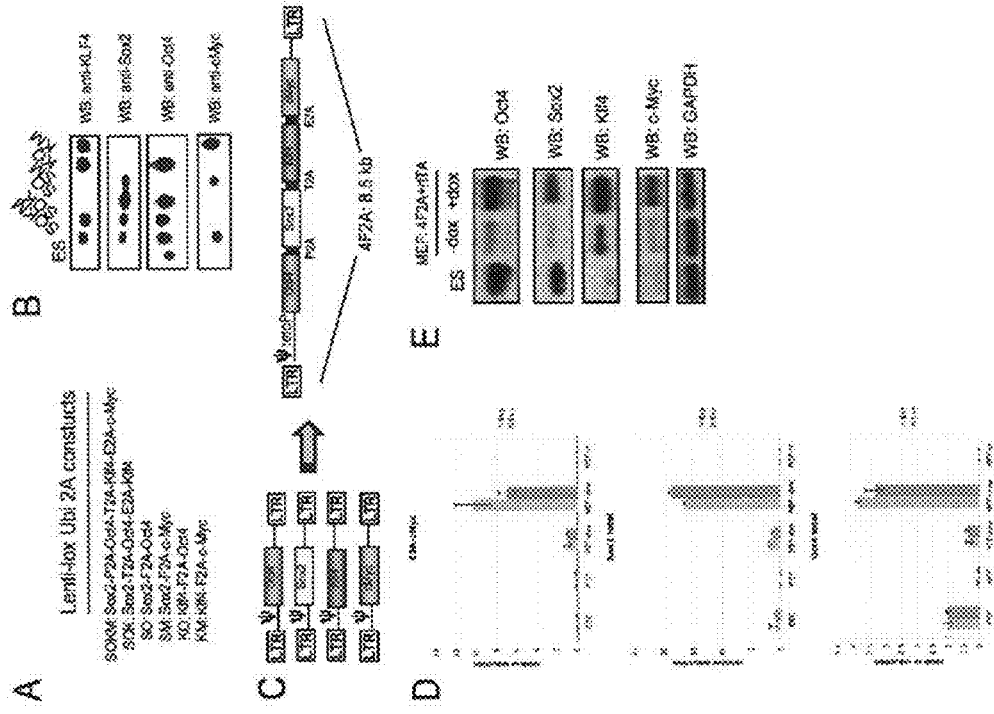
FIGS. 14A-14E show generation of murine iPS cells using a single 4F2A polycistronic virus.

Vectors were constructed with different combinations of two, three, or all four reprogramming factors from one promoter. The goal was to generate polycistronic viral vectors that would express multiple reprogramming genes from a single promoter using 2A peptides. For this one, two, or three 2A oligopeptides containing unique restriction sites were ligated into FUW lentivirus (18) backbones to allow efficient cloning of Oct4, Sox2, c-Myc and Klf4 each separated by a different 2A sequence. Vectors carrying four, three or two factors consecutively with different combinations of F2A, T2A, E2A or P2A sequences (FIGS. 13A and 14A) were tested for their ability to express individual factors by transient transfection in human 293 cells. Western blot analysis demonstrated that 2A peptides support efficient expression of two, three or all four cistrons from a single polycistronic vector (FIG. 14B).

Figure 13C:
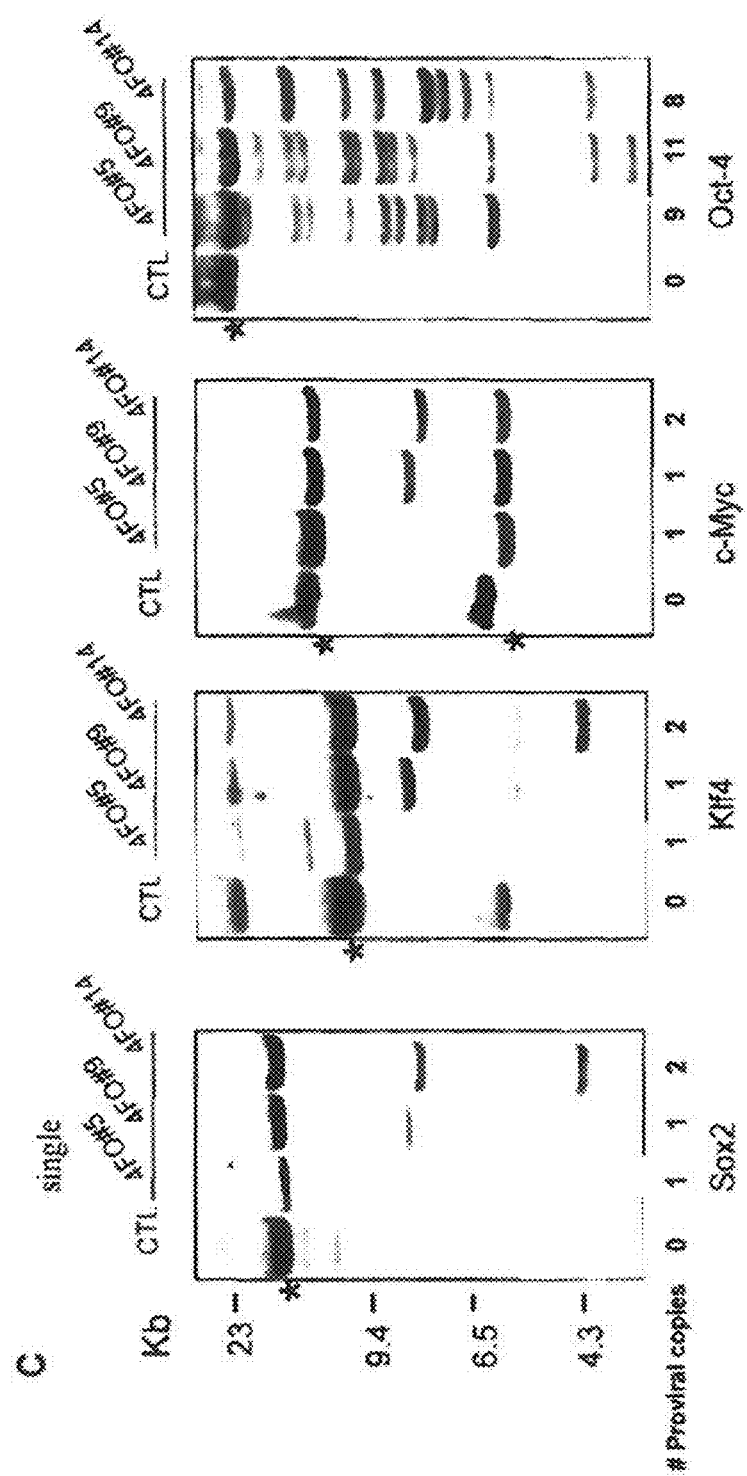

To test the utility of polycistronic vectors for reprogramming we initially transduced retroviral vectors carrying different combinations of 2 or 3 reprogramming factors into MEFs and showed that these constructs were able to generate iPS cells in combination with vectors carrying the additional single factor-cDNA(s). Importantly, a polycistronic vector carrying all four factors was able to generate iPS cells. In this preliminary experiment we co-infected Oct4-GFP fibroblasts with the polycistronic Sox2-Oct4-Klf4-myc vector and an additional Oct4 vector (to account for the possibility that relatively more Oct4 protein might be needed for reprogramming; FIG. 13B). FIG. 13B shows that iPS cells were obtained that expressed AP, SSEA1, Nanog and Oct4. Moreover adult chimeras have been generated from iPS lines infected with the four-factor 2A vector plus Oct4 Moloney virus. To determine the number of proviral integrations, a Southern blot was sequentially hybridized with a Sox2, Klf4, c-myc and Oct4 probe. FIG. 13C shows that a single polycistronic vector was integrated in 2 of 3 different tested iPS lines and 2 proviruses were carried in the third line (in this line, 4F0#14, the c-myc sequences were deleted in one of the proviruses). Surprisingly, an additional 8 to 11 Oct 4 proviruses were carried in each of the iPS lines, suggesting strong selection for multiple integrations of the Oct4 provirus. Because we have never seen more than 4 or 5 Oct4 proviruses in iPS cells induced by the four separately transduced factors, it is unlikely though cannot be excluded that selection was for high Oct4 expression. An alternative interpretation is that the selection for multiple proviruses was due to selection for insertional activation of an unknown cellular gene. These initial data suggested that at least 3 reprogramming factors can be expressed from a single polycistronic provirus to induce reprogramming. As further described below, we proceeded to successfully generated murine iPS cells using only a polycistronic vector carrying the four factors and have also used the polycistronic vector system for generating human iPS cells carrying minimal genetic alteration.

A tetracycline inducible lentivirus vector was constructed where expression of the genes was controlled from the tetracycline operator minimal promoter (tetOP; FIG. 14C). To test whether all four genes of a single four-factor (Oct4/Sox2/Klf4/c-Myc) virus could be expressed upon DOX addition, MEFs were infected with the polycistronic vector (referred below to as "4F2A") as well as a constitutive FUW lentivirus carrying the tetracycline controllable trans-activator (M2rtTA; abbreviated as rtTA). Two independent experiments were performed and drug inducible expression of the virus was tested 3 days post-infection by qRT-PCR. Using primers for viral specific transcripts (E2A-cMyc), robust induction was observed (7-10 fold) in cells cultured with DOX as compared to control medium (FIG. 14D). To test the relative induction compared to ES cells, Oct4 and Sox2 primers that cannot discriminate between viral or endogenous transcripts were utilized and in both experiments infected DOX induced MEFs were significantly higher than in ES cells (~3.5- and ~17-fold over ES levels respectively). Western blot analysis of cells isolated at 3 days after infection demonstrated that little or no protein was expressed when the cells were cultured without DOX whereas robust induction was seen in the presence of DOX with levels of Oct4 and Sox2 protein being similar to that in ES cells (FIG. 14E).

Figures 15A, 15B, 15C:
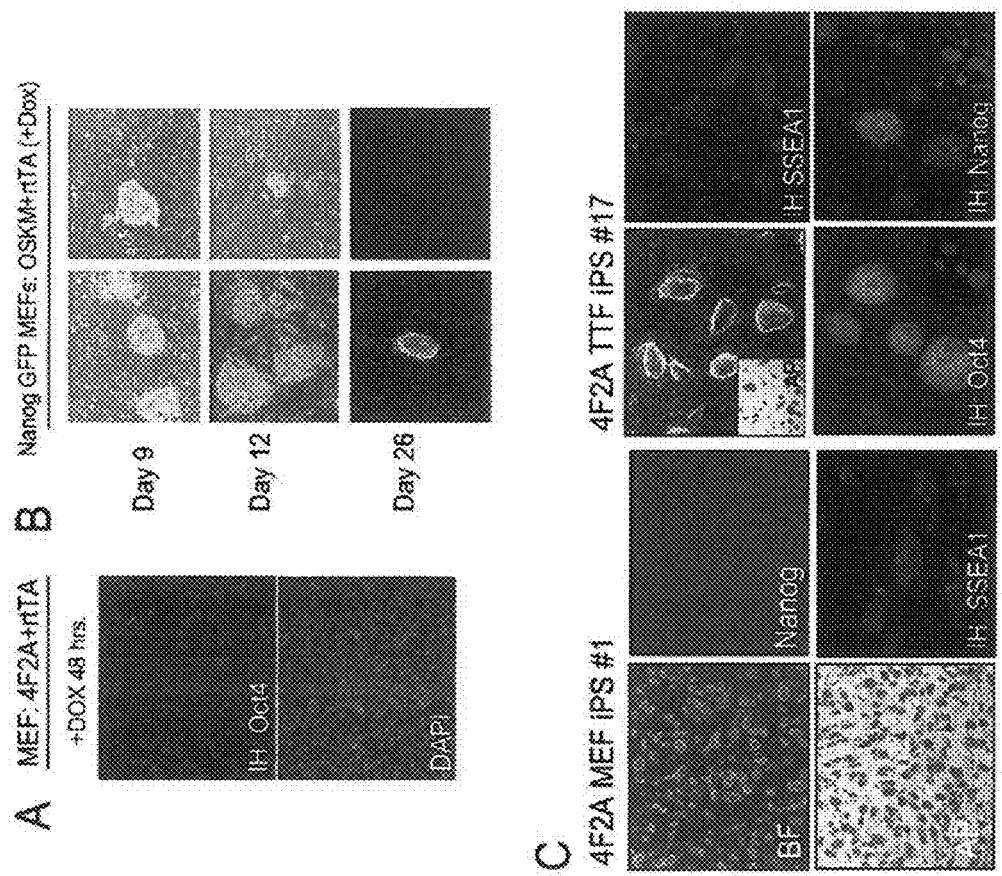
FIGS. 15A-15C illustrate that 4F2A iPS cells express pluripotency markers.

To test whether the 4F2A vector was able to reprogram somatic cells to a pluripotent state MEFs containing a GFP reporter driven by the endogenous Nanog promoter were infected with virus (4F2A+rtTA). 85-90% of the cells stained for Oct4 at 48 hours after transduction indicating high titre infection (FIG. 15A). Morphological changes were observed a few days after addition of DOX (data not shown) with distinct colonies appearing after about 8 days and Nanog-GFP+ cells at approximately 25 days after DOX induction (FIG. 15B). After mechanical isolation and subsequent passage the cells had the typical morphology of ES cells and grew independently of DOX. Four independent 4F2A iPS cell lines were established that were positive for the pluripotency markers AP, SSEA1 and Nanog-GFP (FIG. 15C).

Figures 16A, 16B, 16C:
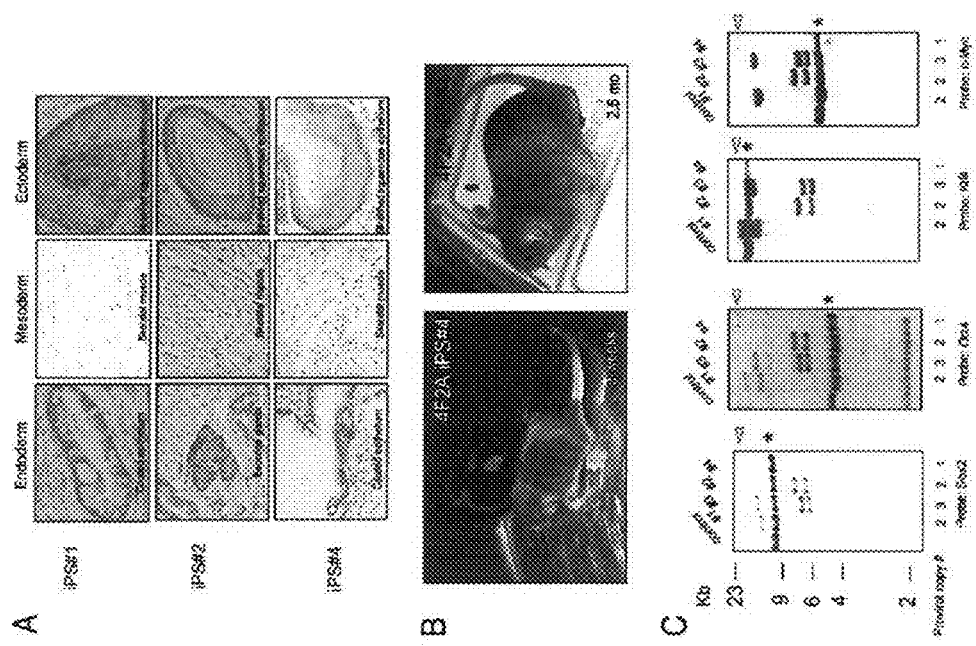
FIGS. 16A-16C illustrates that 4F2A iPS cells are pluripotent and contain between 1-3 proviral integrations.

To investigate whether adult somatic cells could be reprogrammed using the 4F2A vector, we infected tail-tip fibroblasts (TTFs) from 14 week-old mice with the 4F2A+rtTA vectors. Similar to MEFs, typical morphological changes were observed a few days after addition of DOX media. Colonies appeared around 8 days and continued to expand until they were picked (day 16) based on morphology. After several passages four stable iPS cell lines were established that stained positive for all pluripotency markers (Nanog, Oct4, SSEA1, AP) (FIG. 15C). MEF iPS cell lines were injected subcutaneously into SCID mice and were shown to induce teratomas that contained differentiated cells of all three germ layers (FIG. 16A). Finally, injection of MEF iPS cells (#4) into blastocysts generated postnatal chimeras (FIG. 16B) demonstrating that a single 4F2A polycistronic virus can reprogram MEFs to a pluripotent state.

Figure 18A:
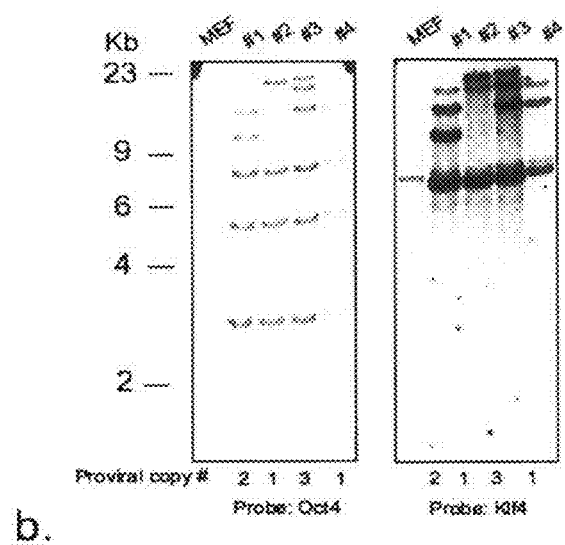
FIGS. 18A-18B show Southern blot of MEF-derived iPS lines and dox-withdrawl, indicating 8 days is sufficient to generate iPS lines.
Figure 18B:
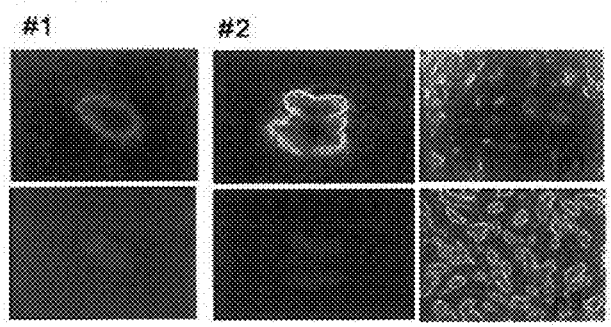

To determine the number of proviruses carried in the 4F2A iPS cell lines, DNA was extracted and subjected to Southern blot analysis using an enzyme that does not cut in the vector sequences. Using Oct4, Sox2, c-Myc and Klf4 probes for hybridization, we detected bands of identical molecular weight confirming that the factor sequences were carried in one provirus. The total number of proviruses was between one and three with iPS cell line #4 carrying a single viral insert (FIG. 16C). One of two integrations from iPS cell line #1 failed to produce a band after c-Myc hybridization, suggesting a 3' deletion of the c-Myc sequences may have occurred. A second digest confirmed the proviral copy numbers (FIG. 18A).

Figure 19:
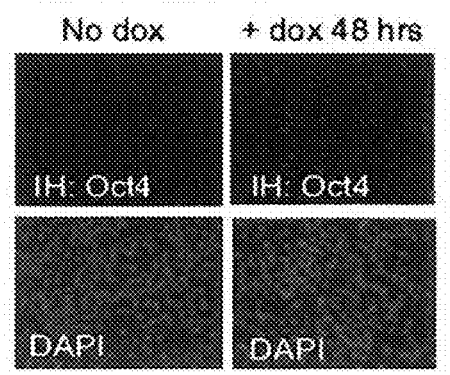
FIG. 19 shows relative efficiencies of reprogramming using 4F2A in MEFs. NanogGFP MEFs were infected with 4F2A+rtTA and cultured in ES media (+/−DOX) for 48 hours. Cells were fixed and stained for Oct4 protein. Estimated infection efficiency was ~70%. The same virus was also used to infect 0.2 5×10^6 Nanog GFP MEFs and cells were cultured on DOX for 20 days. After withdrawl of DOX at day 20, GFP+ colonies were counted at day 25, in three plates 10, 10, and 17 GFP+ colonies were observed.

To estimate reprogramming efficiency MEFs were infected with the 4F2A and rtTA vectors and plated at $0.25 \times 10^6$ per 10 cm plate culture dish. About 70% of the MEFs were infected as estimated by immunostaining of Oct4 at 48 hours after infection (FIG. 19A). Cells were cultured in ES media containing DOX for 20 days and subsequently transferred to ES cell medium until GFP+ colonies were counted on day 25. An average of ~14.7±4 colonies were detected in three independent dishes (10+10+17) indicating a relative efficiency of 0.0001%. This is one to two orders of magnitude lower than that of 'primary' infected fibroblasts (3, 7).

To test the kinetics of reprogramming using the 4F2A virus we performed dox-withdrawal experiments where at specified days (i.e. 2, 4, 8, 12 etc) DOX containing media is replaced with ES media and the number of Nanog-GFP+ colonies are counted at day 25. Using separate drug-inducible viruses to deliver the four factors it has been reported that ~9-12 days is the minimum time required for the generation of stable iPS cells (20, 21). Cells are not passaged during this time in order to minimize duplication of reprogramming events. Two independent experiments were performed and in both cases single Nanog-GFP+ colonies were present on plates cultured in DOX media for 8 days, similar to the minimum time required using separate viruses (FIG. 14B).

These data demonstrate that a single polycistronic virus containing the four factors linked by three 2A peptides allows factor expression sufficient to generate iPS cells from embryonic or adult somatic cells. Importantly, our results also show that a single polycistronic proviral copy is sufficient to reprogram somatic cells to pluripotency.

Generation of Human iPS Cells Using a Single Polycistronic Virus

Figures 20A, 20B:
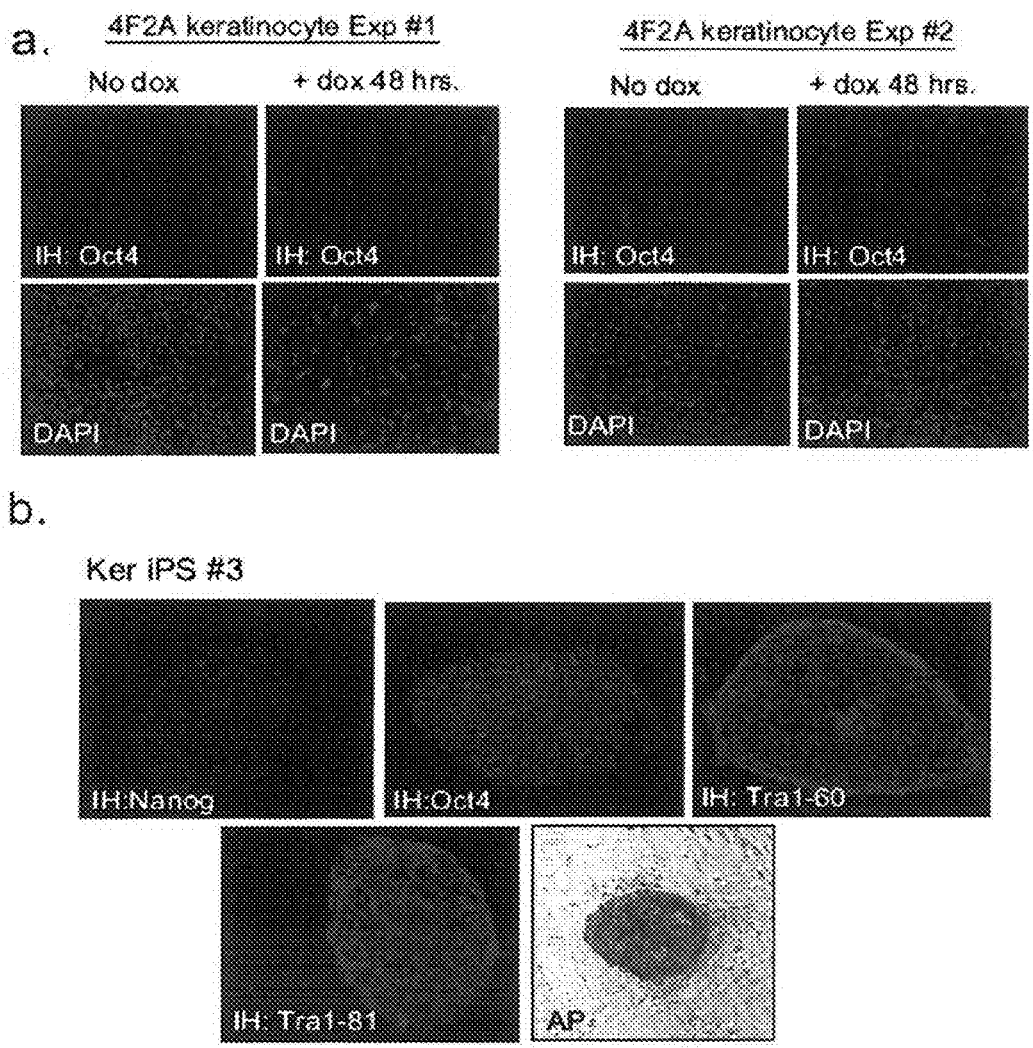
FIGS. 20A-20B illustrate infection efficiency and pluripotency analysis of keratinocyte-derived human iPS lines.
Figure 21A:
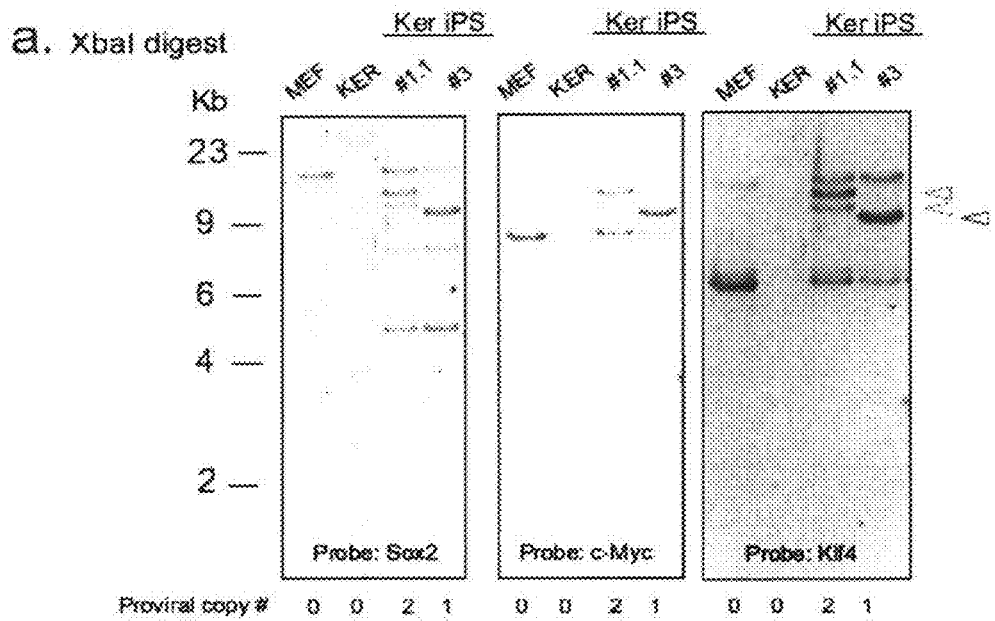
FIGS. 21A-21B show proviral copy number of Keratinocyte-derived human iPS lines.
Figure 21B:
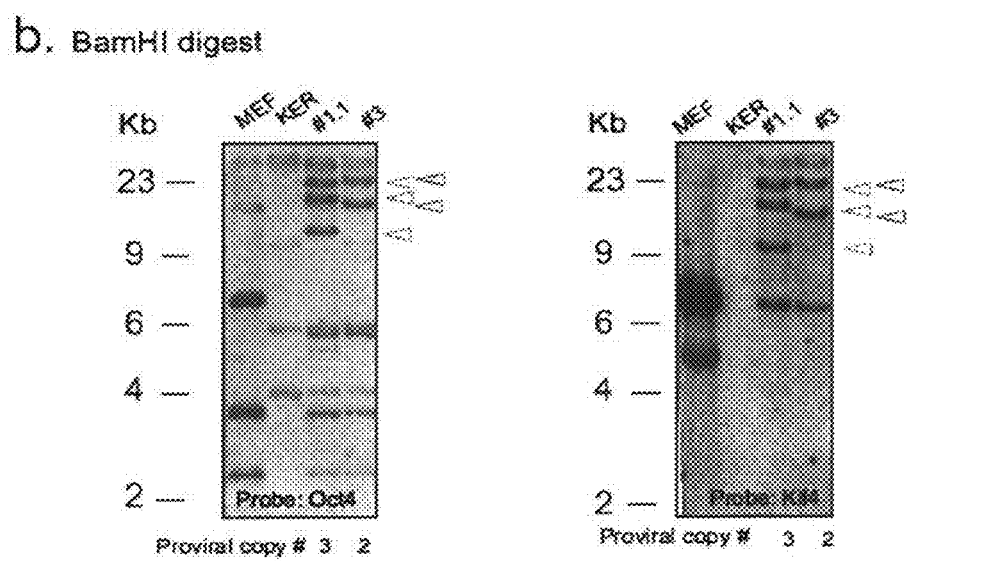

To investigate whether human cells could be reprogrammed with the polycistronic vector, neonatal human foreskin keratinocytes (NHFK) were transduced with both the constitutive rtTA and DOX-inducible 4F2A vectors. The fraction of infected cells was 10% as determined by staining for Oct4 at 48 hours after transduction (FIG. 20A). Cells were incubated in keratinocyte medium+DOX and allowed to grow for 6 days until they were passaged and cultured in hESC media+DOX on gelatinized plates. Colonies were first detected at day 12 and most displayed transformed morphology with a few colonies exhibiting a distinct appearance that resembled hESC-like morphology. Two such colonies generated in independent infections were picked between 22 and 35 days after infection and found to expand as distinct colonies with morphology similar to hESC (FIG. 17A). These cells were expanded in the absence of DOX and gave rise to a homogenous population identical to hESC (Ker-iPS) after an additional 2-5 passages. The cells stained for the pluripotency markers AP, Oct4, Nanog, Sox2, SSEA4, Tra1-60, Tra1-81 (FIG. 17B, FIG. 10B) and had a normal karyotype (FIG. 17C). DNA fingerprinting excluded that such Ker-iPS cell lines were contamination from previously established human iPS cells or hES lines from our lab (data not shown). To determine proviral copy number in Ker-iPS cell lines genomic DNA was extracted and subjected to Southern blot analysis using an enzyme that does not cut in the vector sequences. Probes for all four reprogramming factors show hybridization to similar molecular weight band(s) again indicating they were carried on a single virus. Two different digests (XbaI & BamHI) show the 4F2A proviral copy number is three (#1.1) and two (#3) respectively (FIG. 21A-B).

To test for pluripotency, one line, Ker-iPS #1.1, was injected subcutaneously into SCID mice. These cells induced teratomas and after histological examination differentiated into cells of all three germ layers (FIG. 17D). In addition, Ker-iPS #1.1 cells, when subjected to an in-vitro neural differentiation protocol produced nestin+ neural progenitor cell populations as well as Tuj1+ post-mitotic neurons as detected by immunostaining. (FIG. 17E).

Discussion:

The experiments described above show that up to four different reprogramming factors inserted into a polycistronic vector separated by 2A sequences can be expressed at levels sufficient to achieve reprogramming. Embryonic and adult murine fibroblasts as well as postnatal human keratinocytes were induced to form pluripotent iPS cells when infected with the FUW rtTA and 2A vector transducing Oct4, Sox2, Klf4 and c-Myc.

We observe a reprogramming efficiency significantly lower than previous experiments using single vectors to transduce each of the four factors (FIG. 19B and Table 3).

TABLE 3

Table summarizing pluripotency tests as well as relative efficiencies for all iPS lines generated.

| Source of cells | GFP | iPS lines | Efficiency (iPS/input, %) | ES | TF | PC |
|---|---|---|---|---|---|---|
| (m) embryonic fib | Nanog | 5 | 0.0001% | Yes | Yes | Yes |
| (m) adult fib | No | 4 | ND | Yes | No | No |
| (h) Keratinocytes | No | 2 | 0.00001% | Yes | Yes | No |

| Cell line | Blast injected | Live pups | # chimeric | chimerism (%) |
|---|---|---|---|---|
| MEF iPS #4 | 60 | 30 | 2 | 30-50 |
| MEF iPS #2 | 20 | 14 | 1 | 10 |

GFP, GFP reporter gene present;
ES, expression of ES cell markers (AP, SSEA1, Oct4 or Sox2);
TF, teratoma formation;
PC, postnatal chimeras.
Mouse chimerism was estimated by agouti coat color.

It is possible that the lower reprogramming efficiency is due to the stochiometry of factor expression from the polycistronic vector, which may be suboptimal for inducing reprogramming. Transduction with separate vectors allows integration of different numbers of proviruses for each factor, therefore reprogramming may select for a specific set of proviral integrations that result in high expression or an optimal stochiometry between the different factors. However, the 2A system, has been reported to support near equimolar protein expression in vivo (17). Also, when separate vectors transducing each of the four factors were used for induction of iPS cells, Nanog-GFP positive cells were detected as early as 16 days after DOX induction in contrast to GFP positive cells observed 22-25 days after 4F2A vector transduction, consistent with less optimal reprogramming. Moreover, whereas iPS cells frequently carry multiple Oct4 or Klf4 proviruses, consistently fewer Sox2 proviruses were found suggesting that a high level of Sox2 expression may perhaps be unfavorable for reprogramming (24).

Figure 22:
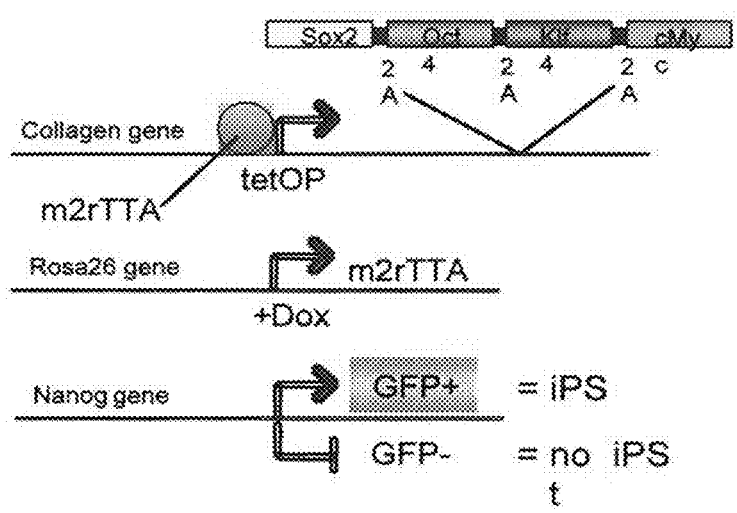
FIG. 22 illustrates a strategy for generating iPS cells with single polycistronic construct at defined genomic locations.

In other experiments, the flp-in transgenic system is used to create multiple murine cell lines containing 4-, 3- and 2-factor 2A constructs in the collagen gene locus (FIG. 22) (20). The system contains two components: tetracycline controllable trans-activator (rtTA) and tetracycline operator minimal promoter (tetOP) driving the gene of interest. After addition of media containing doxycycline the trans-activator drives expression of the transgene at the collagen locus. If desired, inserting a GFP reporter construct at the Nanog gene allows detection of complete reactivation of the Nanog locus and act as a marker of genome-wide epigenetic reprogramming.

References for Example 3

1. Lowry W E, Richter L, Yachechko R. et al. (2008) Generation of human induced pluripotent stem cells from dermal fibroblasts *Proc Natl Acad Sci USA* 105, 2883-2888.
2. Maherali N, Sridharan R, Xie W, et al. (2007) Directly reprogrammed fibroblasts show global epigenetic remodeling and widespread tissue contribution *Cell Stem Cell* 1, 55-70.
3. Okita K, Ichisaka T, & Yamanaka S (2007) Generation of germline-competent induced pluripotent stem cells *Nature* 448, 313-317.
4. Park I H, Zhao R, West J A, et al. (2008) Reprogramming of human somatic cells to pluripotency with defined factors *Nature* 451, 141-146.
5. Takahashi K, Tanabe K, Ohnuki M, et al. (2007) Induction of pluripotent stem cells from adult human fibroblasts by defined factors *Cell* 131, 861-872.
6. Takahashi K & Yamanaka S (2006) Induction of pluripotent stem cells from mouse embryonic and adult fibroblast cultures by defined factors *Cell* 126, 663-676.
7. Wernig M, Meissner A, Foreman R, et al. (2007) In vitro reprogramming of fibroblasts into a pluripotent ES-cell-like state *Nature* 448, 318-324.
8. Yu J, Vodyanik M A, Smuga-Otto K, et al. (2007) Induced pluripotent stem cell lines derived from human somatic cells *Science* 318, 1917-1920.
9. Hanna J, Markoulaki S, Schorderet P, et al. (2008) Direct reprogramming of terminally differentiated mature B lymphocytes to pluripotency *Cell* 133, 250-264.
10. Kim J B, Zaehres H, Wu G, et al. (2008) Pluripotent stem cells induced from adult neural stem cells by reprogramming with two factors *Nature* 454, 646-650.
11. Stadtfeld M, Brennand K, & Hochedlinger K (2008) Reprogramming of pancreatic beta cells into induced pluripotent stem cells *Curr Biol* 18, 890-894.
12. Hanna J, Wernig M, Markoulaki S, et al. (2007) Treatment of sickle cell anemia mouse model with iPS cells generated from autologous skin *Science* 318, 1920-1923.
13. Wernig M, Zhao J P, Pruszak J, et al. (2008) Neurons derived from reprogrammed fibroblasts functionally integrate into the fetal brain and improve symptoms of rats with Parkinson's disease *Proc Natl Acad Sci USA* 105, 5856-5861.
14. Ryan M D & Drew J (1994) Foot-and-mouth disease virus 2A oligopeptide mediated cleavage of an artificial polyprotein *Embo J* 13, 928-933.
15. Ryan M D, King A M, & Thomas G P (1991) Cleavage of foot-and-mouth disease virus polyprotein is mediated by residues located within a 19 amino acid sequence *J Gen Vivol* 72 (Pt 11), 2727-2732.
16. Doronina V A, Wu C, de Felipe P, et al. (2008) Site-specific release of nascent chains from ribosomes at a sense codon *Mol Cell Biol* 28, 4227-4239.
17. Szymczak A L, Workman C J, Wang Y, et al. (2004) Correction of multi-gene deficiency in vivo using a single 'self-cleaving' 2A peptide-based retroviral vector *Nat Biotechnol* 22, 589-594.
18. Lois C, Hong E J, Pease S, et al. (2002) Germline transmission and tissue-specific expression of transgenes delivered by lentiviral vectors *Science* 295, 868-872.
19. Wernig M, Lengner C J, Hanna J, et al. (2008) A drug-inducible transgenic system for direct reprogramming of multiple somatic cell types *Nat Biotechnol* 26, 916-924.

20. Brambrink T, Foreman R, Welstead G G, et al. (2008) Sequential expression of pluripotency markers during direct reprogramming of mouse somatic cells *Cell Stem Cell* 2, 151-159.
21. Stadtfeld M, Maherali N, Breault D T, et al. (2008) Defining molecular cornerstones during fibroblast to iPS cell reprogramming in mouse *Cell Stem Cell* 2, 230-240.
22. Okita K, Nakagawa M, Hyenjong H, et al. (2008) Generation of Mouse Induced Pluripotent Stem Cells Without Viral Vectors *Science* 322, 949-953
23. Stadtfeld M, Nagaya M, Utikal J, et al. (2008) Induced Pluripotent Stem Cells Generated Without Viral Integration *Science* 322, 945-949.
24. Eminli S, Utikal J S, Arnold K, et al. (2008) Reprogramming of Neural Progenitor Cells into iPS Cells in the Absence of Exogenous Sox2 Expression *Stem Cells*.
25. Meissner A, Wernig M, & Jaenisch R (2007) Direct reprogramming of genetically unmodified fibroblasts into pluripotent stem cells *Nat Biotechnol* 25, 1177-1181.
26. Zhang S C, Wernig M, Duncan I D, et al. (2001) In vitro differentiation of transplantable neural precursors from human embryonic stem cells *Nat Biotechnol* 19, 1129-1133.
27. Hockemeyer D, Soldner F, Cook E G, et al. (2008) A drug-inducible system for direct reprogramming of human somatic cells to pluripotency *Cell Stem Cell* 3, 346-353.

Example 4

Human Induced Pluripotent Stem Cells Free of Viral Reprogramming Factors

Experimental Procedures
Cell Culture

All primary fibroblast cell lines described in this paper were purchased from the Coriell Cell Repository. Fibroblasts were cultured in fibroblast medium [DMEM supplemented with 15% FBS (Hyclone), 1 mM glutamine (Invitrogen), 1% nonessential amino acids (Invitrogen) and penicillin/streptomycin (Invitrogen)]. HiPSCs and the hESC lines BG01 and BG02 (NIH Code: BG01 and BG02; BresaGen, Inc., Athens, Ga.) were maintained on mitomycin C (MMC)-inactivated mouse embryonic fibroblast (MEF) feeder layers in hESC medium [DMEM/F12 (Invitrogen) supplemented with 15% FBS (Hyclone), 5% KnockOut™ Serum Replacement (Invitrogen), 1 mM glutamine (Invitrogen), 1% nonessential amino acids (Invitrogen), 0.1 mM β-mercaptoethanol (Sigma) and 4 ng/ml FGF2 (R&D systems)]. Cultures were passaged every 5 to 7 days either manually or enzymatically with collagenase type IV (Invitrogen; 1.5 mg/ml). Human embryonic stem cells H9 (NIH Code: WA09, Wisconsin Alumni Research Foundation, Madison, Wis.) were maintained on MMC-inactivated MEFs or on MMC-inactivated human fibroblasts (D551; American Type Culture Collection, Manassas, Va.) according to the manufacturer's protocol. For EB induced differentiation, ESC/hiPSC colonies were harvested using 1.5 mg/ml collagenase type IV (Invitrogen), separated from the MEF feeder cells by gravity, gently triturated and cultured for 10 days in non-adherent suspension culture dishes (Corning) in DMEM supplemented with 15% FBS.

For Cre-recombinase mediated vector excision, hiPSC lines were cultured in Rho Kinase (ROCK)-inhibitor (Calbiochem; Y-27632) 24 hours prior to electroporation. Cell were harvested using 0.05% trypsin/EDTA solution (Invitrogen) and $1 \times 10^7$ cells resuspended in PBS were transfected with either pCre-PAC (50 µg; Taniguchi et al., 1998) or co-transfected with pTurbo-Cre (40 µg; Genbank Accession Number AF334827) and pEGFP-N1 (10 µg; Clontech) by electroporation as described previously (Costa et al., 2007; Gene Pulser Xcell System, Bio-Rad: 250 V, 500 µF, 0.4 cm cuvettes). Cells were subsequently plated on MEF feeder layers (DR4 MEFs for puromycin selection) in hESC medium supplemented with ROCK-inhibitor for the first 24 hours. Cre-recombinase expressing cells were selected using one of the following methods: 1) addition of puromycin (2 µg/ml) 2 days after electroporation for a period of 48 hours. 2) FACS sorting (FACS-Aria; BD-Biosciences) of a single cell suspension for EGFP expressing cells 60 hours after electroporation followed by replating at a low density in ROCK-inhibitor containing hESC medium. Individual colonies were picked 10 to 14 days after electroporation.

Viral Constructs

The FUW-M2rtTA lentiviral vector and lentiviral vectors containing the human c-DNAs for KLF4 (FUW-tetO-hKLF4), OCT4 (FUW-tetO-hOCT4), SOX2 (FUW-tetO-hSOX2), and c-MYC (FUW-tetO-hMYC) under the control of the tetracycline operator and a minimal CMV promoter have been described previously (Hockemeyer et al., 2008). To generate the Cre-recombinase excisable DOX-inducible lentiviral vectors, a Not I/Bsu36 I fragment containing the tetracycline operator/minimal CMV promoter and the human c-DNAs for either KLF4, OCT4 or SOX2 were subcloned from each FUW-tetO vector into the Not I/BSU36 I sites of the FUGW-loxP, which contains a loxP site in the 3'LTR (Hanna et al., 2007).

Lentiviral Infection And hiPSC Derivation

VSVG coated lentiviruses were generated in 293 cells as described previously (Brambrink et al., 2008). Briefly, culture medium was changed 12 hours post-transfection and virus-containing supernatant was collected 60-72 hours post transfection. Viral supernatant was filtered through a 0.45 µm filter. Virus-containing supernatants were pooled for 3 and 4 factor infections and supplemented with FUW-M2rtTA virus and an equal volume of fresh culture medium. $1 \times 10^6$ human fibroblasts were seeded 24 hours before transduction in T75 flasks. Four consecutive infections in the presence of 2 µg/ml of polybrene were performed over a period of 48 hours. Culture medium was changed 12 hours after the last infection. Five days after transduction, fibroblasts were passaged using trypsin and re-plated at different densities between $5 \times 10^4$ and $2 \times 10^5$ cells per 10 cm$^2$ on gelatin coated dishes. To induce reprogramming, culture medium was replaced 48 hours later by hESC medium supplemented with DOX (Sigma-Aldrich; 2 µg/ml). HiPSCs colonies were picked manually based on morphology between 3 and 5 weeks after DOX-induction and manually maintained and passaged according hESC protocols in the absence of DOX. To determine reprogramming efficiencies, $1 \times 10^5$ human fibroblasts were seeded onto 10 cm$^2$ gelatin coated dishes. Reprogramming efficiencies were calculated after 20 days based on immunocytochemistry for the pluripotency markers Tra-1-60 and NANOG.

Microarray Gene Expression Analysis

RNA was isolated from hESCs and iPSCs, which were mechanically separated from feeder cells, using the RNeasy Mini Kit (Qiagen). 2 µg total RNA was used to prepare biotinylated cRNA according to the manufacturer's protocol (Affymetrix One Cycle cDNA Synthesis Kit). Briefly, this method involves SuperScript II-directed reverse transcription using a T7-Oligo (dT) Promoter Primer to create first strand cDNA. RNase H-mediated second strand cDNA synthesis is followed by T7 RNA Polymerase directed in vitro transcription, which incorporates a biotinylated nucleotide analog during cRNA amplification. Samples were prepared for hybridization using 15 µg biotinylated cRNA in a 1× hybridization cocktail according the Affymetrix hybridization manual. GeneChip arrays (Human U133 2.0) were hybridized in a GeneChip Hybridization Oven at 45° C. for 16 hours at 60 RPM. Washing was done using a GeneChip Fluidics Station 450 according to the manufacturer's instructions, using the buffers provided in the Affymetrix GeneChip Hybridization, Wash and Stain Kit. Arrays were scanned on a GeneChip Scanner 3000 and images were extracted and analyzed using GeneChip Operating Software v1.4.

U133 Plus 2.0 microarrays (Affymetrix) were processed using the MASS algorithm and absent/present calls for each probeset were determined using the standard Affymetrix algorithm, both as implemented in Bioconductor. Probesets that were absent in all samples were removed for subsequent analysis. Differential expression was determined a moderated t-test using the 'limma' package in R (corrected for false discovery rate) or by fold change. Where a gene was represented by multiple probesets (based on annotation from Affymetrix), gene expression log-ratios and p-values were calculated as the mean and minimum of these probesets, respectively. Hierarchical clustering was performed on log-transformed gene expression ratios using uncentered Pearson correlation and pairwise average linkage. Correlations were compared using Fisher's Z transformation. Confidence of the hierarchical clustering was computed using multiscale bootstrap resampling with the R package 'pvclust'.

Reverse Transcription of Total RNA and Real-Time PCR

RNA was isolated from EBs or hESCs and iPSCs, which were mechanically separated from feeder cells, using either the RNeasy Mini Kit (Qiagen) or Trizol extraction and subsequent ethanol precipitation. Reverse transcription was performed on 1 µg of total RNA using oligo dT priming and Thermoscript reverse transcriptase at 50° C. (Invitrogen). Real-time PCR was performed in an ABI Prism 7000 (Applied Biosystems) with Platinum SYBR green pPCR SuperMIX-UDG with ROX (Invitrogen) using primers that were in part previously described (Hockemeyer et al., 2008; Yu et al., 2007) and in part are described in Soldner, et al., 2009, Supplemental Experimental Procedures.

Teratoma Formation and Analysis

HiPSCs were collected by collagenase treatment (1.5 mg/ml) and separated from feeder cells by subsequent washes with medium and sedimentation by gravity. HiPSC aggregates were collected by centrifugation and resuspended in 250 µl of phosphate buffered saline (PBS). HiPSCs were injected subcutaneously in the back of SCID mice (Taconic). Tumors generally developed within 4-8 weeks and animals were sacrificed before tumor size exceeded 1.5 cm in diameter. Teratomas were isolated after sacrificing the mice and fixed in formalin. After sectioning, teratomas were diagnosed based on hematoxylin and eosin staining.

Methylation Analysis

Genomic DNA was collected from hESCs and hiPSCs by mechanical separation from feeder cells. DNA was proteinase K treated and phenol chloroform extracted and 1 µg of DNA was subjected to conversion using the Qiagen EpiTect Bisulfite Kit. Promoter regions of OCT4 were amplified using previously described primers (Yu et al., 2007):

(SEQ ID NO: 32)
OCT4 Forward: ATTTGTTTTTTGGGTAGTTAAAGGT (SEQ ID NO: 33)
OCT4 Reverse: CCAACTATCTTCATCTTAATAACATCC PCR products were cloned using the pCR2.1-TOPO vector and sequenced using M13 forward and reverse primers.

Immunocytochemistry

Cells were fixed in 4% paraformaldehyde in PBS and immunostained according to standard protocols using the following primary antibodies: SSEA4 (mouse monoclonal, Developmental Studies Hybridoma Bank); Tra 1-60, (mouse monoclonal, Chemicon International); hSOX2 (goat polyclonal, R&D Systems); Oct-3/4 (mouse monoclonal, Santa Cruz Biotechnology); hNANOG (goat polyclonal R&D Systems); appropriate Molecular Probes Alexa Fluor® dye conjugated secondary antibodies (Invitrogen) were used.

Southern Blotting

XbaI, EcoRI or MfeI digested genomic DNA was separated on a 0.7% agarose gel, transferred to a nylon membrane (Amersham) and hybridized with $^{32}$P random primer (Stratagene) labeled probes for OCT4 (EcoRI-PstI fragment of pFUW-tetO-hOCT4 plasmid), KLF4 (full length hKLF4 cDNA), c-MYC (full length c-MYC cDNA), SOX2 (FspI-EcoRI fragment of pFUW-tetO-hSOX2 plasmid) and M2rtTA (380 bp C-terminal fragment of the M2rtTA c-DNA).

Accession Numbers

Microarray data are available at the NCBI Gene Expression Omnibus database under the series accession number GSE14711.

Overview

In this example we show that fibroblasts from five patients with idiopathic Parkinson's disease (PD) can be efficiently reprogrammed. Moreover, we derived human induced pluripotent stem cells (hiPSCs) free of reprogramming factors using Cre-recombinase excisable viruses. Factor-free iPSCs maintain a pluripotent state and show a global gene expression profile, more closely related to hESCs than to hiPSCs carrying the transgenes. Our results indicate that residual transgene expression in virus-carrying hiPSCs can affect their molecular characteristics and suggest that factor-free hiPSCs therefore represent a more suitable source of cells for modeling of human disease.

Results

Figures 27A, 27B, 27C:
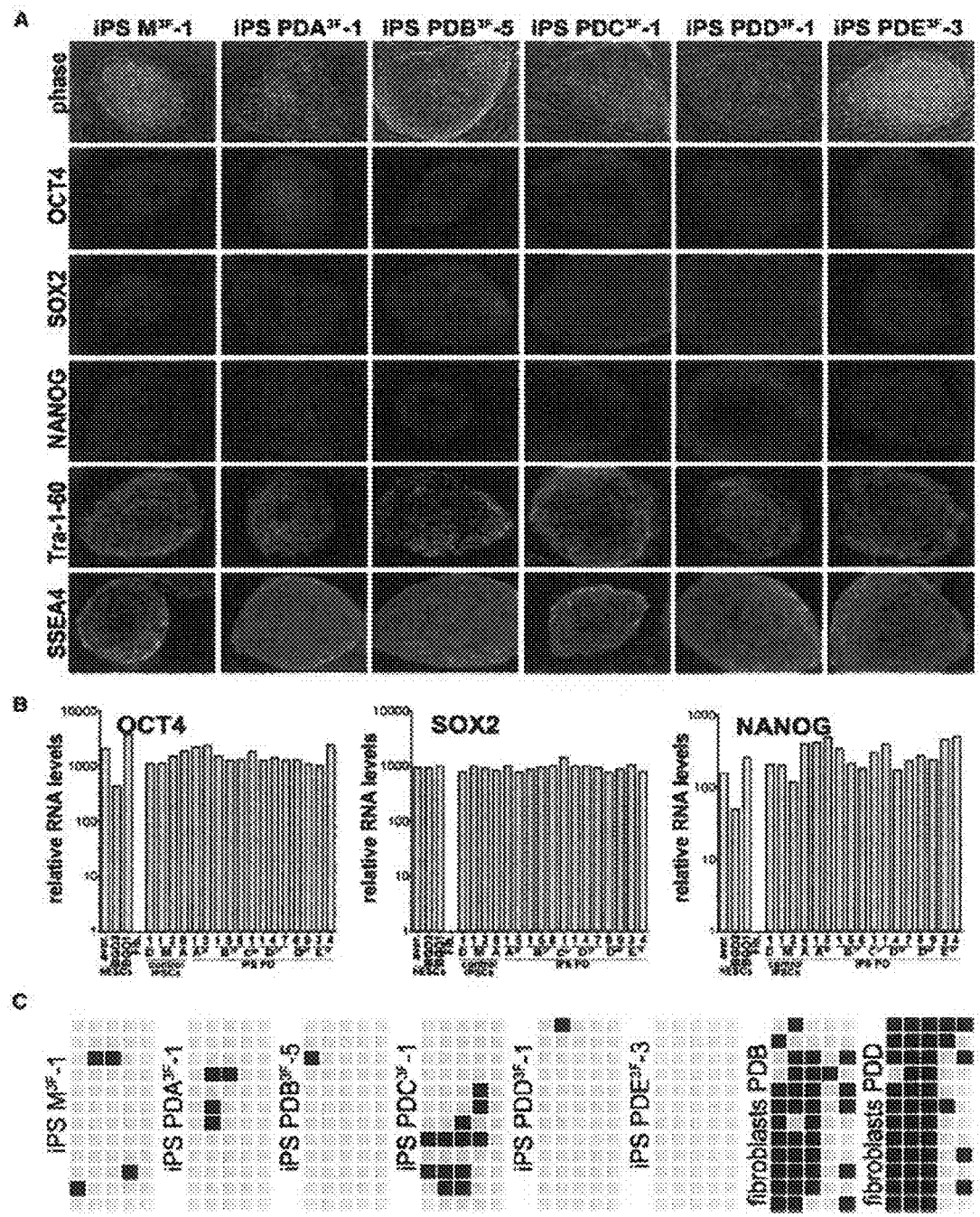
FIGS. 27A-27C show characterization of DOX-inducible hiPSCs derived from fibroblasts from PD patients.
Figures 28A, 28B:
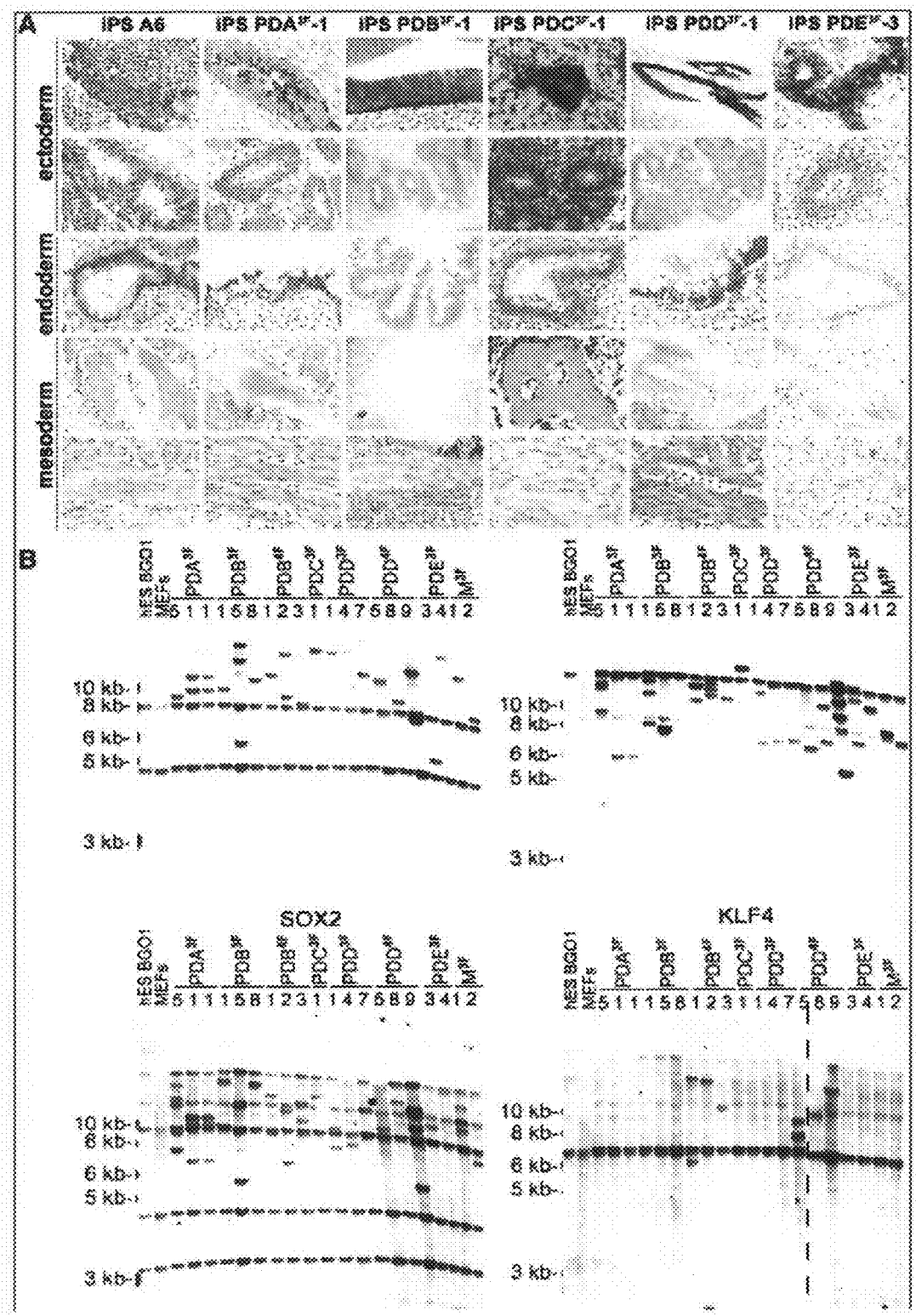

Reprogramming of Fibroblasts from PD Patients by DOX-Inducible Lentiviral Vectors Dermal fibroblasts from five patients with idiopathic PD (age of biopsy between 53 and 85 years) and from two unaffected subjects were obtained from the Coriell Institute for Medical Research (see Table 4). To induce reprogramming, 1×10$^6$ fibroblasts were infected with a constitutively active lentivirus expressing the reverse tetracycline transactivator (FUW-M2rtTA) together with DOX-inducible lentiviruses transducing either 4 (OCT4, SOX2, c-MYC, KLF4) or 3 (OCT4, SOX2, KLF4) reprogramming factors. We will subsequently refer to hiPSC lines derived by transduction of 4 factors as hiPSC$^{4F}$ and those obtained by 3 factors as hiPSC$^{3F}$. Colonies with well-defined hESC like morphology were selected and manually picked 3 to 5 weeks after DOX-induced transgene expression. All fibroblasts obtained from PD patients and non-PD patients gave rise to stable hiPSCs that were maintained in the absence of DOX for more than 30 passages. At least one cell line from each donor fibroblast line was analyzed in detail (Table 4). All of these hiPSCs uniformly expressed the pluripotency markers Tra- 1-60, SSEA4, OCT4, SOX2 and NANOG as determined by immunocytochemistry (FIG. 27A). In addition, all hiPSC lines analyzed by quantitative RT-PCR showed reactivation of the endogenous pluripotency related genes OCT4, SOX2 and NANOG with similar levels of expression as seen in hESCs (FIG. 27B). As expected for hiPSCs, the OCT4 promoter region of PD patient-derived hiPSCs was found to be hypomethylated in contrast to its hypermethylated state in the parental fibroblasts (FIG. 27C). In order to test for pluripotency, hiPSCs isolated from each donor fibroblast line were injected into SCID mice. All hiPSCs formed teratomas comprised of tissues developing from all embryonic germ layers including cartilage, bone, smooth muscle (mesoderm), neural rosettes, pigmented neural epithelium (ectoderm) and intestinal epithelium with goblet- and Paneth-like cells (endoderm) (FIG. 28A).

Figure 28C:
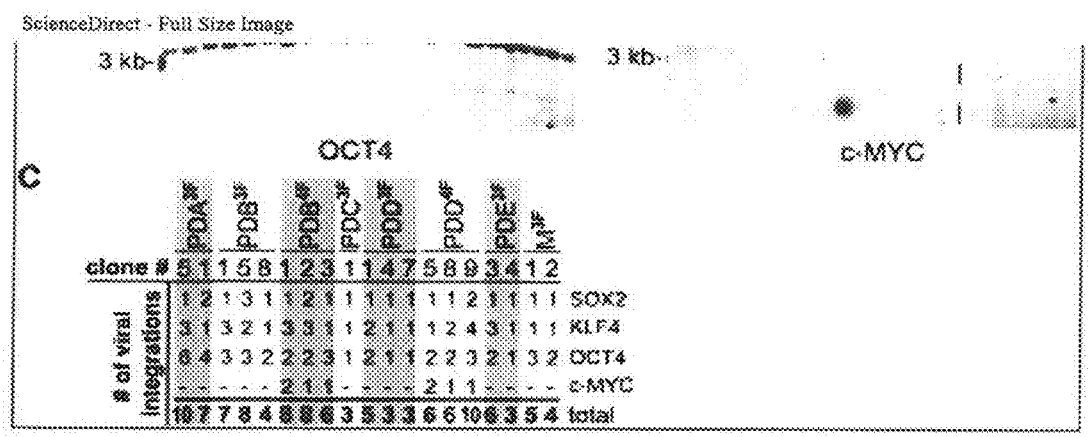
FIG. 28C shows methylation analysis of the OCT4 promoter region. Light gray squares indicate unmethylated and black squares indicate methylated CpGs in the OCT4 promoter of hiPSCs and parental primary fibroblasts cells.

Cytogenetic analysis of PD specific hiPSC lines revealed a normal karyotype in 11 out of 12 lines (see Supplemental FIG. 1 of Soldner, 2009). Only one out of three clones derived from the fibroblast line PDD that had been transduced with 4 factors (iPS PDD$^{4F}$-5), showed an unbalanced translocation between the long-arm of chromosome 18 and the long arm of chromosome 22 resulting in a derivative chromosome 18 and a single copy of chromosome 22. Two independent hiPSCs derived from a non-PD patient fibroblast line (iPS M$^{3F}$-1 and iPS M$^{3F}$-2) showed a balanced translocation between the short and long arms of chromosomes 4 and 7, suggesting that the 4; 7 translocation was already present in the donor fibroblasts (see Soldner, et al., 2009, Supplemental FIG. 1). DNA fingerprinting of the PD patient-derived hiPSCs and the parental fibroblasts were performed to confirm the origin of the hiPSCs and to rule out cross contaminations with existing pluripotent cell lines (data not shown). Southern blot analysis probing for lentiviral integrations showed distinct patterns for each of the hiPSC lines confirming that each line analyzed was derived from independently infected fibroblasts carrying a total of 4 to 10 proviral copies (FIGS. 28B, 28C).

Figures 32A, 32B, 32C, 32D:
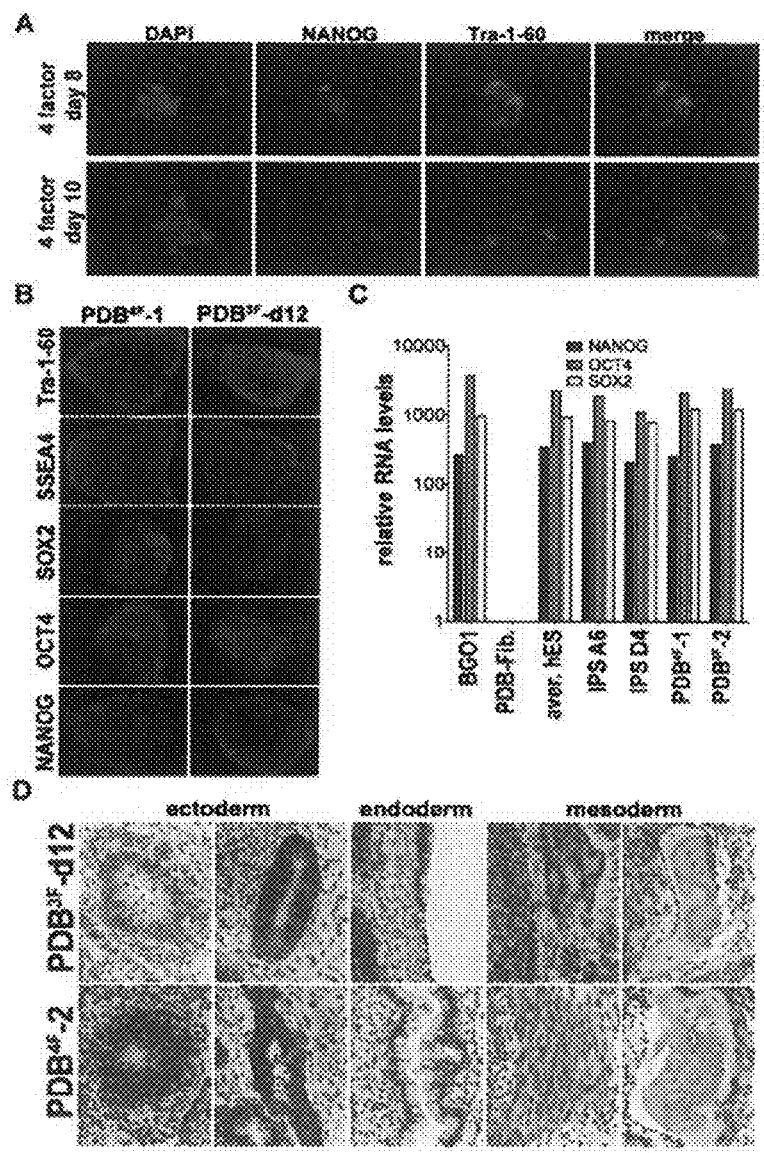
FIGS. 32A-32D show that transgene expression for 8 days is sufficient to reprogram human fibroblasts after primary infections.

In order to further characterize the usefulness of this system, we determined the reprogramming efficiencies for one fibroblast line (PDB) in detail. Reprogramming efficiencies were calculated after 20 days based on immunocytochemistry for the pluripotency markers Tra-1-60 and NANOG. HiPSCs arose with an efficiency of approximately 0.005% after transduction with 3 factors and approximately 0.01% after transduction with 4 factors. This is comparable to previously reported efficiencies using either Moloney-based retroviral vectors or constitutively active lentiviral vectors (Nakagawa et al., 2008; Takahashi et al., 2007; Yu et al., 2007). Immunocytochemistry for NANOG and Tra-1-60 at different time points after DOX addition revealed that small pluripotent colonies could be detected in 4 factor transduced fibroblasts as early as 8 days after transgene induction (FIG. 32A). We also determined the temporal requirement for the expression of the reprogramming factors by varying the time of DOX-induced transgene expression in fibroblasts transduced with either 3 or 4 reprogramming factors. After 24 days we were able to isolate hiPSC colonies from 4 factor transduced fibroblasts exposed to DOX for only 8 days (PDB$^{4F}$-1, 2, 3) whereas hiPSCs from 3 factor transduced cells could be isolated only after exposure to DOX for at least 12 days (PDB$^{3F}$-d12). Although the reprogramming factors were only expressed for a limited period, all of the picked cells gave rise to fully reprogrammed hiPSCs which stained for pluripotency markers (FIG. 32B), reactivated the endogenous OCT4, NANOG and SOX2 genes (FIG. 32C), and formed teratomas comprised of cells derived from the three developmental germ layers (FIG. 32D). Our results suggest that reprogramming by 3 factors is less efficient and takes longer than reprogramming by 4 factors in agreement with previous observations (Nakagawa et al., 2008; Wernig et al., 2008). However, we find that derivation of hiPSCs using 3 factors is more practical, since the infected fibroblast cultures are not overgrown by granulated, fast growing non-hiPSC colonies as has been described previously for cultures infected with 4 factors (Nakagawa et al., 2008; Takahashi et al., 2007).

The results described so far show that DOX-inducible delivery of the reprogramming factors can efficiently generate hiPSCs from skin biopsies obtained from PD patients in the absence of c-MYC with similar kinetics and efficiencies as previously reported using other approaches. Importantly, 8 of 13 3 factor hiPSCs carried a total of only 3 to 5 proviral integrations (FIGS. 28B, 28C), which is significantly less than observed in previous studies (Wernig et al., 2007).

Generation of PD Patient-Derived hiPSCs Free of Viral Reprogramming Factors

Figure 33:
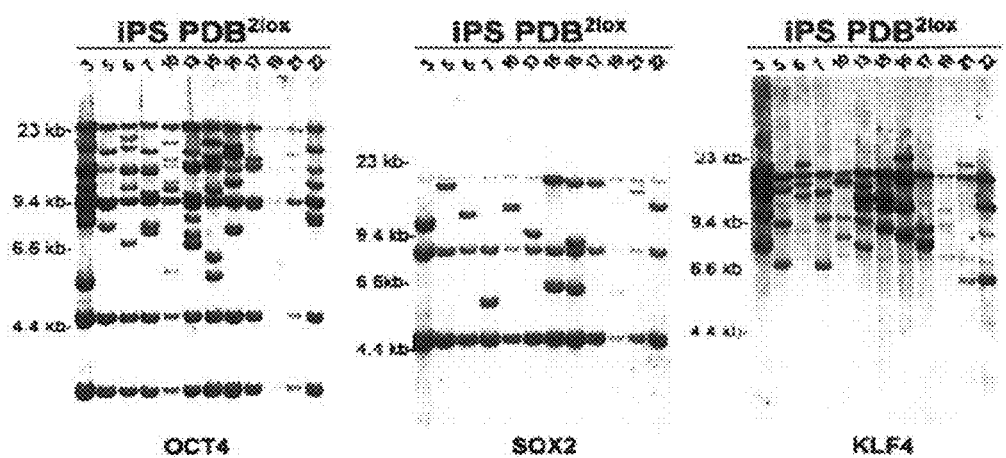
FIG. 33 shows generation of hiPSCs carrying Cre-recombinase excisable viral reprogramming factors. Southern blot analysis of the indicated iPS PDB$^{2lox}$ clones for proviral integrations of XbaI digested genomic DNA using $^{32}$P-labeled DNA probes against OCT4, KLF4, and SOX2. All PDB$^{2lox}$ clones were derived by retroviral transduction with Cre-recombinase excisable lentiviral vectors (FUW-tetO-loxP) for the 3 reprogramming factors OCT4, SOX2 and KLF4.

In order to derive hiPSCs that were free of proviruses, we generated lentiviral vectors that could be excised after integration using Cre-recombinase. The human ubiquitin promoter of the FUGW-loxP lentivirus, which contains a loxP site in the 3'LTR (Hanna et al., 2007), was replaced with a DOX-inducible, minimal CMV promoter followed by the human c-DNAs for OCT4, KLF4 or SOX2. Upon proviral replication, the loxP site in the 3'LTR is duplicated into the 5'LTR resulting in an integrated transgene flanked by loxP sites in both LTRs (FIG. 4A). 1×10$^6$ fibroblasts (PDB) were transduced simultaneously with these 3 viruses as well as a constitutively active lentivirus expressing the reverse tetracycline transactivator (FUW-M2rtTA). 24 hiPSC lines (PDB$^{2lox}$-1 to 24) were isolated 3 to 4 weeks after DOX addition with similar kinetics and efficiency as described above. Southern blot analysis for 12 cell lines showed that 4 PDB$^{21''}$ lines (PDB$^{2lox}$-5, PDB$^{2lox}$-17, PDB$^{2lox}$-21, PDB$^{2lox}$-22) contained only 5 to 7 integrations of the reprogramming factors (FIG. 33). These PDB$^{2lox}$ cell lines were maintained in the absence of DOX for more than 20 passages and displayed all of the characteristics of hiPSCs such as expression of pluripotency related marker proteins Tra-1-60, SSEA4, OCT4, SOX2 and NANOG (FIG. 29B) and the reactivation of the endogenous pluripotency related genes OCT4, NANOG and SOX2 (included in FIG. 31B). Furthermore all tested PDB$^{2lox}$ clones (PDB$^{2lox}$-5, PDB$^{2lox}$-17, PDB$^{2lox}$-21, PDB$^{2lox}$-22) demonstrated in vitro multi-lineage differentiation in EBs (data not shown) and formed teratomas with contributions to all three embryonic germ layers after subcutaneous injection into SCID mice (FIG. 29C).

Figure 34:
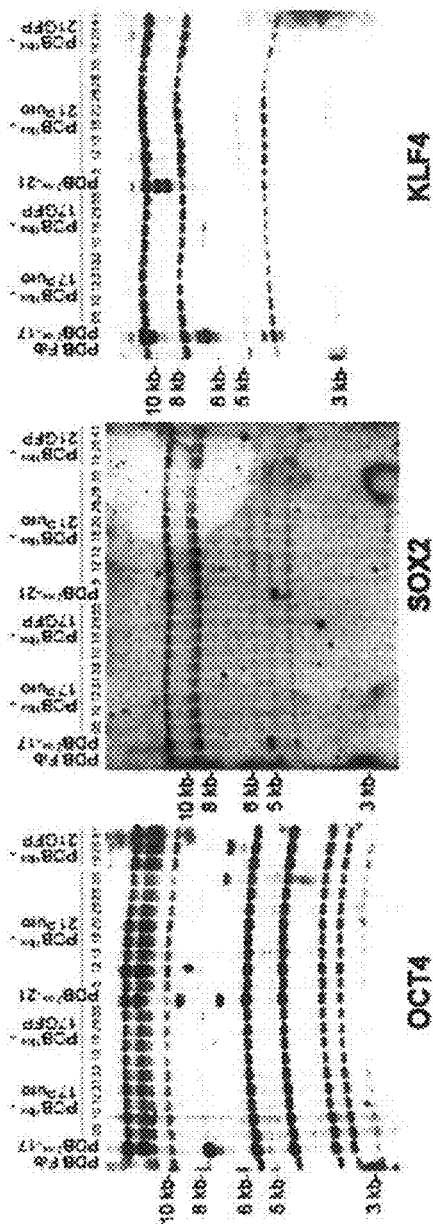
FIG. 34 shows Southern blot analysis for excision of the reprogramming factors in hiPSCs. Southern blot analysis for proviral integrations of parental fibroblasts (PDB), provirus-carrying PDB2lox clones (PDB$^{2lox}$-17 and PDB$^{2lox}$-21) and the indicated PDB$^{1lox}$ clones after Cre-recombinase mediated excision of the transgenes. Puro indicates clones, which were isolated by puromycin selection; GFP indicates clones isolated by FACS sorting for EGFP (as shown in FIG. 5A). Genomic DNA was digested with MfeI and probed for proviral integrations using $^{32}$P-labeled DNA probes against OCT4, KLF4, and SOX2. Based on this Southern blot analysis, the PDB$^{1lox}$ clones indicated in blue (PDB$^{1lox}$-17GFP-10, PDB$^{1lox}$-17GFP-18, PDB$^{1lox}$-21Puro35 and PDB$^{1lox}$-21GFP-28) were regarded as either partially deleted or mixed cellular populations with partial deletions of the transgenes.
Figure 35:
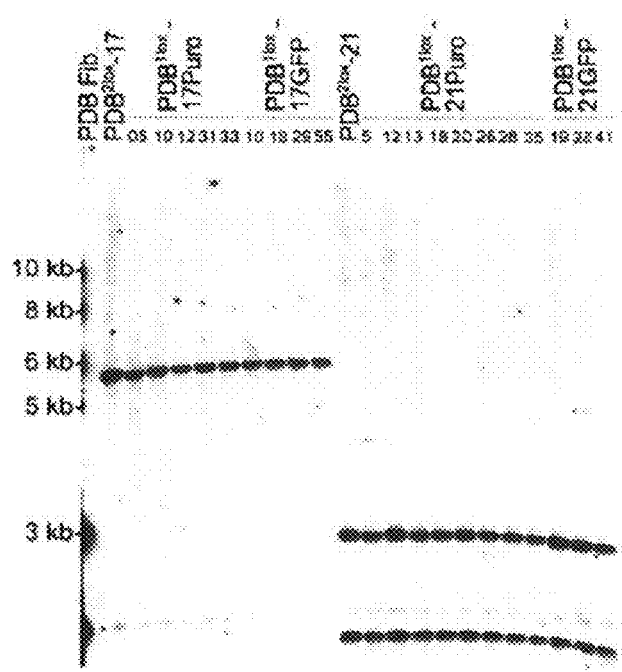
FIG. 35 shows Southern blot analysis for FUW-M2rtTA. Southern blot analysis of parental fibroblasts (PDB), provirus-carrying PDB$^{2lox}$ clones (PDB$^{2lox}$-17 and PDB$^{2lox}$-21) and the indicated PDB$^{1lox}$ clones for proviral integration of FUW-M2rtTA. Puro indicates clones which were isolated by puromycin selection; GFP indicates clones isolated by FACS sorting for EGFP (as shown in FIG. 30A). Genomic DNA was digested with MfeI and probed for proviral integrations using $^{32}$P-labeled DNA probes against FUW-M2rtTA.

We focused on two clones, with either 5 (PDB$^{2lox}$-21) or 7 (PDB$^{2lox}$-17) total integrations of the reprogramming factors to test whether the excision of the loxP site-flanked lentiviral vectors would generate transgene-free cells. Two different strategies for Cre-mediated vector excision were used (FIG. 30A): (1) Transient expression of a vector encoding Cre-recombinase and the puromycin resistance marker (pCre-PAC). Following electroporation, the cells were selected with puromycin for 48 hours to enrich for cells that transiently expressed Cre-recombinase and puromycin. (2) Co-transfection of Cre-recombinase with an EGFP expression plasmid and subsequent FACS sorting for EGFP positive and Cre-expressing cells 60 hours after transfection. Using these two methods we isolated a total of 180 clones 10 to 14 days after electroporation (FIG. 30A). Initial Southern blot analysis to screen for the excision of KLF4 (highest number of integrations) using an internal EcoRI digest showed that 48 clones were negative for KLF4 lentiviral integrations (Data not shown). Subsequent Southern blot analysis for KLF4, OCT4 and SOX2 proviral integrations using an external XbaI restriction digest revealed that 7 clones derived from PDB$^{2lox}$-17 and 9 clones derived from PDB$^{2lox}$-21 had no integration of any of the reprogramming factors (FIG. 30B, referred to as PDB$^{1lox}$ clones). Excision of all reprogramming factors was confirmed by an additional Southern blot analysis using a different restriction digest (FIG. 34). Furthermore, PCR of genomic DNA using primers specific for Cre-recombinase confirmed that none of the PDB$^{1lox}$ clones had stably integrated the electroporated plasmids (data not shown). Southern blot analysis for the integration of the reverse tetracycline transactivator M2rtTA showed one integration for line PDB$^{2lox}$-17 and two integrations for line PDB$^{2lox}$-21 (FIG. 35). This means that the overall number of proviral integrations including the transactivator in line PDB$^{2lox}$-21 is the same as the number of excised transgenes from PDB$^{2lox}$-17 suggesting that the excision of all transgenes including the transactivator should be possible. Cytogenetic analysis demonstrated that 14 out of 14 analyzed clones showed a normal karyotype after Cre-mediated transgene excision (FIG. 30C and data not shown).

Figures 31A, 31B, 31C:
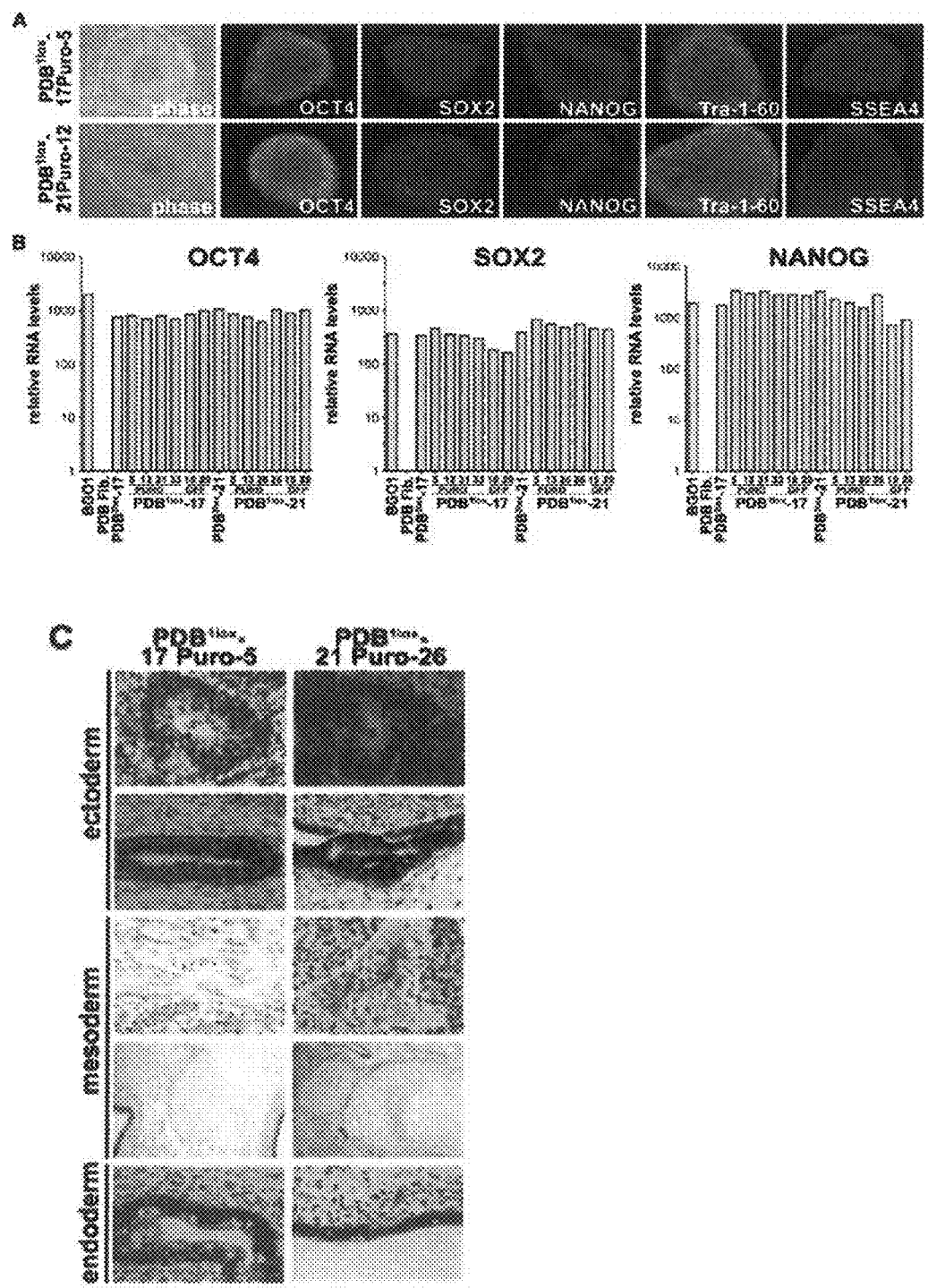
FIG. 31A-31E shows characterization of reprogramming factor-free hiPSCs.

All virus-free clones retained a stable hESC like morphology upon prolonged culture for more than 15 passages and maintained all the characteristics of hIPSCs such as expression of the hESC related marker proteins Tra-1-60, SSEA4, OCT4, SOX2 and NANOG as shown by immunocytochemistry (FIG. 31A), and the expression of the endogenous pluripotency related genes OCT4, SOX2 and NANOG (FIG. 31B) at levels comparable to hESCs and to the parental hiPSCs before excision of the transgenes. In order to demonstrate that the reprogramming factor-free PDB$^{1lox}$ clones maintain pluripotency after the excision of the reprogramming factors, independent PDB$^{1lox}$ clones were differentiated in vitro by EB formation or injected subcutaneously into SCID mice. All tested PDB$^{1lox}$ clones showed multi-lineage differentiation in vitro and developed into teratomas with contributions to all three embryonic germ layers (FIG. 31C).

Figure 31D:
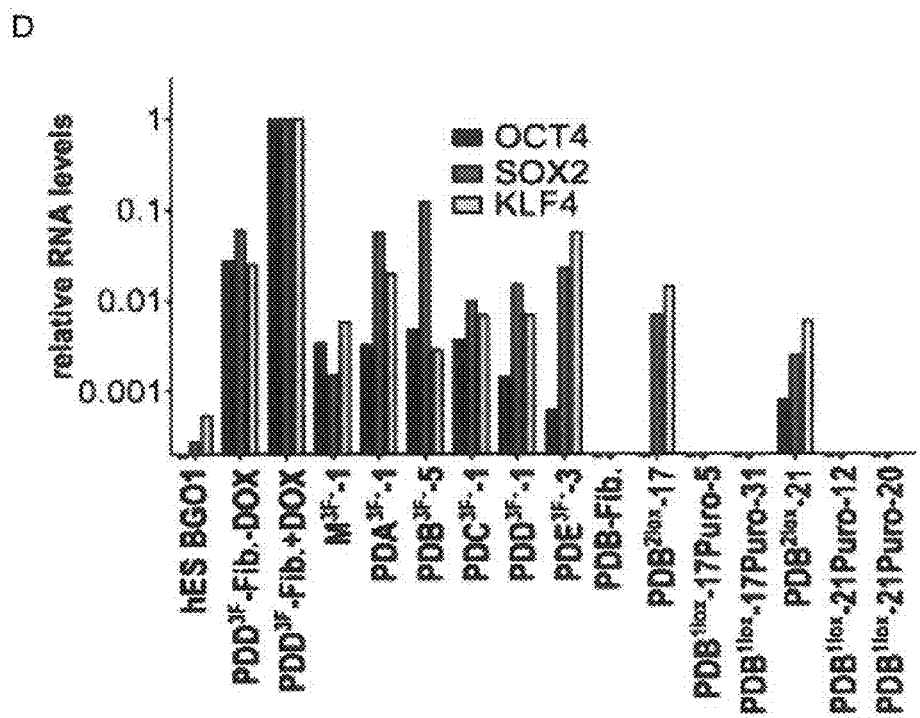

In order to compare residual transgene expression between distinct hiPSCs with integrated transgenes and factor-free hiPSCs, we performed quantitative RT-PCR using transgene-specific PCR primers. As reported previously using either lentiviral or Moloney-based retroviral vectors (Dimos et al., 2008; Ebert et al., 2008; Hockemeyer et al., 2008; Park et al., 2008a; Yu et al., 2007) we detected residual expression of the reprogramming factors for most of the transgenes in all cell lines with integrated viruses but not in uninfected fibroblasts, hESCs, or PDB$^{1lox}$ lines (FIG. 31D). Our results indicate that the use of loxP flanked vectors for reprogramming followed by Cre-mediated excision can efficiently generate reprogramming factor-free hiPSCs.

Figure 31E:
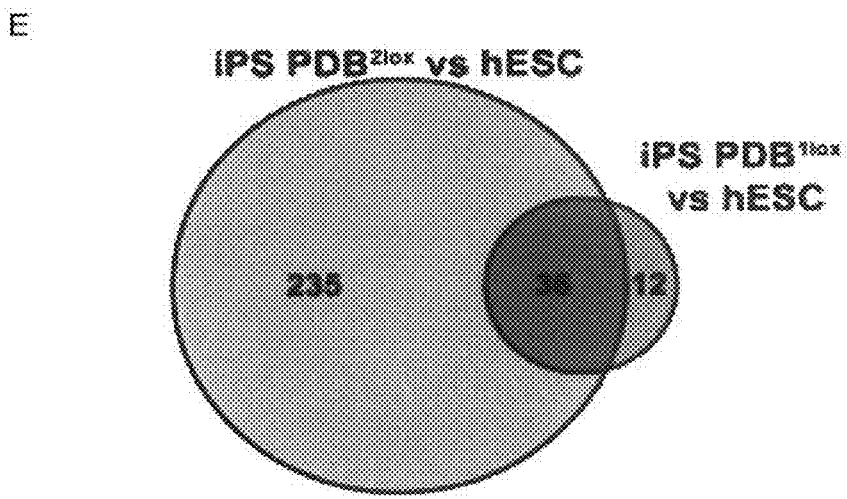

To address whether residual transgene expression could affect the overall gene expression profile of the reprogrammed cells, we compared hESCs, the parental fibroblasts, and hiPSCs before and after transgene excision by genome-wide gene expression analysis. Initial correlation analysis based on all genes which show at least a 4-fold expression difference between fibroblasts and hESCs confirmed that all hiPSCs are closely related to hESCs regardless of whether the transgenes were removed or not (see Soldner, et al. 2009, Supplemental FIG. 7). Despite the similarity of hESCs and hiPSCs statistical analysis comparing PDB$^{1lox}$ and PDB$^{2lox}$ cells in correlation to hESCs demonstrated that PDB$^{1lox}$ cells are more similar to hESCs than the parental PDB$^{2lox}$ cells (Soldner, et al. 2009, Supplemental FIG. 7). Notably, correlation analysis based on all genes showing at least a 2-fold expression difference between hiPSCs either with or without transgenes confirmed, that the gene expression profile of each individual PDB$^{1lox}$ line was more closely related to hESCs than to PDB$^{2lox}$ lines. (data not shown). In hiPSCs with viral integrations, 271 genes showed statistically significant differential expression as compared to hESCs (p<0.05) (FIG. 31E). Similar differences have been reported previously (Takahashi et al., 2007). In contrast only 48 genes were differentially expressed between transgene-free hiPSCs and hESCs (FIG. 31E). This represents a reduction of more than 80% of deregulated genes upon removal of the reprogramming factors. The remaining differentially expressed genes in factor-free hiPSCs are most likely due to either the diverse genetic background of hESCs and hiPSCs or the expression of the transactivator or a genetic memory of the reprogrammed somatic cell of origin. A detailed list of the differentially regulated genes is shown in Supplemental Table 1 of Soldner, et al., 2009.

Discussion

In the work described in this example we derived hiPSCs from skin biopsies obtained from patients with idiopathic PD. We developed a robust reprogramming protocol that allows the reproducible generation of patient-specific hiPSCs carrying a low number of proviral vector integrations. The use of modified lentiviruses carrying a loxP site flanking the integrated proviruses allowed the efficient removal of all transgene sequences and generated reprogramming-factor-free hiPSCs. The factor-free hiPSCs were pluripotent and, using molecular criteria, were more similar to embryo-derived hESCs than to the conventional vector-carrying parental hiPSCs. Efforts to understand the underlying pathophysiology of many neurodegenerative diseases such as PD are hampered by the lack of genuine in vitro models. Using hiPSC technology we established hiPSC lines from five patients with idiopathic PD using DOX-inducible lentiviral vectors transducing either 3 or 4 reprogramming factors. These cells were shown to have all of the features of pluripotent ES cells including the ability to differentiate into cell types of all embryonic lineages.

Our results indicate that removal of the integrated transgenes by Cre/lox mediated recombination can lead to vector-free hiPSCs. A previous report failed to excise transgenes flanked by loxP sites (Takahashi and Yamanaka, 2006). Without being bound by theory, this is probably due to the high number of retroviral integrations (more than 20) which made complete removal of all proviruses impossible or caused catastrophic genomic instability. Our results, based upon DOX-inducible lentiviral transduction, show that hiPSCs carrying as few as 3 or 4 viral integrations can be generated. Using DOX-inducible lentiviral vectors with a loxP site within the 3'LTR, we derived PD patient-specific reprogramming factor-free hiPSCs after Cre-recombinase mediated excision of the transgenes. Removal of the promoter and transgene sequences in self-inactivating (SIN) lentiviral vectors is expected to considerably reduce the risk of oncogenic transformation due to virus mediated oncogene activation and/or re-expression of the transduced transcription factors (Allen and Berns, 1996; von Kalle et al., 2004). The remaining risk of gene disruption could be eliminated by targeting the reprogramming factors as a polycistronic single expression vector flanked by loxP sites into a genomic safe-harbor locus.

Factor-Free hiPSCs Maintain a Pluripotent Esc Like State

Although silencing of transgene expression has been reported for several hiPSCs, all hiPSCs generated to date (including the lines described in this example prior to removal of the reprogramming factors), sustain a low but detectable residual transgene expression (Dimos et al., 2008; Ebert et al., 2008; Hockemeyer et al., 2008; Park et al., 2008a; Yu et al., 2007). The question of whether hiPSCs depend on the expression of the reprogramming factors to maintain a pluripotent ESC-like state has therefore not been conclusively resolved. The observation that factor-free hiPSCs were morphologically and biological indistinguishable from the parental hiPSCs and maintained all the characteristics of hESCs demonstrates that human somatic cells can be reprogrammed to a self-sustaining pluripotent state which can be maintained in the complete absence of the exogenous reprogramming factors. These results provide additional proof that hiPSCs reestablish a pluripotency related autoregulatory loop that has been proposed to rely on the activation of the four endogenous transcription factors OCT4, NANOG, SOX2 and TCF3 (Jaenisch and Young, 2008).

Residual Transgene Expression from Partially Silenced Viral Vectors Perturbs the Transcriptional Profile of hiPSCs Because the genomic integration site of a particular provirus influences proviral silencing as well as its risk of being reactivated, hiPSCs with identical and predictable properties cannot be generated by approaches relying on stochastic silencing. Residual transgene expression might affect the differentiation properties of iPSCs. Indeed, significant differences between mouse ES cells and iPSCs in their ability to differentiate into cardiomyocytes (K. Hochedlinger, personal communication) as well as partially blocked EB induced differentiation along with incomplete OCT4 and NANOG downregulation of distinct hiPSC clones (Yu et al., 2007) have been observed. These observations are consistent with the possibility that the variable basal transcription of only partially silenced vectors might influence the generation of functional differentiated cells.

In an effort to assess whether the removal of the vectors would affect the properties of the hiPSCs, we compared overall gene expression patterns in parental provirus-carrying hiPSCs, factor-free hiPSCs, and in embryo-derived hESCs. As reported previously (Park et al., 2008b; Takahashi et al., 2007; Yu et al., 2007), the provirus-carrying hiPSCs and factor-free hiPSCs clustered closely with the hESCs when compared to the donor fibroblasts. However, a more detailed analysis of the most divergent genes between the different hiPSCs cell types revealed that embryo-derived hESCs and factor-free hiPSCs were more closely related to each other than to the provirus-carrying parental hiPSCs. It is possible that the remaining small difference in gene expression between the vector-free hiPSCs and hESCs may be due to expression of the transactivator that had not been excised in our experiments. These results presented here provide clear evidence that the basal expression of proviruses carried in conventional iPS cells can affect the molecular characteristics of the cells. The system described here provides the basis to further elucidate the effect of residual transgene expression, e.g., in the context of in vitro and in vivo differentiation paradigms. Furthermore, these results demonstrate that the derivation of reprogramming factor-free hiPSCs is of great benefit not only for potential therapeutic applications, but also for biomedical research in order to develop more reliable and reproducible in vitro models of disease. To this end, we suggest that generating transgene-free hiPSCs by Cre-mediated excision offers significant advantages such as its high efficiency and experimental simplicity. The system described here has the potential to become a routine technology for the derivation of hiPSCs that will allow the generation of standardized hiPSCs from different sources using different combinations of reprogramming factors.

TABLE 4

Summary of hiPSCs Derived from Primary Fibroblasts

| Parental Cell Line | Donor[a] | Age at Onset of PD | Age at Biopsy | Reprogramming Factors | Number of iPSC Clones Characterized | iPSC Clone ID |
|---|---|---|---|---|---|---|
| AG20443 (PDA) | Parkinson's disease patient, idopathic, male | NA | 71 | FUW-tetO 3 factors (OCT4, SOX2, KLF4) | 2 | PDA[3F]-1, -5 |
| AG20442 (PDB) | Parkinson's disease patient, idopathic, male | 51 | 53 | FUW-tetO 3 factors (OCT4, SOX2, KLF4) | 5[b] | PDB[3F]-1, -5, -8, -9, PDB[3F]-d12 |
| AG20442 (PDB) | Parkinson's disease patient, idopathic, male | 51 | 53 | FUW-tetO 4 factors (OCT4, SOX2, KLF4, c-MYC) | 5[c] | PDB[4F]-1, -2, -3, -4, -5 |
| AG20446 (PDC) | Parkinson's disease patient, idopathic, male | 50 | 57 | FUW-tetO 3 factors (OCT4, SOX2, KLF4) | 1 | PDC[3F]-1 |
| AG20445 (PDD) | Parkinson's disease patient, idopathic, male | 44 | 60 | FUW-tetO 3 factors (OCT4, SOX2, KLF4) | 3 | PDD[3F]-1, -4, -7 |

TABLE 4-continued

Summary of hiPSCs Derived from Primary Fibroblasts

| Parental Cell Line | Donor[a] | Age at Onset of PD | Age at Biopsy | Reprogramming Factors | Number of iPSC Clones Characterized | iPSC Clone ID |
|---|---|---|---|---|---|---|
| AG20445 (PDD) | Parkinson's disease patient, idopathic, male | 44 | 60 | FUW-tetO 4 factors (OCT4, SOX2, KLF4, c-MYC) | 5 | PDD$^{4F}$-1,-4, -5, -8, -9 |
| AG08395 (PDE) | Parkinson's disease patient, idopathic, female | 83 | 85 | FUW-tetO 3 factors (OCT4, SOX2, KLF4) | 2 | PDE$^{3F}$-3, -4 |
| GM01786 | Dyskeratosis congenital carrier, female | — | 30 | FUW-tetO 3 factors (OCT4, SOX2, KLF4) | 2 | M$^{3F}$-1, -2 |
| GM01660 | Lesh-Nyhan carrier, female | — | 11 | FUW-tetO 3 factors (OCT4, SOX2, KLF4) | 2$^d$ | A1, A6 |
| MRC-5 | male, embryonic fibroblasts | | | FUW-tetO 4 factors (OCT4, SOX2, KLF4, c-MYC) | 2$^d$ | D1, D4 |

N/A Not available
[a]Additional information about these fibroblast cell lines can be obtained from the Coriell Institute.
[b]PDB$^{3F}$-12d was isolated in experiments to determine the temporal requirements of transgene expression. PDB$^{3F}$-12d was isolated from cultures exposed for 12 days to doxycycline.
[c]These cells were derived in experiments to determine the temporal requirements of transgene expression. PDB$^{4F}$-1 to -3 were isolated from cultures exposed for 8 days to doxycyline, whereas PDB$^{4F}$-4 and -5 were exposed to doxycycline for 10 and 12 days, respectively.
[d]These hiPSCs cells have been previously characterised in Hockemeyer et al., 2008.

References for Example 4

Aasen, T., Raya, A., Barrero, M. J., Garreta, E., Consiglio, A., Gonzalez, F., Vassena, R., Bilic, J., Pekarik, V., Tiscornia, G., et al. (2008). Efficient and rapid generation of induced pluripotent stem cells from human keratinocytes. Nat Biotechnol 26, 1276-1284.

Allen, J. D., and Berns, A. (1996). Complementation tagging of cooperating oncogenes in knockout mice. Semin Cancer Biol 7, 299-306.

Brambrink, T., Foreman, R., Welstead, G. G., Lengner, C. J., Wernig, M., Suh, H., and Jaenisch, R. (2008). Sequential expression of pluripotency markers during direct reprogramming of mouse somatic cells. Cell Stem Cell 2, 151-159.

Carey, B. W., Markoulaki, S., Hanna, J., Saha, K., Gao, Q., Mitalipova, M., and Jaenisch, R. (2009). Reprogramming of murine and human somatic cells using a single polycistronic vector. Proc Natl Acad Sci USA 106, 157-162.

Costa, M., Dottori, M., Sourris, K., Jamshidi, P., Hatzistavrou, T., Davis, R., Azzola, L., Jackson, S., Lim, S. M., Pera, M., et al. (2007). A method for genetic modification of human embryonic stem cells using electroporation. Nat Protoc 2, 792-796.

de Lau, L. M., and Breteler, M. M. (2006). Epidemiology of Parkinson's disease. Lancet Neurol 5, 525-535.

Dimos, J. T., Rodolfa, K. T., Niakan, K. K., Weisenthal, L. M., Mitsumoto, H., Chung, W., Croft, G. F., Saphier, G., Leibel, R., Goland, R., et al. (2008). Induced pluripotent stem cells generated from patients with ALS can be differentiated into motor neurons. Science 321, 1218-1221.

Ebert, A. D., Yu, J., Rose, F. F., Jr., Mattis, V. B., Lorson, C. L., Thomson, J. A., and Svendsen, C. N. (2009). Induced pluripotent stem cells from a spinal muscular atrophy patient. Nature 457, 277-280.

Elkabetz, Y., Panagiotakos, G., Al Shamy, G., Socci, N. D., Tabar, V., and Studer, L. (2008). Human ES cell-derived neural rosettes reveal a functionally distinct early neural stem cell stage. Genes Dev 22, 152-165.

Gasser, T. (2007). Update on the genetics of Parkinson's disease. Mov Disord 22 Suppl 17, S343-350.

Hanna, J., Wernig, M., Markoulaki, S., Sun, C. W., Meissner, A., Cassady, J. P., Beard, C., Brambrink, T., Wu, L. C., Townes, T. M., et al. (2007). Treatment of sickle cell anemia mouse model with iPS cells generated from autologous skin. Science 318, 1920-1923.

Hochedlinger, K., Yamada, Y., Beard, C., and Jaenisch, R. (2005). Ectopic expression of Oct-4 blocks progenitor-cell differentiation and causes dysplasia in epithelial tissues. Cell 121, 465-477.

Hockemeyer, D., Soldner, F., Cook, E. G., Gao, Q., Mitalipova, M., and Jaenisch, R. (2008). A drug-inducible system for direct reprogramming of human somatic cells to pluripotency. Cell Stem Cell 3, 346-353.

Huangfu, D., Osafune, K., Maehr, R., Guo, W., Eijkelenboom, A., Chen, S., Muhlestein, W., and Melton, D. A. (2008). Induction of pluripotent stem cells from primary human fibroblasts with only Oct4 and Sox2. Nat Biotechnol 26, 1269-1275.

Jaenisch, R., and Young, R. (2008). Stem cells, the molecular circuitry of pluripotency and nuclear reprogramming. Cell 132, 567-582.

Kim, B. K., Kim, S. E., Shim, J. H., Woo, D. H., Gil, J. E., Kim, S. K., and Kim, J. H. (2006). Neurogenic effect of vascular endothelial growth factor during germ layer formation of human embryonic stem cells. FEBS Lett 580, 5869-5874.

Lowry, W. E., Richter, L., Yachechko, R., Pyle, A. D., Tchieu, J., Sridharan, R., Clark, A. T., and Plath, K. (2008). Generation of human induced pluripotent stem cells from dermal fibroblasts. Proc Natl Acad Sci USA 105, 2883-2888.

Maherali, N., Ahfeldt, T., Rigamonti, A., Utikal, J., Cowan, C., and Hochedlinger, K. (2008). A high-efficiency system for the generation and study of human induced pluripotent stem cells. Cell Stem Cell 3, 340-345.

Markoulaki, S., Hanna, J., Beard, C., Carey, B. W., Cheng, A. W., Lengner, C. J., Dausman, J. A., Fu, D., Gao, Q., Wu, S., et al. (2009). Transgenic mice with defined combinations of drug-inducible reprogramming factors. Nat Biotechnol.

Nakagawa, M., Koyanagi, M., Tanabe, K., Takahashi, K., Ichisaka, T., Aoi, T., Okita, K., Mochiduki, Y., Takizawa, N., and Yamanaka, S. (2008). Generation of induced pluripotent stem cells without Myc from mouse and human fibroblasts. Nat Biotechnol 26, 101-106.

Okita, K., Ichisaka, T., and Yamanaka, S. (2007). Generation of germline-competent induced pluripotent stem cells. Nature 448, 313-317.

Okita, K., Nakagawa, M., Hyenjong, H., Ichisaka, T., and Yamanaka, S. (2008). Generation of mouse induced pluripotent stem cells without viral vectors. Science 322, 949-953.

Park, I. H., Arora, N., Huo, H., Maherali, N., Ahfeldt, T., Shimamura, A., Lensch, M. W., Cowan, C., Hochedlinger, K., and Daley, G. Q. (2008a). Disease-Specific Induced Pluripotent Stem Cells. Cell.

Park, I. H., Zhao, R., West, J. A., Yabuuchi, A., Huo, H., Ince, T. A., Lerou, P. H., Lensch, M. W., and Daley, G. Q. (2008b). Reprogramming of human somatic cells to pluripotency with defined factors. Nature 451, 141-146.

Perrier, A. L., Tabar, V., Barberi, T., Rubio, M. E., Bruses, J., Topf, N., Harrison, N. L., and Studer, L. (2004). Derivation of midbrain dopamine neurons from human embryonic stem cells. Proc Natl Acad Sci USA 101, 12543-12548.

Roy, N. S., Cleren, C., Singh, S. K., Yang, L., Beal, M. F., and Goldman, S. A. (2006). Functional engraftment of human ES cell-derived dopaminergic neurons enriched by coculture with telomerase-immortalized midbrain astrocytes. Nat Med 12, 1259-1268.

Schulz, J. B. (2008). Update on the pathogenesis of Parkinson's disease. J Neurol 255 Suppl 5, 3-7.

Shi, Y., Desponts, C., Do, J. T., Hahm, H. S., Scholer, H. R., and Ding, S. (2008a). Induction of pluripotent stem cells from mouse embryonic fibroblasts by Oct4 and Klf4 with small-molecule compounds. Cell Stem Cell 3, 568-574.

Shi, Y., Do, J. T., Desponts, C., Hahm, H. S., Scholer, H. R., and Ding, S. (2008b). A combined chemical and genetic approach for the generation of induced pluripotent stem cells. Cell Stem Cell 2, 525-528.

Soldner F, Hockemeyer D, Beard C, Gao Q, Bell G W, Cook E G, Hargus G, Blak A, Cooper O, Mitalipova M, Isacson O, Jaenisch R. (2009) Parkinson's disease patient-derived induced pluripotent stem cells free of viral reprogramming factors. Cell. 136(5):964-77.

Sonntag, K. C., Pruszak, J., Yoshizaki, T., van Arensbergen, J., Sanchez-Pernaute, R., and Isacson, O. (2007). Enhanced yield of neuroepithelial precursors and midbrain-like dopaminergic neurons from human embryonic stem cells using the bone morphogenic protein antagonist noggin. Stem Cells 25, 411-418.

Stadtfeld, M., Nagaya, M., Utikal, J., Weir, G., and Hochedlinger, K. (2008). Induced pluripotent stem cells generated without viral integration. Science 322, 945-949.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Taniguchi, M., Sanbo, M., Watanabe, S., Naruse, I., Mishina, M., and Yagi, T. (1998). Efficient production of Cre-mediated site-directed recombinants through the utilization of the puromycin resistance gene, pac: a transient gene-integration marker for ES cells. Nucleic Acids Res 26, 679-680.

Trounson, A. (2009). Rats, cats, and elephants, but still no unicorn: induced pluripotent stem cells from new species. Cell Stem Cell 4, 3-4.

von Kalle, C., Fehse, B., Layh-Schmitt, G., Schmidt, M., Kelly, P., and Baum, C. (2004). Stem cell clonality and genotoxicity in hematopoietic cells: gene activation side effects should be avoidable. Semin Hematol 41, 303-318.

Wernig, M., Meissner, A., Cassady, J. P., and Jaenisch, R. (2008). c-Myc is dispensable for direct reprogramming of mouse fibroblasts. Cell Stem Cell 2, 10-12.

Wernig, M., Meissner, A., Foreman, R., Brambrink, T., Ku, M., Hochedlinger, K., Bernstein, B. E., and Jaenisch, R. (2007). In vitro reprogramming of fibroblasts into a pluripotent ES-cell-like state. Nature 448, 318-324.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al, (2007). Induced pluripotent stem cell lines derived from human somatic cells. Science 318, 1917-1920.

What is claimed is:

1. A nucleic acid construct comprising at least three coding regions, a first coding region encoding a first reprogramming factor, a second coding region encoding a second reprogramming factor, and a third coding region that encodes a third reprogramming factor, wherein the first and second coding regions are linked by a nucleic acid that encodes a first self-cleaving peptide and the second and third coding regions are linked by a nucleic acid that encodes a second self-cleaving peptide so as to form a single open reading frame, wherein expression of the first, second, and third reprogramming factors is sufficient for reprogramming a mammalian somatic cell to pluripotency, wherein any two consecutive self-cleaving peptides are not the same, and wherein the nucleic acid construct does not comprise Oct 3/4, Sox 2 and Klf4 ligated across the 2A sequence of foot-and-mouth disease virus in the order of Oct 3/4, Klf4 and Sox2; and wherein the nucleic acid construct does not comprise c-Myc.

2. The nucleic acid construct of claim 1, further comprising a fourth coding region that encodes a fourth reprogramming factor.

3. The nucleic acid construct of claim 1, wherein:
the first or second self-cleaving peptide is a viral 2A peptide or the first and second self-cleaving peptide are a viral 2A peptide.

4. An expression cassette comprising: the nucleic acid construct of claim 1 operably linked to a promoter, wherein the promoter drives transcription of a polycistronic message that encodes the reprogramming factors.

5. An expression vector comprising: the expression cassette of claim 4.

6. An isolated mammalian cell comprising: the expression cassette of claim 4.

7. The nucleic acid construct of claim 3, wherein the viral 2A peptide is an aphthovirus 2A peptide.

8. The nucleic acid construct of claim 3, wherein the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

9. The nucleic acid construct of claim 1, wherein the coding regions encode a set of reprogramming factors selected from the group consisting of: (i) Oct4, Klf4, and Sox2; (ii) Oct4, Nanog, and Lin28; (iii) Oct4, Nanog, and Sox2.

10. The nucleic acid construct of claim 1, wherein the coding regions encode a set of reprogramming factors selected from the group consisting of: Oct4, Klf4, and Sox2.

11. The nucleic acid construct of claim 1, wherein:
(a) the reprogramming factors are selected from the group consisting of: Oct4, Nanog, Sox2, Klf4, and Lin28, and c Myc; or
(b) the construct does not encode one of the reprogramming factors selected from the group consisting of: Oct4, Klf4, Sox2, Lin28, and Nanog.

12. The isolated mammalian cell of claim 6, wherein the cell expresses three reprogramming factors from the expression cassette.

13. The isolated mammalian cell of claim 6, wherein the cell expresses three reprogramming factors from the expression cassette, wherein the three reprogramming factors are not sufficient to reprogram mammalian fibroblasts with an efficiency of at least 0.05%.

14. The isolated mammalian cell of claim 6, wherein:
(a) the cell is selected from the group consisting of: a somatic cell, a terminally differentiated somatic cell, and an iPS cell; or
(b) the cell is a human cell; or
(c) the cell further comprises a reporter gene integrated at a locus whose activation serves as a marker of reprogramming to pluripotency.

15. The isolated mammalian cell of claim 6, wherein the cell expresses three reprogramming factors from the expression cassette, wherein the three reprogramming factors are sufficient to reprogram mammalian fibroblasts with an efficiency of at least 0.05%.

16. The expression cassette of claim 4, further comprising one or more sites that mediate integration into the genome of a mammalian cell.

17. The expression vector of claim 5, wherein
(a) the vector is retroviral; or
(b) the promoter is inducible.

* * * * *

UNITED STATES PATENT AND TRADEMARK OFFICE
CERTIFICATE OF CORRECTION

Page 1 of 1

PATENT NO. : 9,497,943 B2
APPLICATION NO. : 12/997815
DATED : November 22, 2016
INVENTOR(S) : Rudolf Jaenisch and Bryce Woodbury Carey It is certified that error appears in the above-identified patent and that said Letters Patent is hereby corrected as shown below:

In the Claims

Column 76, Claim 11, Lines 26-27, the phrase ", and c Myc" should be removed.

Signed and Sealed this
Twenty-eighth Day of March, 2017

Michelle K. Lee
*Director of the United States Patent and Trademark Office*